US007381818B2

(12) United States Patent
Lokhov et al.

(10) Patent No.: US 7,381,818 B2
(45) Date of Patent: Jun. 3, 2008

(54) FLUORESCENT PROBES CONTAINING 5'-MINOR GROOVE BINDER, FLUOROPHORE AND QUENCHING MOIETIES AND METHODS OF USE THEREOF

(75) Inventors: Sergey Lokhov, Kirkland, WA (US); Eugene Lukhtanov, Bothell, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 300 days.

(21) Appl. No.: 10/976,365

(22) Filed: Oct. 27, 2004

(65) Prior Publication Data

US 2005/0214797 A1    Sep. 29, 2005

Related U.S. Application Data

(60) Provisional application No. 60/515,523, filed on Oct. 28, 2003.

(51) Int. Cl.
*C07H 21/04* (2006.01)
*C12P 19/34* (2006.01)

(52) U.S. Cl. .................... 536/24.3; 435/91.2
(58) Field of Classification Search ............ None
See application file for complete search history.

(56) References Cited

U.S. PATENT DOCUMENTS

| | | | |
|---|---|---|---|
| 5,188,934 | A | 2/1993 | Menchen et al. |
| 5,419,966 | A | 5/1995 | Reed et al. |
| 5,512,677 | A | 4/1996 | Chern et al. |
| 5,585,481 | A | 12/1996 | Arnold, Jr. et al. |
| 5,696,251 | A | 12/1997 | Arnold, Jr. et al. |
| 5,723,591 | A | 3/1998 | Livak et al. |
| 5,736,626 | A | 4/1998 | Mullah et al. |
| 5,801,155 | A | 9/1998 | Kutyavin et al. |
| RE36,169 | E | 3/1999 | Furutani |
| 5,876,930 | A | 3/1999 | Livak et al. |
| 5,925,517 | A | 7/1999 | Tyagi et al. |
| 5,942,610 | A | 8/1999 | Nelson et al. |
| 6,030,787 | A | 2/2000 | Tivak et al. |
| 6,084,102 | A | 7/2000 | Kutyavin et al. |
| 6,127,121 | A | 10/2000 | Meyer et al. |
| 6,214,979 | B1 | 4/2001 | Gelfand et al. |
| 6,339,147 | B1 | 1/2002 | Lukhtanov et al. |
| 6,441,159 | B1 | 8/2002 | Lukhtanov et al. |
| 6,472,153 | B1 | 10/2002 | Dempcy et al. |
| 6,486,303 | B1 | 11/2002 | Moyle |
| 6,492,346 | B1 | 12/2002 | Hedgpeth et al. |
| 6,596,490 | B2 | 7/2003 | Dattagupta |
| 6,660,845 | B1 | 12/2003 | Gall et al. |
| 6,683,173 | B2 | 1/2004 | Dempcy et al. |
| RE38,416 | E | 2/2004 | Petrie et al. |
| 6,727,356 | B1 | 4/2004 | Reed et al. |
| 6,790,945 | B2 | 9/2004 | Lukhtanov et al. |
| 7,045,610 | B2 | 5/2006 | Dempcy et al. |
| 2003/0175728 | A1* | 9/2003 | Belousov et al. ............... 435/6 |
| 2005/0118623 | A1 | 6/2005 | Belousov et al. |
| 2005/0187383 | A1 | 8/2005 | Lukhtanov et al. |

FOREIGN PATENT DOCUMENTS

| | | |
|---|---|---|
| EP | 87310256.0 A2 | 11/1987 |
| WO | WO 91/105060 A2 | 4/1991 |
| WO | WO 99/51621 A2 | 10/1999 |
| WO | WO 01/64958 A2 | 9/2001 |
| WO | WO 03/022859 A2 | 3/2003 |
| WO | WO 03/023357 A2 | 3/2003 |
| WO | WO 03/026657 A1 | 4/2003 |
| WO | WO 03/062445 A2 | 7/2003 |
| WO | WO 2003/062445 A2 * | 7/2003 |

OTHER PUBLICATIONS

Afonina et al., Hybridization-triggered fluorescence detection of DNA with minor groove binder-conjugated probes, Proceedings of SPIE vol. 4626 (2002) pp. 322-331.*
Kutyanin et al., 3' Minor groove binder-DNA probes increase sequence specificity at PCR extension temperatures, Nucleic Acids Research, 2000, vol. 28, No. 2, pp. 655-661.*
U.S. Appl. No. 60/505,792, filed Sep. 25, 2003, Chipman et al.
U.S. Appl. No. 60/601,599, filed Aug. 13, 2004, Lukhtanov et al.
Afonina et al., "Minor Groove Binder-Conjugated DNA Probes for Quantitative DNA Detection by Hybridization-Triggered Flourescence," *BioTechniques*, Apr. 2002, vol. 32, No. 4, pp. 940-949.
Fang et al., "Designing a Novel Molecular Beacon for Surface-Immobilized DNA Hibridization Studies," *Journal of the American Chemical Society*, 1999. vol. 121, pp. 2921-2922.
Lukhtanov, et al., "Oligodeoxynucleotides with Conjugated Dihypropyrroloindole Oligopeptides: Preparation and Hybridization Properties," *Bioconjugate Chemistry*, 1995, vol. 6, pp. 418-426.

* cited by examiner

*Primary Examiner*—Kenneth R. Horlick
*Assistant Examiner*—Mark Staples
(74) *Attorney, Agent, or Firm*—Townsend and Townsend and Crew LLP

(57) ABSTRACT

Minor groove binder-oligonucleotide probes are provided along with methods for their use wherein the probes have an attached fluorophore which, in an unhybridized form exhibits very low background signal.

34 Claims, 7 Drawing Sheets

```
                          SEQUENCE LISTING

<160> NUMBER OF SEQ ID NOS: 28

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:random
      coiled probe MB-Fl-ODN-Q
<220> FEATURE:
<221> NAME/KEY: modified_base
<222> LOCATION: (1)
<223> OTHER INFORMATION: n = a modified by minor groove binder (MB, MGB)
<220> FEATURE:
<221> NAME/KEY: modified_base
<222> LOCATION: (15)
<223> OTHER INFORMATION: n = t modified by Eclipse quencher (Q)

<400> SEQUENCE: 1
natactgagc ttgcn                                                    15

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:target
      sequence

<400> SEQUENCE: 2
gtgcctcagt ctctgtatgt ggtgggacg                                     29

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:MGB Eclipse
      probe
<220> FEATURE:
<221> NAME/KEY: modified_base
<222> LOCATION: (12)
<223> OTHER INFORMATION: n =
      4-(4,6-diamino-1H-pyrazolo[3,4-d]pyrimidin-3-yl)-
      but-3-yn-1-ol (A*, Super A)
<220> FEATURE:
<221> NAME/KEY: modified_base
<222> LOCATION: (15)
<223> OTHER INFORMATION: n =
      4-(4,6-diamino-1H-pyrazolo[3,4-d]pyrimidin-3-yl)-
      but-3-yn-1-ol (A*, Super A)

<400> SEQUENCE: 3
cagagacata cnccn                                                    15

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:New probe,
      New probe #1
<220> FEATURE:
<221> NAME/KEY: modified_base
```

```
<222> LOCATION: (1)
<223> OTHER INFORMATION: n = 6-amino-1H-pyrazolo[3,4-d]pyrimidin-4(5H)-
      one (ppG, PPG, G* or Super G)
<220> FEATURE:
<221> NAME/KEY: modified_base
<222> LOCATION: (7)
<223> OTHER INFORMATION: n = 6-amino-1H-pyrazolo[3,4-d]pyrimidin-4(5H)-
      one (ppG, PPG, G* or Super G)
<220> FEATURE:
<221> NAME/KEY: modified_base
<222> LOCATION: (14)
<223> OTHER INFORMATION: n =
      4-(4,6-diamino-1H-pyrazolo[3,4-d]pyrimidin-3-yl)-
      but-3-yn-1-ol (A*, Super A)

<400> SEQUENCE: 4
ntcaganaca tacncc                                                   16

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:target
      sequence

<400> SEQUENCE: 5
gtgcctcagt ctctgtatgt ggtgggacg                                     29

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:MGB Eclipse
      probe
<220> FEATURE:
<221> NAME/KEY: modified_base
<222> LOCATION: (12)
<223> OTHER INFORMATION: n =
      4-(4,6-diamino-1H-pyrazolo[3,4-d]pyrimidin-3-yl)-
      but-3-yn-1-ol (A*, Super A)

<400> SEQUENCE: 6
cagacacata cncca                                                    15

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence:New probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G)

<400> SEQUENCE: 7
ntcagacaca tacacc                                                   16

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:target
      sequence

<400> SEQUENCE: 8
```

```
ccaccacata cagagactga ggcactg                                          27
```

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence:Eclipse or
    New probe, Eclipse #2 probe, New probe #2
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
    one (ppG, PPG, G* or Super G)

<400> SEQUENCE: 9

```
ntatgtctct gactcc                                                      16
```

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:target
    sequence

<400> SEQUENCE: 10

```
ccaccacata cagagactga ggcactg                                          27
```

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence:Eclipse or
    New probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
    one (ppG, PPG, G* or Super G)
<220> FEATURE:
<221> NAME/KEY: modified_base
<222> LOCATION: (7)
<223> OTHER INFORMATION: n = 6-amino-1H-pyrazolo[3,4-d]pyrimidin-4(5H)-
    one (ppG, PPG, G* or Super G)

<400> SEQUENCE: 11

```
ntatgtntct gactcc                                                      16
```

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence:Eclipse #1
    probe
<220> FEATURE:
<221> NAME/KEY: modified_base
<222> LOCATION: (12)
<223> OTHER INFORMATION: n =
    4-(4,6-diamino-1H-pyrazolo[3,4-d]pyrimidin-3-yl)-
    but-3-yn-1-ol (A*, Super A)

<400> SEQUENCE: 12

```
cagagacata cncca                                                       15
```

<210> SEQ ID NO 13
<211> LENGTH: 16
<212> TYPE: DNA

```
<213> ORGANISM: Artificial Sequence
<220> FEATURE:
<223> OTHER INFORMATION: Description of Artificial Sequence:MB-Fl-ODN
      probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G)

<400> SEQUENCE: 13
natgtgtccg tgtctc                                                          16

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
      complementary target, complement sequence, Complement 1

<400> SEQUENCE: 14
aaagagacac ggacacatca atccat                                               26

<210> SEQ ID NO 15
<211> LENGTH: 162
<212> TYPE: DNA
<213> ORGANISM: Artificial Sequence
<220> FEATURE:
<223> OTHER INFORMATION: Description of Artificial Sequence:portion of
      ARNT-01 target sequence with [G/C] polymorphism

<400> SEQUENCE: 15
gtgtgctgcc aaaccattca gactgtggct ggttcaaaac aggagtcacg gagtcagasa         60
catacaccac cctgcctgtc tcacatgaga caataaacag aaagccatct gctgcctcca        120
agatcaaatg tttcagttcc tgcgcaagaa aaagaaatag aa                           162

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:Eclipse
      fluorogenic probe
<220> FEATURE:
<221> NAME/KEY: modified_base
<222> LOCATION: (1)
<223> OTHER INFORMATION: n = g modified by minor groove binder (MB)
      dihydrocyclopyrroloindole triamide (DPI-3)
      and Eclipse quencher (Q)
<220> FEATURE:
<221> NAME/KEY: modified_base
<222> LOCATION: (16)
<223> OTHER INFORMATION: n = c modified by 6-carboxyfluorescein (FAM)

<400> SEQUENCE: 16
ntatgtctct gactcn                                                          16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence:Eclipse
      fluorogenic probe
<220> FEATURE:
<221> NAME/KEY: modified_base
<222> LOCATION: (1)
<223> OTHER INFORMATION: n = g modified by minor groove binder (MB)
```

```
        dihydrocyclopyrroloindole triamide (DPI-3)
        and Eclipse quencher (Q)
<220> FEATURE:
<221> NAME/KEY: modified_base
<222> LOCATION: (16)
<223> OTHER INFORMATION: n = c modified by Yakima Yellow (YY)

<400> SEQUENCE: 17
ntatgtctct gactcn                                                   16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:New
        fluorogenic probe
<220> FEATURE:
<221> NAME/KEY: modified_base
<222> LOCATION: (1)
<223> OTHER INFORMATION: n = g modified by minor groove binder (MB)
        dihydrocyclopyrroloindole triamide (DPI-3)
        and 6-carboxyfluorescein (FAM)
<220> FEATURE:
<221> NAME/KEY: modified_base
<222> LOCATION: (16)
<223> OTHER INFORMATION: n = c modified by Eclipse quencher (Q)

<400> SEQUENCE: 18
ntatgtctct gactcn                                                   16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:New
        fluorogenic probe
<220> FEATURE:
<221> NAME/KEY: modified_base
<222> LOCATION: (1)
<223> OTHER INFORMATION: n = g modified by minor groove binder (MB)
        dihydrocyclopyrroloindole triamide (DPI-3)
        and Yakima Yellow (YY)
<220> FEATURE:
<221> NAME/KEY: modified_base
<222> LOCATION: (16)
<223> OTHER INFORMATION: n = c modified by Eclipse quencher (Q)

<400> SEQUENCE: 19
ntatgtctct gactcn                                                   16

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence:Eclipse #1
        probe
<220> FEATURE:
<221> NAME/KEY: modified_base
<222> LOCATION: (1)
<223> OTHER INFORMATION: n = c modified by minor groove binder (MB) and
        quencher (Q)
<220> FEATURE:
<221> NAME/KEY: modified_base
<222> LOCATION: (12)
<223> OTHER INFORMATION: n =
        4-(4,6-diamino-1H-pyrazolo[3,4-d]pyrimidin-3-yl)-
        but-3-yn-1-ol (A*, Super A)
<220> FEATURE:
<221> NAME/KEY: modified_base
<222> LOCATION: (15)
```

```
<223> OTHER INFORMATION: n = a modified by 6-carboxyfluorescein (FAM) or
      Yakima Yellow (YY)

<400> SEQUENCE: 20
nagagacata cnccn                                                          15

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence:Eclipse #2
      probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G) modified by minor groove
      binder (MB) and quencher (Q)
<220> FEATURE:
<221> NAME/KEY: misc_structure
<222> LOCATION: (16)
<223> OTHER INFORMATION: n = c modified by 6-carboxyfluorescein (FAM) or
      Yakima Yellow (YY)

<400> SEQUENCE: 21
ntatgtctct gactcn                                                         16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:New probe #1
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G) modified by minor groove
      binder (MB) and 6-carboxyfluorescein (FAM) or
      Yakima Yellow (YY)
<220> FEATURE:
<221> NAME/KEY: modified_base
<222> LOCATION: (7)
<223> OTHER INFORMATION: n = 6-amino-1H-pyrazolo[3,4-d]pyrimidin-4(5H)-
      one (ppG, PPG, G* or Super G)
<220> FEATURE:
<221> NAME/KEY: modified_base
<222> LOCATION: (14)
<223> OTHER INFORMATION: n =
      4-(4,6-diamino-1H-pyrazolo[3,4-d]pyrimidin-3-yl)-
      but-3-yn-1-ol (A*, Super A)
<220> FEATURE:
<221> NAME/KEY: modified_base
<222> LOCATION: (16)
<223> OTHER INFORMATION: n = c modified by quencher (Q)

<400> SEQUENCE: 22
ntcaganaca tacncn                                                         16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence:New probe #2
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G) modified by minor groove
      binder (MB) and 6-carboxyfluorescein (FAM) or
      Yakima Yellow (YY)
```

```
<220> FEATURE:
<221> NAME/KEY: modified_base
<222> LOCATION: (16)
<223> OTHER INFORMATION: n = c modified by quencher (Q)

<400> SEQUENCE: 23
ntatgtctct gactcn                                                       16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:probe
      sequence with quencher, New probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G) modified by minor groove
      binder (MB) and 6-carboxyfluorescein (FAM)
<220> FEATURE:
<221> NAME/KEY: modified_base
<222> LOCATION: (16)
<223> OTHER INFORMATION: n = c modified by Eclipse Quencher (Q)

<400> SEQUENCE: 24
natgtgtccg tgtctn                                                       16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence:MGB Eclipse
      probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G) modified by minor groove
      binder (MB) and Eclipse quencher (Q)
<220> FEATURE:
<221> NAME/KEY: modified_base
<222> LOCATION: (16)
<223> OTHER INFORMATION: n = c modified by 6-carboxyfluorescein (FAM)

<400> SEQUENCE: 25
natgtgtccg tgtctn                                                       16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence:New probe
<220> FEATURE:
<221> NAME/KEY: modified_base
<222> LOCATION: (1)
<223> OTHER INFORMATION: n = 6-amino-1H-pyrazolo[3,4-d]pyrimidin-4(5H)-
      one (ppG, PPG, G* or Super G) modified by minor groove
      binder (MB) and 6-carboxyfluorescein (FAM)
<220> FEATURE:
<221> NAME/KEY: modified_base
<222> LOCATION: (7)
<223> OTHER INFORMATION: n = 6-amino-1H-pyrazolo[3,4-d]pyrimidin-4(5H)-
      one (ppG, PPG, G* or Super G)
<220> FEATURE:
<221> NAME/KEY: modified_base
<222> LOCATION: (14)
<223> OTHER INFORMATION: n =
      4-(4,6-diamino-1H-pyrazolo[3,4-d]pyrimidin-3-yl)-
      but-3-yn-1-ol (A*, Super A)
```

```
<220> FEATURE:
<221> NAME/KEY: modified_base
<222> LOCATION: (16)
<223> OTHER INFORMATION: n = c modified by quencher (Q)

<400> SEQUENCE: 26
ntcaganaca tacncn                                                    16

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:Molecular
      Beacon probe
<220> FEATURE:
<221> NAME/KEY: modified_base
<222> LOCATION: (1)
<223> OTHER INFORMATION: n = c modified by 6-carboxyfluorescein (FAM)
<220> FEATURE:
<221> NAME/KEY: modified_base
<222> LOCATION: (27)
<223> OTHER INFORMATION: n = g modified by quencher (Q)

<400> SEQUENCE: 27
nggcgagtca gagacataca ccagccn                                        27

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:target
      complement

<400> SEQUENCE: 28
gcagggtggt gtatgtctct gactccgtg                                      29
```

FLUORESCENT PROBES CONTAINING 5'-MINOR GROOVE BINDER, FLUOROPHORE AND QUENCHING MOIETIES AND METHODS OF USE THEREOF

CROSS-REFERENCES TO RELATED APPLICATIONS

This application claims the benefit under 35 USC § 119e of U.S. Provisional Application Ser. No. 60/515,523, filed Oct. 28, 2003, the disclosure of which is incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

BACKGROUND OF THE INVENTION

DNA probes are established tools for sequence detection and quantification. Efficiency and accuracy of sequence detection depend on both hybridization specificity of the probe and its sensitivity. Fluorescence is one the most common ways to detect the hybridization event. Methods that use fluorescent probes for nucleic acid detection are based either on a hybridization-triggered fluorescence of intact probes (e.g., molecular beacons, and linear probes, see U.S. Pat. No. 6,030,787, U.S. Pat. No. 6,214,979, U.S. Pat. No. 5,925,517, U.S. Pat. No. 5,723,591 and U.S. application Ser. No. 10/165,410) or on a quenched-fluorescence release of a probe digested by DNA Polymerase (e.g., methods using TAQMAN®, MGB TAQMAN®; MGB is a trademark of Epoch Biosciences). For those methods utilizing TAQMAN® and MGB TAQMAN® the 5'-exonuclease activity of the approaching DNA Polymerase cleaves a probe between fluorophore and quencher thus releasing fluorescence. These types of probes are suitable for real-time DNA amplification detection. The first type of probes, however, can also be applied for post-amplification sequence detection (scatter plot analysis or thermal melt) or in a solid phase format. Solid phase immobilized quenched fluorescent probes have been disclosed in, for example, U.S. Pat. Nos. 5,876,930 and 6,596,490, and have been used to detect nucleic acid targets. The disclosed hybridization probes have either low signal to background ratios or slow hybridization rates (Xiaohong Fang et al. *J. Am. Chem. Soc.* 1999, 121: 2921-2922) and unstable, temperature dependent background fluorescence (fluorescence in unhybridized state), which makes them unsuitable for real-time amplification applications.

What is needed in the art are new oligonucleotide probes with high sequence specificity, improved sensitivity (signal to background ratio), stable (temperature independent) background signal and fast hybridization rates. It is also needed that the probes can be readily prepared with a variety of natural and unnatural nucleotides, fluorescent labels and in various lengths. The present invention provides such probes, as well as methods for their preparation and use.

BRIEF SUMMARY OF THE INVENTION

In one aspect, the present invention provides oligonucleotide-probes comprising an oligonucleotide portion having a 3'-end and a 5'-end, a minor groove binder moiety attached to at least one of said nucleotide units through a linking group which covalently binds the minor groove binder moiety to the oligonucleotide, and a fluorophore and quencher, said probe having the formula;

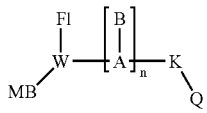

wherein MB is a minor groove binder; Q is a quencher; Fl is a fluorophore; $[A-B]_n$ represents an nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog; K is a bond or a linking group; and W is a trivalent linking group that provides sufficient spacing between MB, Fl and $[A-B]_n$ such that (i) MB binds in a duplex minor groove formed when said oligonucleotide probe hybridizes to its complementary sequence; (ii) in an unhybridized form, the fluorescence of Fl in said oligonucleotide probe is less than 10% of unquenched fluorescence; and (iii) when said oligonucleotide probe hybridizes to said target sequence, the fluorescence of Fl is at least 50% of its unquenched fluorescence.

In some embodiments, W provides spacing between MB, Fl and $[A-B]_n$ such that in an unhybridized form, the fluorescence of Fl in said oligonucleotide probe is less than about 10% of unquenched fluorescence. In other embodiments, W is a member selected from the group consisting of:

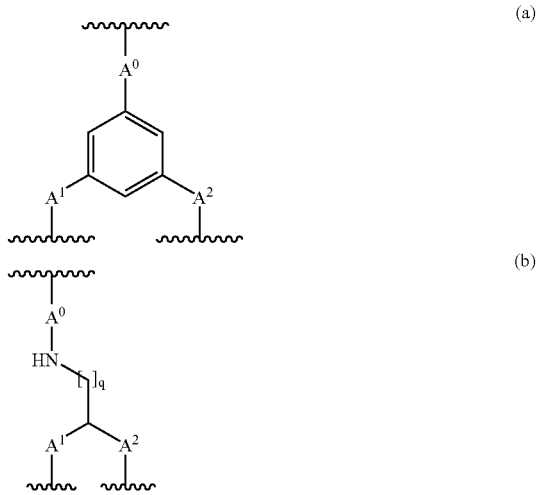

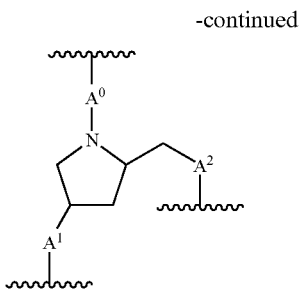

(c)

wherein the subscript q is an integer of from 0 to 8; and $A^0$, $A^1$ and $A^2$ are each linking groups (e.g., aryl, alkylene, substituted alkylene, heteroalkylene, substituted heteroalkylene and combinations thereof) having from 1 to 50 main chain atoms, and the wavy lines indicate the point of attachment to MB, Fl and the $[A-B]_n$ portion.

In still other embodiments, n is an integer of from 6 to 18, and said $[A-B]_n$ portion comprises at least three consecutive guanine nucleotides wherein at least one of the guanine nucleotide bases is replaced by PPG. Preferably, the $[A-B]_n$ portion is a DNA, RNA, chimera, a PNA or a locked nucleic acid. In yet other embodiments, n is an integer of from 6 to 18, said probe being complementary to a target sequence having at least 30% adenine and thymine bases, wherein said probe contains at least one modified base sufficient to provide an increase of stability of duplex formation of at least 3° C., relative to a probe without said at least one modified base. In certain embodiments, the probe is complementary to a target sequence having at least 50% adenine and thymine bases, wherein said probe contains sufficient modified bases to provide an increase of stability of duplex formation of at least 5° C., relative to a probe without said modified bases.

In related aspects, the present invention provides methods and arrays for using the probes described herein.

In one related aspect, the present invention provides methods for continuous monitoring of polynucleotide amplification, comprising:
(a) providing an array of oligonucleotide probes of different sequences,
(b) incubating a population of polynucleotides with the array under hybridization conditions, and
(c) determining to which of the oligonucleotide probes in the array the population hybridizes;

wherein one or more of the oligonucleotide probes is an oligonucleotide conjugate having the formula:

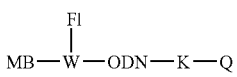

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence. In some preferred embodiments, the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, beuzoxanthenes, cyanines and BODIPY™ analogs, and said Q portion is a member selected from the group consisting of mono azo and bis azo dyes. In other preferred embodiments, the conjugates are attached to a solid support.

In another related aspect, the present invention provides methods for discriminating between polynucleotides which differ by a single nucleotide, the method comprising:
(a) separately incubating each of at least two polynucleotides with an oligonucleotide conjugate having the formula:

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence, said conjugate having a defined sequence under hybridization conditions, wherein one of the polynucleotides has a target sequence that is perfectly complementary to said oligonucleotide conjugate and at least one other of the polynucleotides has a target sequence having a single-nucleotide mismatch with the oligonucleotide conjugate; and
(b) determining the hybridization strength between each of the polynucleotides and the oligonucleotide conjugate. As above, certain preferred embodiments are those in which the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4] benzodiazepine analogs, said Fl portion is a fluorophore having an emission wavelength of from about 400 rim to about 800 rim, said fluorophore being selected from the group consisting of coumarins, resorufins, xanthenes, benzoxanthenes, cyanines and BODIPY™ analogs, and said Q portion is a member selected from the group consisting of mono azo and bis azo dyes.

In still another related aspect, the present invention provides methods for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising:

(a) contacting the mixture of polynucleotides with an oligonucleotide conjugate having the formula:

wherein MB is a minor groove binder, Q is a quencher, ODN is an oligonucleotide or modified oligonucleotide, K is a bond or a linking group, Fl is a fluorophore and W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence; and wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence of said target sequence. Preferred embodiments include those described above, particularly wherein the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and BODIPY™ analogs, and said Q portion is a member selected from the group consisting of mono azo and bis azo dyes.

In still another related aspect, the present invention provides methods for distinguishing between wild-type, mutant and heterozygous target polynucleotides, said method comprising:

(a) contacting a sample containing a target polynucleotide with two probes wherein a first probe is specific for said wild-type target polynucleotide and a second probe is specific for said mutant target polynucleotide, each of said probes having a formula:

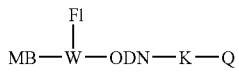

wherein MB is a minor groove binder, Q is a quencher, ODN is an oligonucleotide or modified oligonucleotide, K is a bond or a linking group, Fl is a fluorophore and W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence; and wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence or absence of each of said wild-type, mutant and heterozygous target polynucleotides. In this aspect, the melting temperatures ($T_m$) for each hybrid produced between said first and second probes and their respective targets are preferably within about 5° C. of each other. In other selected embodiments, the ODN portion of each of said probes is an oligonucleotide or modified oligonucleotide having from 8 to 18 bases or modified bases. Still more preferably, the ODN portion of each of said probes is an oligonucleotide or modified oligonucleotide having from 10 to 18 bases or modified bases. In other preferred embodiments, the fluorophore portions of each of said probes are selected from the group consisting of 5-FAM™, 6-FAM™, TET™, JOE™, HEX™, VIC™, NED™, TAMRA™, ROX™ and YY™, or alternatively is a phosphonate fluorophore as described in U.S. Provisional Application Ser. No. 60/601,599, incorporated herein by reference. In still other preferred embodiments, the ODN portion of each of said probes contains at least one modified base, preferably selected from 6-amino-1H-pyrazolo[3,4-d]pyrimidin-4(5H)-one, 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-yny)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine. In still other embodiments, the sample is further contacted with a set of primers under amplification conditions and each of said primers contains from one to ten modified bases selected from those described herein.

BRIEF DESCRIPTION OF THE DRAWINGS

FIG. 9a demonstrates the performance of the new probe conjugate of the invention where the wild-type probe is labeled with FAM and the mutant probe with YY. FIG. 9b demonstrates the performance of MGB ECLIPSE™ probes where the wild-type probe is labeled with FAM and the mutant probe with YY.

DETAILED DESCRIPTION OF THE INVENTION

Definitions and Abbreviations

Figure 1:
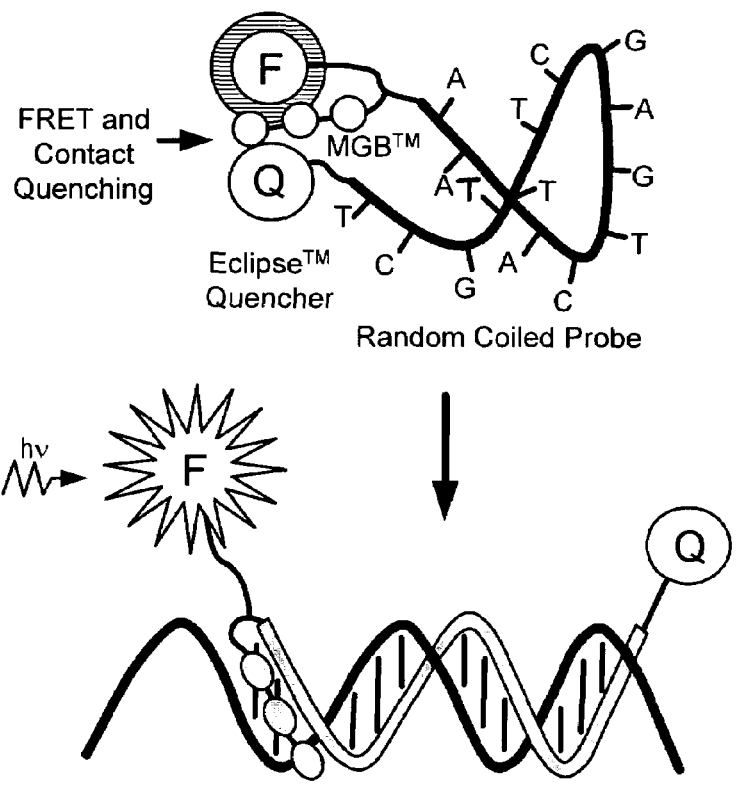
FIG. 1 is schematic representation of the probe of the invention (MB-Fl-ODN-Q; SEQ ID NO:1) that is solution quenched and hybridized to its complementary nucleic acid target where the fluorophore and quencher is spatially separated allowing fluorescence.

In the reaction schemes and description below (and above), the abbreviations MB, FL, Q, CPG and ODN refer to "minor groove binder", "fluorescent label" or "fluorophor", "quencher", "controlled pore glass" (as an example of a solid support) and "oligonucleotide" moieties or molecules, respectively, and in a manner which is apparent from context. In certain formulae, the group $[A-B]_n$ is used to refer to an oligonucleotide, modified oligonucleotide or peptide-nucleic acid having 'n' bases (B) and being linked along a backbone of 'n' sugars, modified sugars or amino acids (A). The terms "probe" and "conjugate" are used interchangeably and refer to an oligonucleotide having an attached minor groove binder, fluorophore and quencher.

The terms "fluorescent label" or "fluorophore" refers to compounds with a fluorescent emission maximum between about 400 and 900 nm. These compounds include, with their emission maxima in nm in brackets, Cy2™ (506), GFP (Red Shifted) (507), YO-PRO™-1(509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO-1 (533), TOTO®-1 (533), JOE (548), BODIPY® 530/550 (550), DiI (565), BODIPY® TMR (568), BODIPY® 558/568 (568), BODIPY® 564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO™-3 (631), R-phycocyanin (642), C-Phycocyanin (648), TO-PRO™-3 (660), TOTO®-3 (660), DiD DilC(5) (665), Cy5™ (670), Thiadicarbocyanine (671), Cy5.5 (694). Additional fluorophores are disclosed in PCT publication WO 03/023357 and U.S. Provisional application Ser. No. 60/601,599, incorporated by reference in their entireties.

The term "linker" refers to a moiety that is used to assemble various portions of the molecule or to covalently attach the molecule (or portions thereof) to a solid support. Additionally, a linker can include linear or acyclic portions, cyclic portions, aromatic rings or combinations thereof.

The term "reactive group" refers to a moiety that has at least one nucleophilic group or at least one electrophilic (reactive) group. In some instances a "reactive group" may contain both groups, but in these instances one or both of the groups is typically blocked by a protecting group to control undesired reaction (See T. W. Greene and P. G. Wuts, below). Examples of nucleophilic groups include —NH$_2$, —NHNH$_2$, —ONH$_2$, —NHC═(O)NHNH$_2$, —OH, or —SH. Examples of electrophilic reactive groups include activated esters, acrylamides, acyl azides, acyl halides, aldehyde or ketones, alkyl halides, alkyl sulfonates, anhydrides, aryl halides, aziridines, boronates, carboxylic acids, carbodiimides, diazoalkanes, epoxides, haloacetamides, halotriazines, imidoesters, isocyanates, isothiocyanates, maleimides, phosphoramidites, silyl halides, sulfonate ester and sulfonyl halides.

The term "solid support" refers to any support that is compatible with oligonucleotides synthesis or suitable for hybridization assays (such as DNA arrays), including, for example, glass, controlled pore glass, polymeric materials, polystyrene, beads, coated glass and the like.

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of main chain carbon atoms in an alkyl portion, the radical or portion thereof will have eight or fewer main chain carbon atoms. The term "heteroalkyl" refers to a linear, branched, or cyclic saturated monovalent radical or a combination of cyclic and linear or branched saturated monovalent radicals having the number of carbon atoms indicated in the prefix and from one to three heteroatoms in place of carbon atoms.

The term "alkylene" means a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like. The term "heteroalkylene" refers to an alkylene group having the indicated number of carbon atoms in a chain which is interrupted by from 1 to 5 heteroatoms (e.g., O, N, S, P and Si).

The term "alkenyl" refers to a linear monovalent hydrocarbon radical or a branched monovalent hydrocarbon radical having the number of carbon atoms indicated in the prefix and containing at least one double bond. For example, $(C_2-C_6)$alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, $(C_2-C_6)$alkynyl is meant to include ethynyl, propynyl, and the like.

Substituents, when present for the alkyl, alkenyl, alkynyl, alkylene and heteroalkylene groups are varied and are selected from: -halogen, oxo, thiono, —OR', —OC(O)R', —NR'R", —SR', —R', —CN, —NO$_2$, —CO$_2$R', —CONR'R", —C(O)R', —OC(O)NR'R", —NR"C(O)R', —NR'-C(O)$_2$R', —NR'-C(O)NR"R''', —S(O)R', —S(O)$_2$R', —S(O)$_2$NR'R", perfluoro$(C_1-C_4)$alkoxy, and perfluoro$(C_1-C_4)$alkyl, in a number ranging from one to four; and where R', R" and R''' are independently selected from hydrogen, $(C_1-C_8)$alkyl and heteroalkyl, unsubstituted aryl and heteroaryl, (unsubstituted aryl)-$(C_1-C_4)$alkyl, and (unsubstituted aryl)oxy-$(C_1-C_4)$alkyl.

The term "aryl" means a monovalent or bivalent (e.g., arylene) monocyclic, bicyclic or tricyclic aromatic hydrocarbon radical of 6 to 14 ring atoms which is unsubstituted or substituted independently with one to six substituents, preferably one, two, or three substituents selected from those groups provided below. The term "aryl" is also meant to include those groups described above wherein one or more heteroatoms or heteroatom functional groups have replaced a ring carbon, while retaining aromatic properties, e.g., pyridyl, quinolinyl, quinazolinyl, thienyl, and the like. More specifically the term aryl includes, but is not limited to, phenyl, 1-naphthyl, 2-naphthyl, thienyl and benzothiazolyl, acridinyl and the substituted forms thereof.

Substituents for the aryl groups are varied and are selected from: -halogen, —OR', —OC(O)R', —NR'R", —SR', —R', —CN, —NO$_2$, —CO$_2$R', —CONR'R", —C(O)R', —OC(O) NR'R", —NR"C(O)R', —NR"C(O)$_2$R', —NR'—C(O) NR"R''', —NH—C(NH$_2$)=NH, —NR'C(NH$_2$)=NH, —NH—C(NH$_2$)=NR', —S(O)R', —S(O)$_2$R', —S(O)$_2$ NR'R", —N$_3$, —CH(Ph)$_2$, perfluoro$(C_1-C_4)$alkoxy, and perfluoro$(C_1-C_4)$alkyl, in a number ranging from zero to the total number of open valences on the aromatic ring system; and where R', R" and R''' are independently selected from hydrogen, $(C_1-C_8)$alkyl and heteroalkyl, unsubstituted aryl and heteroaryl, (unsubstituted aryl)-$(C_1-C_4)$alkyl, and (unsubstituted aryl)oxy-$(C_1-C_4)$alkyl.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $(C_1-C_6)$alkyl. Still further, one of the aryl rings (Ar$^1$ and Ar$^2$, below) can be further substituted with another substituted aryl group to extend the resonance ability of the aromatic system, directly or indirectly through groups such as —(CR'=CR')$_n$- and —(C≡C)$_n$—, where n is 0 to 5, increasing the wavelength absorbance maximum.

The prefix "halo" and the term "halogen" when used to describe a substituent, refer to —F, —Cl, —Br and —I.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of "Advanced Organic Chemistry", 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not (e.g, $^2H$), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Wuts, Protective Groups in Organic Chemistry, (Wiley, 2nd ed. 1991) and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (Fmoc), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. In general, the preferred protecting groups are those that can be removed under acidic conditions or basic conditions, or those groups that can be removed by the use of a particular light source (e.g., "light sensitive" protecting groups). Additionally, selection of an appropriate protecting group is made with due consideration to other functionality in the molecule so that either the incorporation or removal of the protecting group does not interfere or otherwise significantly affect the remainder of the molecule.

"Optional" or "optionally" in the above definitions means that the subsequently described event or circumstance may but need not occur, and that the description includes instances where the event or circumstance occurs and instances in which it does not. For example, "aryl optionally mono- or di-substituted with an alkyl group" means that the alkyl group may, but need not, be present, and the description includes situations where the aryl group is mono- or disubstituted with an alkyl group and situations where the aryl group is not substituted with the alkyl group.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

The term "ECLIPSE™ probe" refers, in general, to a MB-Q-5'-ODN-Fl probe. The MB ligand is dihydropyrroloindole-carboxylic acid triamide. In contrast, a TAQMAN® and MGB™ probe refers to a MB-Q-3'-ODN-Fl probe. ECLIPSE™ and MGB™ are trademarks of Epoch Biosciences, Inc., Bothell, Wash.; and TAQMAN® is a registered trademark of Applied Biosystems, Inc., Foster City, Calif.

General

Figure 3:
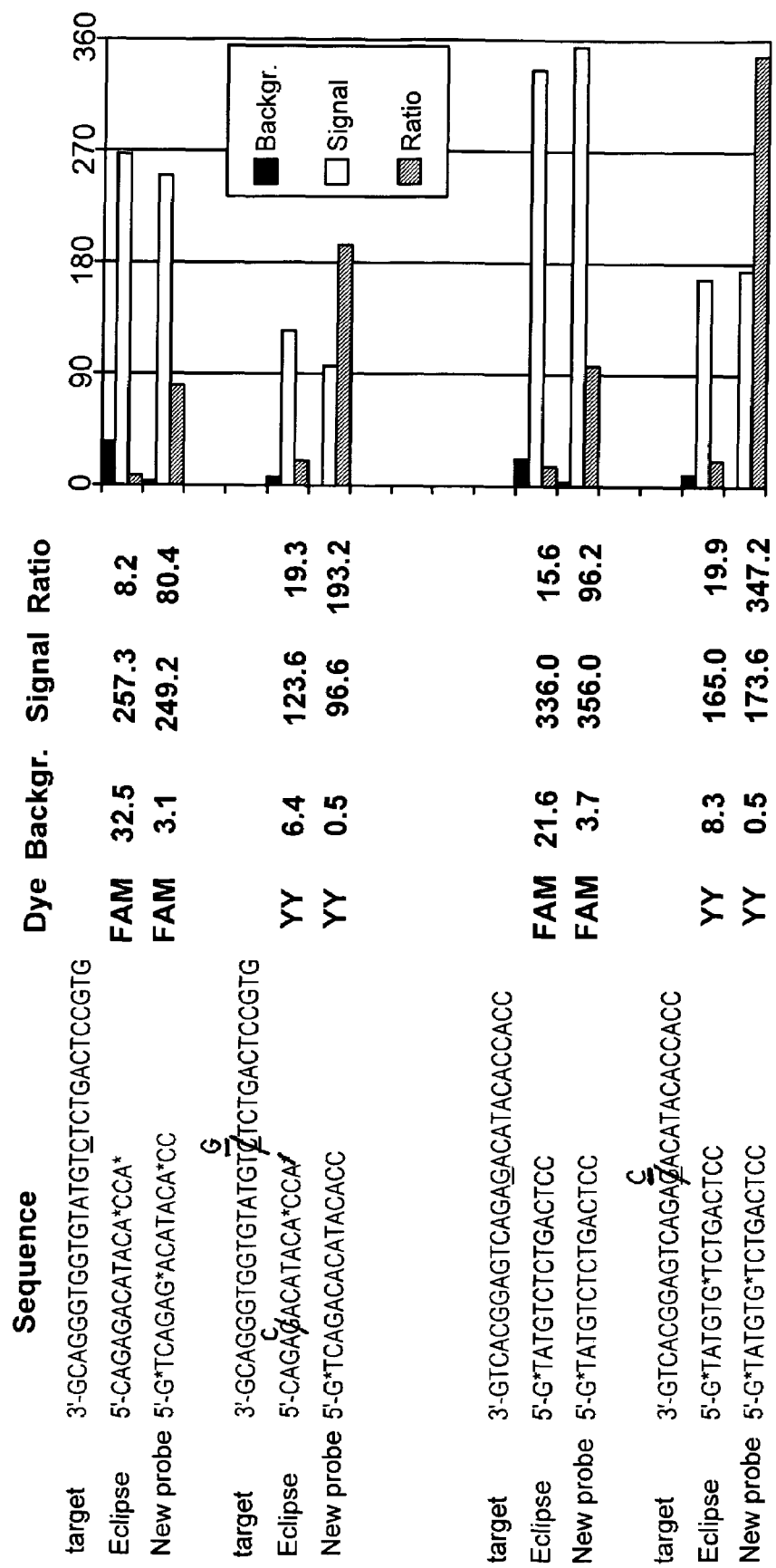

Minor groove binder oligonucleotide conjugates (or "probes") have recently been described (see WO 99/51621). These conjugates form hyper-stabilized duplexes with complementary DNA. In particular, sequence specificity of short MB probes is excellent for high temperature applications such as PCR. The 5'-Minor Groove Binder-quencher-oligonucleotide-fluorophore (MB-Q-5'-ODN-Fl) probes disclosed in WO 03/062445 displayed a dynamic range of 7 orders of magnitude, with an ultimate sensitivity of better than 5 copies per sample in real-time PCR amplification reactions. Quite surprisingly, probes containing a minor groove binding-fluorophore group at one end and a quencher at the other end show improved sensitivity and significantly reduced background signal (fluorescence of unhybridized probe) compared to the probes of WO 03/062445 and are particularly useful for assay methods using fluorogenic 2'-ribodeoxynucleotides. These probes fluoresce upon hybridization to the complementary target as illustrated in FIG. 1 with background signal 10-50 times lower than for probes disclosed in WO 03/062445 (FIG. 3). In addition the probes of invention have significantly more stable (temperature independent) background signal compare to the probes disclosed in WO 03/062445 (see FIG. 4). This property is particularly useful for application that involve melting profile analysis such as post PCR single nucleotide polymorphism analysis.

Figure 2:
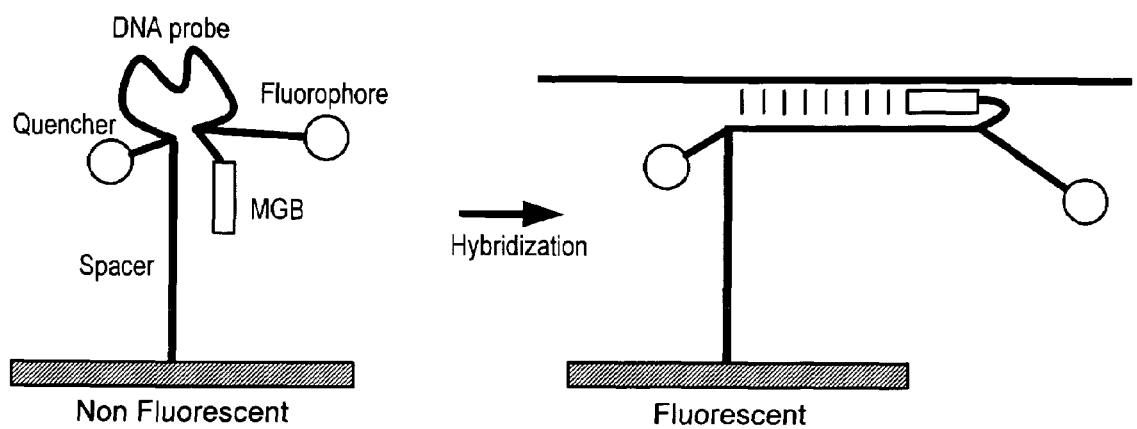
FIG. 2 illustrates an immobilized probe of the invention (MB-Fl-ODN-Q) immobilized to a solid support. The unhybridized probe's fluorescence is efficiently quenched. Quencher (Q) and Fluorophore (Fl) are in close proximity. On hybridization of the probe to its complementary nucleic acid target, the Q and Fl are spatially separated resulting in fluorescence. MB ligand is a minor groove binder that binds in the minor groove of the duplex resulting in its stabilization FIG. 3 compares the fluorescent signal, fluorescent background and signal to background of four probes of the invention (SEQ ID NOS: 4, 7, 9 and 11) with that of four MGB ECLIPSE™ probes (SEQ ID NOS:3, 6, 9 and 11) hybridized to four different targets (SEQ ID NOS:2,5, 8 and 10).

The 5'-MB-quencher group has previously been found to prevent 5'-nuclease digestion by Taq polymerase during homogeneous amplification. The new probes have similar 5'-nuclease resistance when MB-Fl- is attached at the 5'end. Therefore, the new probes can be used in assays where 5'-nuclease resistance is essential. 3'-MB-Fl probes can be used in assays, which require partial or complete degradation of the probe for signal generation, such as TAQMAN®. Both 5'- and 3'-MB-Fl-ODN-Q can also be used in non-real-time/post PCR assays. Solid-phase-based assays (such as DNA arrays) are still other applications for the probes of the present invention (FIG. 2).

The MB-Fl-ODN-Q probe/conjugates of the present invention are constructed such that the probe exists in at least one single-stranded conformation when unhybridized. In the unhybridized random coil form the quencher and MB are near enough to the fluorophore to quench the fluorescence of the fluorophore. The probes also constructed in such a way that both minor groove binder (FIG. 5a) and quencher (FIG. 5b) participate in fluorescence quenching.

When hybridized to a target polynucleotide, the probes/conjugates adopt a conformation such that the MB is concealed in the DNA minor groove and quencher is not positioned close enough to the fluorophore to quench its fluorescence. By adopting these hybridized and unhybridized conformations, the probe exhibit substantially different fluorescence signal intensities when the probe is hybridized and unhybridized. As a result, it is possible to determine whether the probe is hybridized or unhybridized based on a change in the fluorescence intensity of the probe, and the use of such probes allow target detection of nucleic acid targets in homogeneous (such as PCR amplification reaction) or non-homogeneous (DNA arrays) assays.

The minor groove binder-fluorophore-oligonucleotide-quencher conjugates of the present invention can be in a linear arrangement (as suggested by the formula MB-Fl-ODN-Q or in a branched arrangement wherein the fluorophore and the minor groove binder are attached to a linking group that serves to join ODN, Fl and MB. Each of the arrangements is meant to be included when the linear abbreviation (MB-Fl-ODN-Q) is used. Additionally, while the MB and Fl portions are attached at one end of the oligonucleotide, the quencher portion can be attached at the other end, or an internal position of the oligonucleotide, so long as such attachment does not interfere with the quenching mechanisms of the conjugate. Generally, this can be accomplished through the use of a suitable linking group (see Examples below) or base linkers such as 5-aminopropyluridine. As a result, the present invention provides a number of preferred embodiments in which linkages between ODN and Q are selected to provide suitable separation distances between the quencher and fluorophore moieties, while not compromising the hybridization capabilities of the oligonucleotide portion.

As noted above, the conjugates (or probes) of the present invention are useful in a variety of hybridization-based detection assays, but find particular utility in "real-time" detection of oligonucleotide amplification, often conducted via PCR. Additionally, the probes and conjugates of the present invention are useful in post amplification detection of target oligonucleotides.

DESCRIPTION OF THE EMBODIMENTS

Probes and Conjugates

In view of the above, the present invention provides in one aspect oligonucleotide probes (or oligonucleotide conjugates, hereinafter "probes/conjugates", "probes" or "conjugates") which are most generally noted as MB-Fl-ODN-Q probes or conjugates. As noted above, this linear depiction of the probes is meant to indicate that a minor groove binder and fluorophore or emission agent are attached to one end of the oligonucleotide portion, and a quencher is attached to the other end of the oligonucleotide portion. For any of these covalently attached portions, connection can be either direct or via a linking group. In many embodiments, linking groups are preferred to provide sufficient spacing between interactive portions (e.g., fluorophore and quencher) or reactive portions (e.g., minor groove binders that are meant to bind non-covalently in the minor groove formed by probe hybridization to a target sequence).

While most of the components described herein for the probes or conjugates have been described in related applications (see, for example, U.S. Pat. Nos. 6,339,147, 6,486,303, and 6,472,153; and PCT publications WO 01/64958 and WO 03/062445), the order of assembly and the linking groups utilized to achieve the beneficial effects for the present invention set forth new criteria for spatial relationships and flexibility.

Accordingly, in one group of embodiments, the MB-Fl-ODN-Q probe or conjugate has the formula:

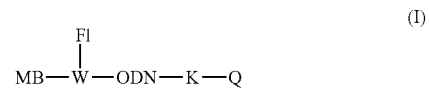

(I)

wherein MB is a minor groove binder, Q is a quencher, W is a trivalent linking group, ODN is an oligonucleotide or modified oligonucleotide, K is a bond or a linking group and Fl is a fluorophore.

More particularly, when K is a linking group, it will generally have from 1 to 50 main chain atoms (counting only those atoms between the ODN component and the Q component that are joined in a continuous line, including all ring atoms, but not including any pendant atoms or groups) that are selected from C, O, N, S, P and Si. The linking group W will generally represent a trivalent linker having from about 3 to 100 main chain atoms, selected from C, O, N, S, P and Si. Additionally, W can contain a branched aliphatic chain, a heteroalkyl chain, one or more substituted ring structures, or combinations thereof. In some embodiments, W represents a trifunctional moiety such as an amino group with or without pendent functionalized linking groups. Accordingly, while W is provided as a linking group, it will in some embodiments be a group that may be considered a part of Fl. Each of the linking groups, as well as other components, will be discussed in more detail below.

In a group of further preferred embodiments, the oligonucleotide probe/conjugate has the formula:

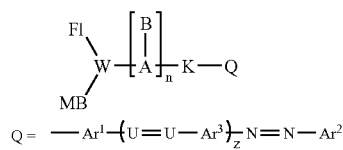

(II)

$Q = -Ar^1-(U=U-Ar^3)_z-N=N-Ar^2$ in which MB, W, K and Fl have the meanings provided above, [A-B]$_n$ represents a nucleic acid oligomer (e.g., DNA, RNA, PNA or any combination thereof, including those with modified bases and sugars), wherein A represents a sugar phoshpate backbone, modified sugar phosphate backbone, locked nucleic acid backbone, peptidic backbone or a variant thereof used in nucleic acid preparation; and B represents a nucleic acid base, a modified base or a base analog as described in more detail below. The subscript n is an integer of from about 3 to about 100, preferably 6 to about 50 and more preferably 8 to about 25.

Returning to formula II, symbol Q has the formula Ar$^1$—(U=U—Ar$^3$)$_n$—N=N—Ar$^2$. The symbols Ar$^1$, Ar$^2$ and Ar$^3$ represent aryl groups. Q has at least one strong electron-donating group, such as alkoxy, hydroxy, amino, alkylamino, dialkylamino, arylamino and the like, and at least one strong electron-withdrawing group such as nitro, cyano, carbonyl, carboxy, sulfonyl, trifluoromethyl and the like. Ar$^1$, Ar$^2$ and Ar$^3$ can additionally be substituted with alkyl, cyclic alkyl, aryl, substituted aryl, halogen. The subscript z is an integer of 0 or 1, preferably 0. When z is 1, U is independently selected from CH, C(R) and N, in which R is a (C$_1$-C$_8$)alkyl group. K is connected with one of Ar$^1$, Ar$^2$ or Ar$^3$ either directly or via substituents. Preferred aryl groups for each of Ar$^1$, Ar$^2$ and Ar$^3$ are phenyl groups.

In still further preferred embodiments, the oligonucleotide probe/conjugate has the formula:

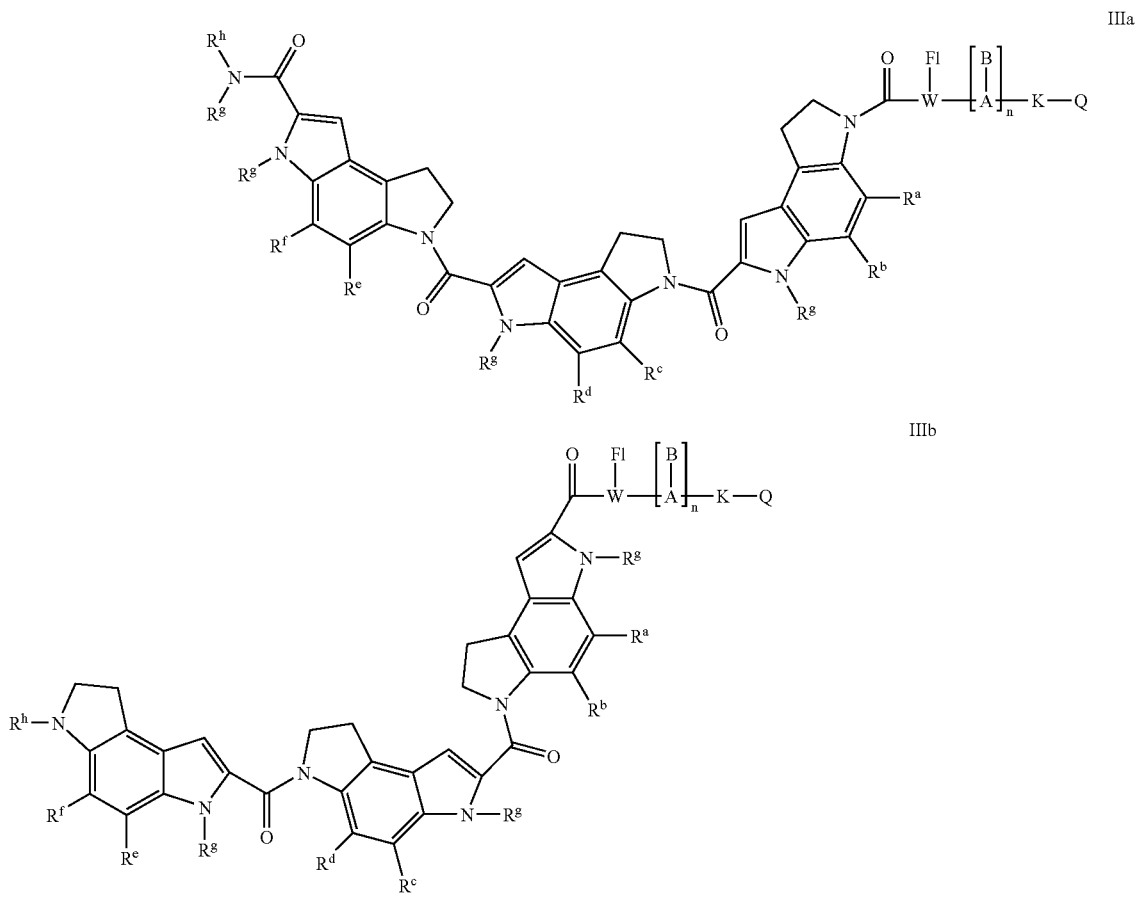

in which Ar$^1$, Ar$^2$, W, K, Fl, A, B and the subscript n have the meanings provided above, and wherein the symbols R$^a$, R$^b$, R$^c$, R$^d$, R$^e$ and R$^f$ represent substituents selected from H, halogen, (C$_1$-C$_8$)alkyl, OR$^g$, N(R$^g$)$_2$, N$^+$(R$^g$)$_3$, SR$^g$, COR$^g$, CO$_2$R$^g$, CON(R$^g$)$_2$, (CH$_2$)$_{0-6}$SO$_3^-$, (CH$_2$)$_{0-6}$CO$_2^-$, (CH$_2$)$_{0-6}$OPO$_3^{-2}$, and NHC(O)(CH$_2$)$_{0-6}$CO$_2^-$, and esters and salts thereof, wherein each R$^g$ is independently H or (C$_1$-C$_8$)alkyl. The symbol R$^h$ represents H or a group (typically the vestige of a linking group used in solid phase synthesis) having from 1-30 atoms selected from C, N, O, P, and S which is either cyclic, acyclic, or a combination thereof, and having additional hydrogen atoms to fill the available valences. The symbol Q has the meaning provided above.

In still further preferred embodiments, the oligonucleotide probe/conjugate has the formula:

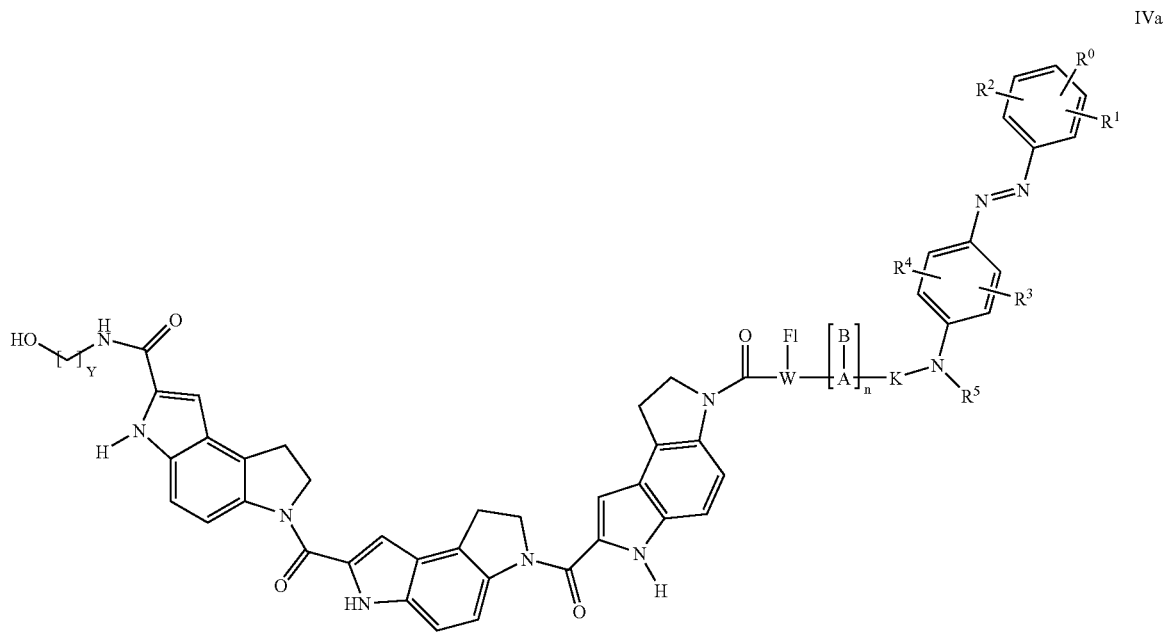

IVa in which W, K, Fl, A, B have the meanings provided above, and wherein at least one of the symbols $R^0$, $R^1$ and $R^2$ represent electron-withdrawing group; $R^3$ and $R^4$ represent H or halogen, alkyl, oxyalkyl, alkyloxy; symbol $R^5$ represents alkyl or hydroxyalkyl, and the subscript n is an integer of from 1 to 20. In a particularly preferred embodiment, $R^0=NO_2$; $R^1=Cl$; $R^2=R^3=R^4=H$; $R^5=CH_3$; and Y=5.

In a particularly preferred group of embodiments, the linkers W and K have the formulae:

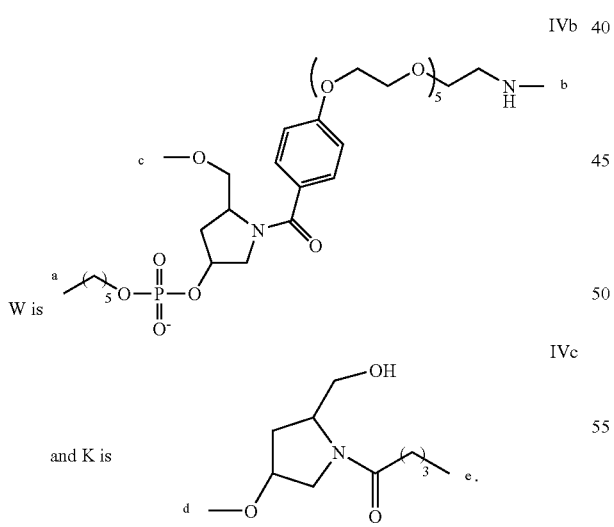

wherein a, b, c, d and e are attachment points for the MB ligand, fluorophore, ODN termini ends and quencher, respectively.

In certain preferred embodiments for each of the above groups, K and W are selected to provide particular fluorescence enhancement for the probe/conjugate, and will depend on the length of the oligonucleotide portion of the probe. Accordingly, for probes having 18 or more nucleotides (including modified nucleotides or analogs), K can be a bond or a linking group up to about 20 atoms in length. More preferably, K is a prolinol group. In particularly preferred embodiments, K is a substituted prolinol linker such as IVc. For oligonucleotide conjugates having fewer than about 18 nucleotides (including modified nucleotides or analogs), longer K groups are preferred (e.g., 15, 20, 30, 40 or more main chain atoms).

As provided in formula I, the letter W represents a trifunctional linking group. Accordingly, for probes having 5 or more nucleotides (including modified nucleotides or analogs), W can encompass a variety of structures in order to provide suitable attachment, flexibility and spacing between the ODN, Fl and MB. W can be a linking group up to about 100 atoms in length selected from C, N, S, P, Si and O, and additional hydrogen atoms to fill the available valences (discussed in more detail below).

Other preferred probes or conjugates are those in each of formulae I, II, IIIa and IIIb, and IV wherein the ODN portion is selected to have three or more consecutive guanine bases wherein at least one of the guanine bases is replaced with a modified base, preferably PPG. Still more preferably, the ODN portion is a RNA, a chimera, a PNA or a locked nucleic acid.

Still other preferred probes or conjugates are those in each of formulae I, II, IIIa and IIIb, and IV wherein the ODN portion is selected to be complementary to a target sequence having 30% or more A and T bases, wherein the ODN contains at least one modified base sufficient to provide an increase in stability of the duplex (probe/target hybrid) of at least about 3° C. More preferably, the ODN portion is selected to be complementary to a target sequence having 50% or more A and T bases, wherein the ODN contains sufficient modified bases to provide an increase in stability of the duplex (probe/target hybrid) of at least about 5° C. Still more preferably, the ODN portion is a DNA, a RNA, a chimera, a PNA or a locked nucleic acid.

The probes and conjugates of the present invention are generally prepared using solid phase methods known to those of skill in the art. Assembly can be carried out in either the 5' to 3' direction, or the 3' to 5' direction, using, for example, appropriate phosphoramidite reagents for coupling the ODN monomers, the fluorophores, quenchers and minor groove binders. Other methods for assembly include well known functional group condensations to prepare, for example, ester linkages, amide linkages, disulfide linkages, ether linkages, thioether linkages, and the like. In general, the starting materials are commercially available, or can be prepared in a straightforward manner from commercially available starting materials, using suitable functional group manipulations as described in, for example, March, et al., ADVANCED ORGANIC CHEMISTRY—Reactions, Mechanisms and Structures, 4th ed., John Wiley & Sons, New York, N.Y., (1992).

Returning to the more general provisions for the probes/conjugates of the present invention, the discussion below illustrates the types of oligonucleotides, quenching agents or quenchers, minor groove binders, fluorophores and linking groups that can be used herein.

Oligonucleotides and Modified Oligonucleotides

The terms oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids which are disclosed by Nielsen et al. *Science* 254:1497-1500 (1991); bicyclo DNA oligomers (Bolli et al., *Nucleic Acids Res.* 24:4660-4667 (1996)) and related structures. In one embodiment of the conjugates of the present invention, a MB moiety and a fluorophore are attached at the 5' end of the oligomer and a quenching agent is attached at the 3' end.

Preferred in the present invention are DNA oligonucleotides that are single-stranded and have a length of 100 nucleotides or less, more preferably 50 nucleotides or less, still more preferably 30 nucleotides or less and most preferably 20 nucleotides or less with a lower limit being approximately 5 nucleotides.

Oligonucleotide conjugates containing a fluorophore/quencher pair with a minor groove binder may also comprise one or more modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7-deazapurines and their derivatives and pyrazolopyrimidines (described in PCT WO 90/14353); and also described in U.S. Pat. No. 6,127,121. Universal and indiscriminative bases are described in co-pending application 60/508,792 (Incorporate by reference in its entirety).

The most preferred modified bases for use in the present invention include the guanine analogue 6-amino-1H-pyrazolo[3,4-d]pyrimidin-4(5H)-one (ppG or PPG, also Super G) and the adenine analogue 4-amino-1H-pyrazolo[3,4-d] pyrimidine (ppA or PPA). The xanthine analogue 1H-pyrazolo[5,4-d]pyrimidin-4(5H)-6(7H)-dione (ppX) can also be used. 3-prop-1-ynylpyrazolo[3,4-d]pyrimidine-4,6-diamino, (NH$_2$)$_2$PPPA represents another preferred modified base for use in the present invention. These base analogues, when present in an oligonucleotide, strengthen hybridization and improve mismatch discrimination. All tautomeric forms of naturally-occurring bases, modified bases and base analogues may be included in the oligonucleotide conjugates of the invention. Other modified bases useful in the present invention include 6-amino-3-prop-1-ynyl-5-hydropyrazolo [3,4-d]pyrimidine-4-one, PPPG; 6-amino-3-(3-hydroxyprop-1-yny)1-5-hydropyrazolo[3,4-d]pyrimidine-4-one, HOPPPG; 6-amino-3-(3-aminoprop-1-ynyl)-5-hydropyrazolo[3,4-d]pyrimidine-4-one, NH$_2$PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl)pyrazolo[3,4-d]pyrimidine, NH$_2$PPPA; 3-prop-1-ynylpyrazolo[3,4-d]pyrimidine-4,6-diamino, (NH$_2$)$_2$PPPA; 2-(4,6-diaminopyrazolo[3,4-d]pyrimidin-3-yl)ethyn-1-ol, (NH$_2$)$_2$PPPAOH; 3-(2-aminoethynyl)pyrazolo[3,4-d]pyrimidine-4,6-diamine, (NH$_2$)$_2$PPPANH$_2$; 5-prop-1-ynyl-1,3-dihydropyrimidine-2, 4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, NH$_2$PC; 5-[4-amino-3-(3-methoxyprop-1-ynyl)pyrazol[3,4-d]pyrimidinyl]-2-(hydroxymethyl)oxolan-3-ol, CH$_3$OPPPA; 6-amino-1-[4-hydroxy-5-(hydroxymethyl)oxolan-2-yl]-3-(3-methoxyprop-1-ynyl)-5-hydropyrazolo[3,4-d]pyrimidin-4-one, CH$_3$OPPPG; 4,(4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo[3,4-d] pyrimidin-4-one; 5-(4-hydroxy-but-1-ynyl)-1H-pyrimidine-2,4-dione, Super T; 3-iodo-1H-pyrazolo[3,4-d]pyrimidine-4,6-diamine ((NH$_2$)$_2$PPAI); 3-bromo-1H-pyrazolo[3,4-d]pyrimidine-4,6-diamine ((NH$_2$)$_2$PPABr); 3-chloro-1H-pyrazolo[3,4-d]pyrimidine-4,6-diamine ((NH$_2$)$_2$PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl). In some embodiments, the modified base noted above may also include universal bases. The universal base may include those disclosed by Loakes, *Nucl. Acids Res.*, 29: 2437-2447 (2001); Wu et al, *JACS*, 22: 7621-7632 (2000) and Seela et al, *Nucl. Acids Res.*, 28: 3224-3232 (2001), incorporated by reference.

In other group of preferred embodiments, modified bases are used to introduce the ligands directly or indirectly into the probe using one of the phosphoramides having the formulae V and VI:

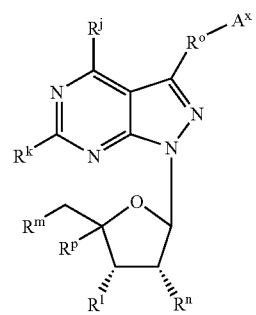

V

VI

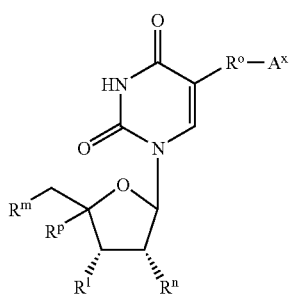

wherein $A^x$ is ligand selected from a group that includes fluorophores, quenchers or minor groove binders. $R^j$ and $R^k$ are each independently selected from the group consisting of H, $NH_2$ and a protected amino group; $R^n$ is a member selected from the group consisting of H, F and $OR^{m1}$ wherein $R^{m1}$ is a member selected from the group consisting of H, $(C_1-C_8)$alkyl and a hydroxy protecting group; $R^p$ is a member selected from the group of H, $(C_1-C_8)$alkyl, or is optionally combined with $R^n$ to form a five- to seven-membered ring, having from one to three heteroatoms selected from the group consisting of O, S and N; $R^1$ is a member selected from the group consisting of OH, a protected hydroxy group and O—$P^1$, wherein $P^1$ is a phosphoramidite or H-phosphonate group; $R^m$ is a member selected from the group consisting of OH, a protected hydroxy group and O—$P^2$, wherein $P^2$ is a phosphoramidite, H-phosphonate, monophosphate, diphosphate or triphosphate; $R^o$ is a linker with about 2 to 30 main atoms, selected from C, H, N, O, S and P, and can contain alkyl, alkylene, alkenyl, alkynyl and aryl groups alone or in combination.

In addition to the modified bases noted above, the oligonucleotides of the invention can have a backbone of sugar or glycosidic moieties, preferably 2-deoxyribofuranosides wherein all internucleotide linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. *Nucleic Acids Res.* 23:2661-2668 (1995). Synthetic procedures for locked nucleic acids (Singh et al, *Chem. Comm.*, 455-456 (1998); Wengel J., *Acc. Chem. Res.*, 32:301-310 (1998)) and oligonucleotides containing 2'-halogen-2'-deoxyribofuranosides (Palissa et al., *Z. Chem.* 27:216 (1987)) have also been described. The phosphate backbone of the modified oligonucleotides described herein can also be modified so that the oligonucleotides contain phosphorothioate linkages and/or methylphosphonates and/or phosphoroamidates (Chen et al., *Nucl. Acids Res.*, 23:2662-2668 (1995)). Combinations of oligonucleotide linkages are also within the scope of the present invention. Still other backbone modifications are known to those of skill in the art.

In another group of embodiments, the modified bases described herein are incorporated into PNA and DNA/PNA chimeras to balance $T_m$s and provide modified oligonucleotides having improved mismatch discrimination. Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. *Science* 254:1497-1500 (1991). PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized. Uhlmann et al. *Angew. Chem. Int. Ed.* 37:2796-2823 (1998). Accordingly, the use of any combination of normal bases, unsubstituted pyrazolo[3,4-d]pyrimidine bases (e.g., PPG and PPA), 3-substituted pyrazolo[3,4-d] pyrimidines, modified purine, modified pyrimidine, 5-substituted pyrimidines, universaldiscriminative bases, sugar modification, backbone modification or a minor groove binder to balance the $T_m$ of a DNA, PNA or DNA/PNA chimera is in the scope of this invention. The synthetic methods necessary for the synthesis of modified base monomeric units required for nucleic acid, PNA and PNA/DNA chimeras synthesis are available in the art, see methods in this application and Uhlmann et al. *Angew. Chem. Int. Ed.* 37:2796-2823 (1998).

For the uses described herein, and as noted above, the oligonucleotides and modified oligonucleotides will preferably have from 5 to 100 bases, more preferably from 5 to 50 bases, still more preferably, 5 to 30 bases, and even more preferably, 5 to 20 bases. In some embodiments, the oligonucleotide portions of the probes/conjugates will have 5 to 15 bases. In some embodiments, the oligonucleotide portions will have 6, 7, 8, 9, 10, 11, 12, 13 or 14 bases or modified bases.

The ability to design probes and primers in a predictable manner using an algorithm, that can direct the use or incorporation of modified bases, minor groove binders, fluorphores and/or quenchers, based on their thermodynamic properties have been described in co-pending application Ser. No. 10/032,307, filed Dec. 21, 2001. Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal/discriminative bases, sugar modification, backbone modification or a minor groove binder to balance the $T_m$ (e.g., within about 5-8° C.) of a hybridized product with a nucleic acid, PNA or DNA/PNA chimera is contemplated by the present invention.

Minor Groove Binders

The probes/conjugates of the present invention will also have a covalently attached minor groove binder (MB). A variety of suitable minor groove binders have been described in the literature. See, for example, Kutyavin, et al. U.S. Pat. No. 5,801,155; Wemmer, D. E., and Dervan P. B., *Current Opinon in Structural Biology*, 7:355-361 (1997); Walker, W. L., Kopka, J. L. and Goodsell, D. S., *Biopolymers*, 44:323-334 (1997); Zimmer, C & Wahnert, U. *Prog. Biophys. Molec. Bio.* 47:31-112 (1986) and Reddy, B. S. P., Dondhi, S. M., and Lown, J. W., *Pharmacol. Therap.*, 84:1-111 (1999).

Suitable methods for attaching minor groove binders (as well as reporter groups such as fluorophores and quenchers described below) through linkers to oligonucleotides are described in, for example, U.S. Pat. Nos. RE 38,416; 5,512,677; 5,419,966; 5,696,251; 5,585,481; 5,942,610 and 5,736,626.

The MB is generally attached either to an internal base (U.S. Pat. Nos. RE 38,416 and 6,084,102), the 5' or 3' end of the oligonucleotide portion via a suitable linking group. Attachment at the 5' end not only provides a benefit of hybrid stability but also inhibits nuclease digestion of the probe during amplification reactions.

The location of a MB within a MB-oligonucleotide conjugate can also affect the discriminatory properties of such a conjugate. An unpaired region within a duplex will result in changes in the shape of the minor groove in the vicinity of the mispaired base(s). Since MBs fit best within the minor groove of a perfectly-matched DNA duplex, mismatches resulting in shape changes in the minor groove would reduce binding strength of a MB to a region containing a mismatch. Hence, the ability of a MB to stabilize such a hybrid would be decreased, thereby increasing the ability of a MB-oligonucleotide conjugate to discriminate a mismatch from a perfectly-matched duplex. On the other hand, if a mismatch lies outside of the region complementary to a MB-oligonucleotide conjugate, discriminatory ability for unconjugated and MB-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of MB-oligonucleotides conjugates in this context lies in the fact that much shorter oligonucleotides compared to those used in the prior art (i.e., 20-mers or shorter), having greater discriminatory powers, can be used, due to the pronounced stabilizing effect of MB conjugation.

In one group of embodiments, the MB is selected from the group consisting of CC1065, lexitropsins, distamycin, netropsin, berenil, duocarmycin, pentamidine, 4,6-diamino-2-phenylindole and pyrrolo[2,1-c][1,4]benzodiazepines analogs.

Further preferred minor groove binders are those selected from the formulae:

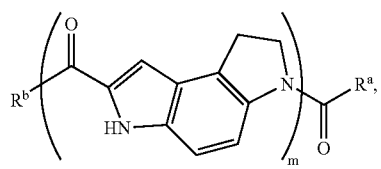

-continued

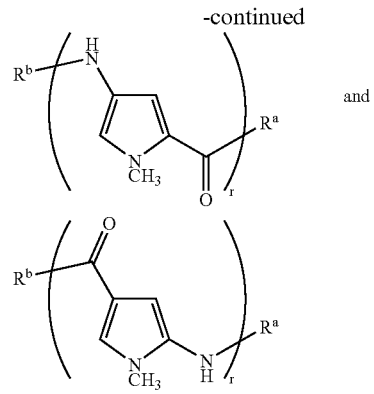

wherein the subscript m is an integer of from 2 to 5; the subscript r is an integer of from 2 to 10; and each $R^a$ and $R^b$ is independently a linking group to the oligonucleotide (either directly or indirectly through a fluorophore), H, $-OR^c$, $-NR^cR^d$, $-COOR^c$ or $-CONR^cR^d$, wherein each $R^c$ and $R^d$ is selected from H, $(C_1-C_{12})$heteroalkyl, $(C_2-C_{12})$heteroalkenyl, $(C_2-C_{12})$heteroalkynyl, $(C_1-C_{12})$alkyl, $(C_2-C_{12})$alkenyl, $(C_2-C_{12})$alkynyl, aryl$(C_1-C_{12})$alkyl and aryl, with the proviso that one of $R^a$ and $R^b$ represents a linking group to ODN or Fl. Each of the rings can be substituted with on or more substituents selected from H, halogen, $(C_1-C_8)$alkyl, $OR^g$, $N(R^g)_2$, $N^+(R^g)_3$, $SR^g$, $COR^g$, $CO_2R^g$, $CON(R^g)_2$, $(CH_2)_{0-6}SO_3^-$, $(CH_2)_6CO_2^-$, $(CH_2)_{0-6}OPO_3^{-2}$, and $NHC(O)(CH_2)_{0-6}CO_2^-$, and esters and salts thereof, wherein each $R^g$ is independently H or $(C_1-C_8)$alkyl.

Particularly preferred minor groove binders include the trimer of 1,2-dihydro-(3H)-pyrrolo[3,2-e]indole-7-carboxamide ($CDPI_3$), the pentamer of N-methylpyrrole-4-carbox-2-amide ($MPC_5$) and other minor groove binders that exhibit increased mismatch discrimination. Additional MB moieties that will find use in the practice of the present invention are disclosed in co-owned U.S. Pat. No. 5,801,155 and U.S. Pat. No. 6,727,356. In certain embodiments, the MBs can have attached water solubility-enhancing groups (e.g., sugars, amino acids, carboxylic acid or sulfonic acid substituents, and the like). See co-pending U.S. application Ser. No. 10/507,267 (based on PCT/US03/07467).

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_o$) is described as the distance between the donor and acceptor molecules where the energy transfer is 50% efficient. Other mechanisms of fluorescence quenching are also known, such as, collisional and charge transfer quenching. There is extensive guidance in the art for selecting quencher and fluorophore pairs and their attachment to oligonucleotides (Haugland, R. P., HANDBOOK OF FLUORESCENT PROBES AND RESEARCH CHEMICALS, Sixth Edition, Molecular Probes, Eugene, Oreg., 1996; U.S. Pat. Nos. 3,996,345 and 4,351,760 and the like). Preferred quenchers are described in co-owned U.S. Pat. No. 6,727,356, incorporated herein by reference. More particularly, Table 1 below contains structures of quenchers that can be readily modified to structures having suitable functional groups (e.g., Q-K- with attachment sites for ODN portions) for introduction into probes, based on the known chemical reactions cited (see, for example, Thiel, et al., *J. fur prakt. Chemie*, 328:497-514 (1986); U.S. Pat. Nos. 4,324,721 and 4,054,560; Timm, *Melliand Textilberichte*, 9:1090-1096 (1969); Hallas, *J.S.D.C.* 285-294 (1979); Beyer, et al., *J Prakt. Chem.*, 24:100-104 (1964); Hutchings, et al., *Chem. Europ. J.* 3:1719-1727 (1997) and Morley, et al., *J. Phys. Chem. A.*, 102:5802-5808 (1998); Haak, et al., *J. Chem. Res. Miniprint* 10:2701-2735 (1998) and Ruggli et al., *Helv. Chim. Acta*, 26:814-826 (1943). Additional structures (e.g., mono- and bis-azo dyes) with different combinations of substituents at various positions can be prepared based on compounds and methods known in the dye chemistry field (summarized in the Color Index, Issue 3 on CDD-ROM, pages 4009-4324; Society of Dyers and Colourists, Bradford, England; http://www.sdc.org.uk; and see also WO 01/86001 and U.S. Pat. No. 6,790,945 incorporated by reference).

TABLE 1

| Structure Literature | $\lambda_{max}$ nm; $\epsilon M^{-1}$ cm$^{-1}$; Solvent | Linker-Modified Structure Q-K- |
|---|---|---|
| O$_2$N—C$_6$H$_4$—CH=CH—C$_6$H$_4$—N=N—C$_6$H$_4$—N(CH$_3$)(allyl) | 464 | O$_2$N—C$_6$H$_2$(CN)(NO$_2$)—CH=CH—C$_6$H$_4$—N=N—C$_6$H$_4$—NH—CH$_2$CH$_2$OH |
| O$_2$N—C$_6$H$_4$—C$_6$H$_4$—N=N—C$_6$H$_5$ | 440 | O$_2$N—C$_6$H$_4$—C$_6$H$_4$—N=N—C$_6$H$_4$—NH—CH$_2$CH$_2$OH |
| O$_2$N—C$_6$H$_3$(NO$_2$)—N=N—C$_6$H$_4$—N(Et)$_2$ | 540; 40,000 MeOH | O$_2$N—C$_6$H$_3$(NO$_2$)—N=N—C$_6$H$_4$—NH—CH$_2$CH$_2$OH |
| O$_2$N—C$_6$H$_2$(NO$_2$)(Br)—N=N—C$_6$H$_4$—N(Et)$_2$ | 549 37,000 EtOH | O$_2$N—C$_6$H$_2$(NO$_2$)(Br)—N=N—C$_6$H$_4$—NH—CH$_2$CH$_2$OH |
| O$_2$N—C$_6$H$_2$(NO$_2$)(CN)—N=N—C$_6$H$_4$—N(Et)$_2$ | 590 48,978 CHCl$_3$ | O$_2$N—C$_6$H$_2$(NO$_2$)(CN)—N=N—C$_6$H$_4$—NH—CH$_2$CH$_2$OH |
| O$_2$N—C$_6$H$_2$(CN)$_2$—N=N—C$_6$H$_4$—N(Et)$_2$ | 601 40,738 CHCl$_3$ | O$_2$N—C$_6$H$_2$(CN)$_2$—N=N—C$_6$H$_4$—NH—CH$_2$CH$_2$OH |
| O$_2$N—C$_6$H$_2$(CN)$_2$—N=N—C$_6$H$_3$(OCH$_3$)—N(Et)$_2$ | 623 48,000 CHCl$_3$ | O$_2$N—C$_6$H$_2$(CN)$_2$—N=N—C$_6$H$_3$(OCH$_3$)—NH—CH$_2$CH$_2$OH |

TABLE 1-continued

| Structure Literature | $\lambda_{max}$ nm; $\epsilon M^{-1} cm^{-1}$; Solvent | Linker-Modified Structure Q-K- |
|---|---|---|
| | 656 100,000 CHCl$_3$ | |
| | 656 53,043 | |
| | 598 | |
| | 582 | |
| | 652 | |
| | 554 50,000 | |
| | 673.5 | |
| | 809 | |

TABLE 1-continued

| Structure Literature | λ_max nm; εM⁻¹ cm⁻¹; Solvent | Linker-Modified Structure Q-K- |
|---|---|---|
| (structure) | 592 46,000 | (structure) |
| (structure) | 601 51,000 | (structure) |
| (structure) | 623 48,000 | (structure) |
| (structure) | 632 Predicted | (structure) |

The quenchers above cover the range from about 400-800 nm, and many demonstrate improved quenching when attached to a MB-Fl-ODN-Q conjugate. While the modified versions illustrate —NH(CH$_2$CH$_2$OH) as a preferred linking group to be used to couple the quencher to oligonucleotides or solid support, examples of other suitable linkers are known in the art or are provided herein or can be prepared from derivatized quenchers such as those in Table 1.

Preferred quenchers for each of the aspects of the invention herein are selected from those in the table above, as well as bis azo quenchers (U.S. Pat. No. 6,790,945) and dyes from Biosearch Technologies, Inc. (provided as Black Hole™ Quenchers: BH-1, BH-2 and BH-3), Dabcyl, TAMRA and carboxytetramethyl rhodamine.

Fluorophores

Fluorophores useful in the present invention are generally fluorescent organic dyes that have been derivatized for attachment to the trifunctional linker W (formula II). One of skill in the art will appreciate that suitable fluorophores are selected in combination with a quencher, which is typically also an organic dye and may or may not be fluorescent.

There is a great deal of practical guidance available in the literature for selecting appropriate fluorophore-quencher pairs for particular probes. See, for example, Clegg (cited above); Wu et al. (cited above); Pesce et al., editors, FLUO-RESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic (quenching) molecules and their relevant optical properties for choosing fluorophore-quencher pairs, e.g., Berlman, HANDBOOK OF FLUORESCENCE SPECTRA OF AROMATIC MOLECULES, 2ND EDITION (Academic Press, New York, 1971); Griffiths, COLOUR AND CONSTITUTION OF ORGANIC MOLECULES (Academic Press, New York, 1976); Bishop, editor, INDICATORS (Pergamon Press, Oxford, 1972); Haugland, HANDBOOK OF FLUORESCENT PROBES AND RESEARCH CHEMICALS (Molecular Probes, Eugene, 1992); Pringsheim, FLUORESCENCE AND PHOSPHORESCENCE (Interscience Publishers, New York, 1949); and the like. Additionlly, methods for derivatizing fluorophores and quenchers for covalent attachment via common reactive groups are also well known. See, for example, Haugland (cited above); Ullman et al., U.S. Pat. No. 3,996,345; Khanna et al., U.S. Pat. No. 4,351,760; and the like.

Preferred fluorophores are those based on xanthene dyes, a variety of which are available commercially with substituents useful for attachment of either a linking group or for direct attachment to an oligonucleotide. Another group of fluorescent compounds are the naphthylamines, having an amino group in the α- or β-position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like. Still other suitable fluorophores include the resorufin dyes, rhodamine dyes, cyanine dyes and BODIPY dyes.

These dyes and appropriate linking methodologies for attachment to oligonucleotides are described in many references, e.g., Khanna et al. (cited above); Marshall, *Histochemical J.*, 7:299-303 (1975); Menchen et al., U.S. Pat. No. 5,188,934; Menchen et al., European Patent Application 87310256.0; and Bergot et al., International Application PCT/US90/05565.

More particularly, the fluorophores described herein can be attached to the oligonucleotide portions using, for example, chemical or enzymatic methods. By way of example, methods for incorporation of reactive chemical groups into oligonucleotides, at specific sites, are well known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. No. 5,824,796; U.S. Pat. No. 5,210, 015; Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774-1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767. Examples of modifying enzymes include, but are not limited to, DNA polymerases, reverse transcriptases, RNA polymerases, etc. Examples of enzymes that are able to add a label to an already-existing oligonucleotide include, but are not limited to, kinases, terminal transferases, ligases, glycosylases, etc.

For each of the aspects of the present invention, preferred fluorophores are selected from Cy dyes, BODIPY analogs, 5-FAM™, 6-FAM™, TET™, JOE™, HEX™, VIC™, NED™, TAMRA™, ROX™, Bothell Blue™ and Yakima Yellow™ (YY), where VIC™, NED™ and Yakima Yellow™ (YY) correspond to compounds having the following structures:

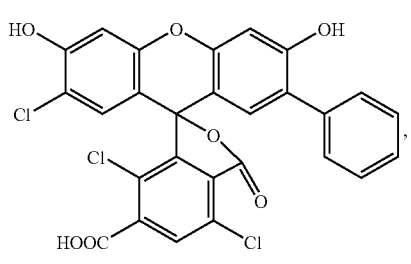

VIC™

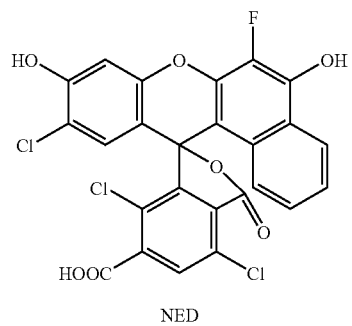

NED

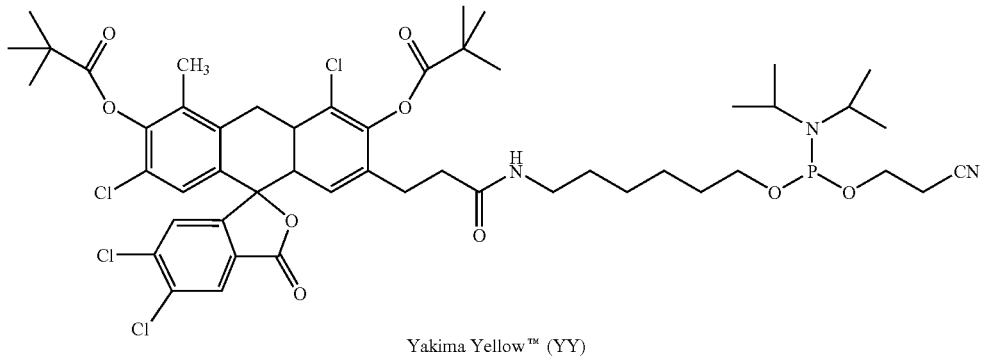

Yakima Yellow™ (YY)

These fluorophores are generally available from commercial sources such as Glen Research, Sterling, Va., Molecular Probes, Eugene, Oreg., Applied Biosystems Inc., Foster City, Calif. and Epoch Biosciences, Inc., Bothell, Wash.

Linking Groups

A variety of linking groups and methods are known to those of skill in the art for attaching fluorophores, quenchers and minor groove binders to the 5' or 3' termini of oligonucleotides. See, for example, Eckstein, editor, OLIGONUCLEOTIDES AND ANALOGUES: A PRACTICAL APPROACH (IRL Press, Oxford, 1991); Zuckerman et al., *Nucleic Acids Research*, 15:5305-5321 (1987); Sharma et al., *Nucleic Acids Research*, 19:3019 (1991); Giusti et al., *PCR Methods and Applications*, 2:223-227 (1993), Fung et al., U.S. Pat. No. 4,757,141; Stabinsky, U.S. Pat. No. 4,739,044; Agrawal et al., *Tetrahedron Letters*, 31:1543-1546 (1990); Sproat et al., *Nucleic Acids Research*, 15:4837 (1987); Nelson et al., *Nucleic Acids Research*, 17:7187-7194 (1989); and the like. Still other commercially available linking groups can be used that can be attached to an oligonucleotide during synthesis, e.g., available from Glen Research. Other methodologies for attaching a fluorophore to an oligonucleotide portion involve the use of phosphoramidite chemistry at the conclusion of solid phase synthesis by way of dyes derivatized with a phosphoramidite moiety. See, for example, Woo et al., U.S. Pat. No. 5,231,191; Hobbs, Jr., U.S. Pat. No. 4,997,928; Reed, et al., PCT publication No. WO 01/42505; U.S. Pat. No. 6,653,473 and U.S. application Ser. No. 10/026,374.

While a number of general linking methods are available, the selection of certain linking groups constitute one aspect of the invention, when selection is made in combination with other factors such as oligonucleotide length, minor groove binders, fluorophore-quencher pairs, and the like.

The probes and conjugates of the present invention will generally have one or two types of linking groups. As provided in formula I, the letter K represents a divalent linking group, while the letter W represents a trivalent linking group. The particular linking groups are generally selected for their ease of synthesis, utility in solid phase synthesis, stability during probe construction and use, and the physical parameters each imparts to the probe or conjugate such as providing adequate separation between the fluorophore and the quencher; or providing a tether of suitable length to allow the minor groove binder portion to non-covalently interact with the minor groove formed upon probe hybridization.

More particularly, K is a direct bond between quencher and the oligonucleotide portion of the probe/conjugate, or is a divalent linking group having from 1 to 30 main chain atoms that are selected from C, O, N, S, P and Si. The preferred structure of K is represented by formula:

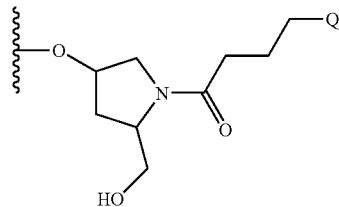

wherein Q represents quencher moiety, which has the meaning provided above and the wavy line indicated the point of attachment to the remainder of the probe or conjugate.

The trivalent linking group W can encompass a variety of structures in order to provide suitable attachment and flexibility between the ODN, Fl and MB. In one group of embodiments, W is a trivalent functionality having the formula:

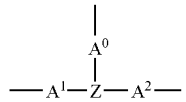

wherein the Z is an acyclic or cyclic moiety having from 1 to 10 atoms selected from C, N, S, P, Si and O; aryl and, the components $A^0$, $A^1$ and $A^2$ are independently selected from a bond or a linking/spacer portion having from 1 to about 50 atoms selected from C, N, S, P, Si and O, and additional hydrogen atoms to fill the available valences. Additionally, each of $A^0$, $A^1$ and $A^2$ can have cyclic components, acyclic (linear or branched) alkyl components (including unsaturated alkyl components), aryl components, or a combination thereof.

Preferred Dye-Linkers:

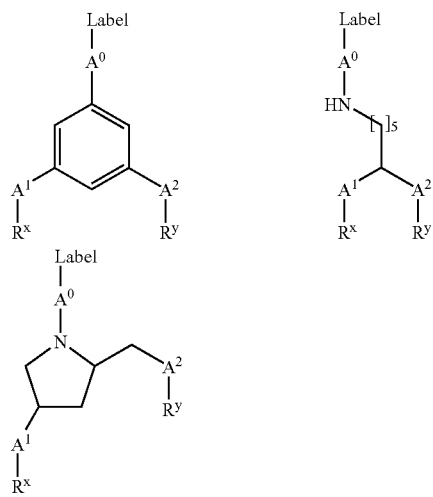

wherein each of $A^0$, $A^1$ and $A^2$ have been defined above; the label is generally a quencher, $R^x$ and $R^y$ are attachment sites to the remainder of the probe or conjugate. For example, $R^x$ and $R^y$ can be MB portions and ODN (or $[A-B]_n$) portions of the probe conjugate. However, the present invention is also directed to reagents useful in preparing the probes/conjugates described herein. Accordingly, in some aspects of the invention, each of $R^x$ and $R^y$ is independently selected from H, phosphoramidite, PFP ester, NHS ester, solid support and an atom blocked with a protective group compatible with oligonucleotide synthesis. One of skill in the art will appreciate that each of the rings in the above formulae (for W) can be substituted with on or more substituents selected from H, halogen, $(C_1-C_8)$alkyl, $OR^g$, $N(R^g)_2$, $N^+(R^g)_3$, $SR^g$, $COR^g$, $CO_2R^g$, $CON(R^g)_2$, $(CH_2)_{0-6}SO_3^-$, $(CH_2)_{0-6}CO_2^-$, $(CH_2)_{0-6}OPO_3^{-2}$, and $NHC(O)(CH_2)_{0-6}CO_2^-$, and esters and salts thereof, wherein each $R^g$ is independently H or $(C_1-C_8)$alkyl.

The valances of the W linker, which connect to the minor groove binder and ODN, in structure I may have additional linking group such as

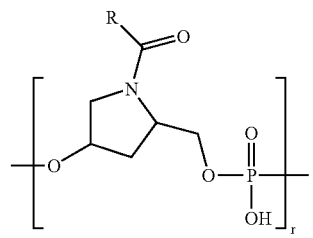

wherein subscript r is an integer of from 0 to 5, preferably 1, most preferably 2. R is alkyl, preferably methyl.

Preparation of Intermediates and Oligonucleotide Conjugates

Reaction Schemes 1-8 provide illustrative methods for preparing MB-Fl-ODN-Q conjuguates and a number of intermediates that are useful in the present invention. The schemes illustrate the preparation of solid support, and linking phosphoramidite derivatives that can be used in, for example, automatic synthesizers for preparing the probes of the invention.

Reaction Scheme 1
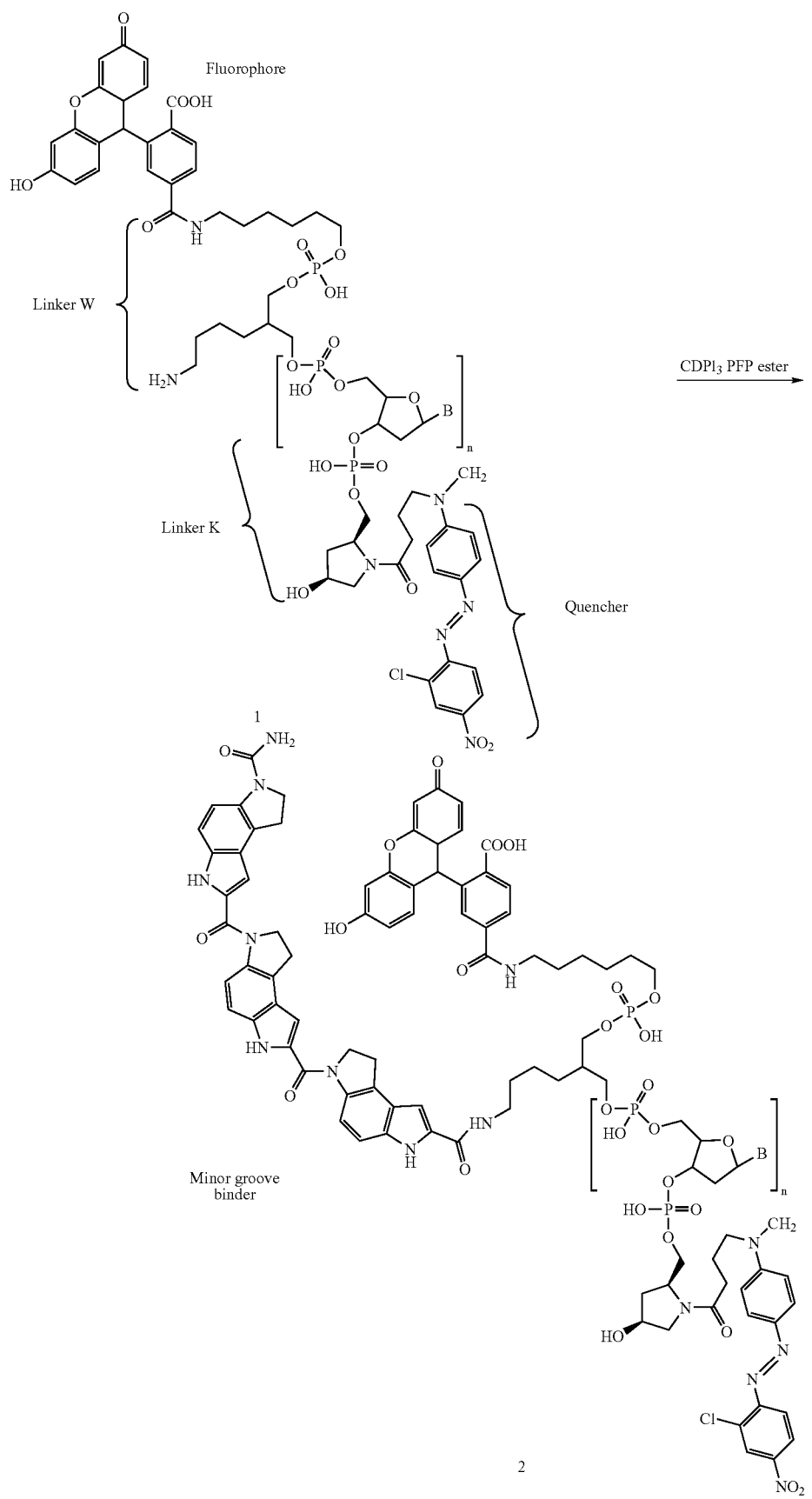

Reaction Scheme 1 illustrates the post-synthesis approach to prepare a MB-W(-Fl)-ODN-K-Q 2 conjugate starting from a NH$_2$—W(-Fl)-ODN-K-Q 1, synthesized by methods known in the art. The amino group on W in conjugate 1 was derivatized with an activated ester of CDPI$_3$ as described (Lukhtanov et al, *Bioconj. Chem.*, 6:418-426 (1995)) to yield modified oligonucleotide (2). The fluorophore was fluorescein and the quencher was the ECLISPE™ Quencher (Epoch Biosciences, Bothell, Wash.). In this particular example, MB ligand and fluorophore were located at the 5' end of the DNA probe and the quencher at the 3' end. The reverse orientation is also possible if 5'-phosphoramidites are used to synthesize the amino-tailed probe precursor.

Figure 6:
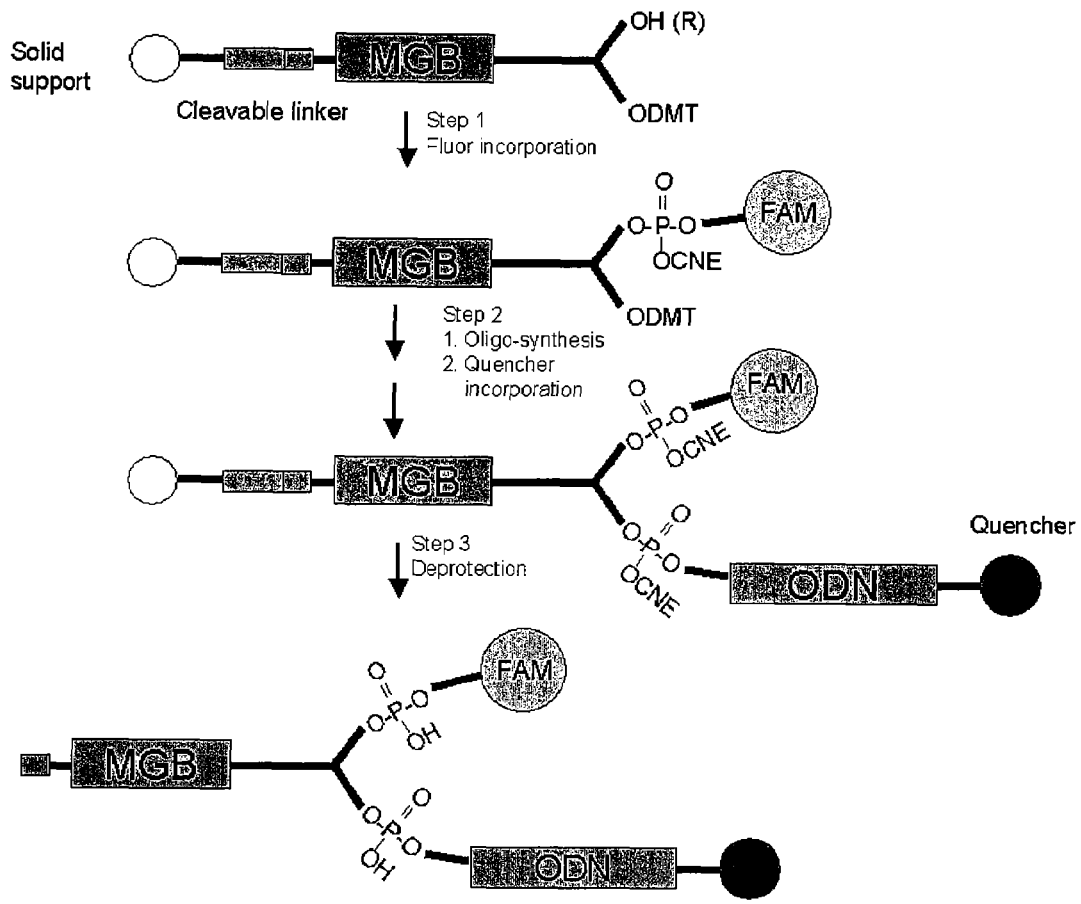
FIG. 6 shows a schematic approach for branched assembly of conjugates of the invention on a solid support.

FIG. 6, illustrates an approach to automate the assembly of the probes (conjugates) of the invention on a commercial oligonucleotide synthesizer. This scheme affords probes with the same orientation and linker structures with MB ligand, fluorophore and quencher as in Reaction Scheme 1. In this approach a MB ligand is attached to the solid support (S) via a cleavable linker. The MB also has a dihydroxy terminated second linker at the distal end of the MB moiety, in which one of the hydroxy groups is DMTr (Dimethoxytrityl) protected and the other is either free or protected with a group (R) that can be removed without deprotecting DMTr group. Using this support a fluorophore is incorporated first at the free (or other than DMTr protected) hydroxy group using a fluorophore phosphoramidite reagent. At the second step normal oligonucleotide synthesis is performed, using commercially available phosphoramidite bases, with final incorporation of the quencher moiety using known quencher phosphoramidite reagents. Finally, at the third step, fully assembled probes are deprotected and cleaved from the solid support using standard or adjusted deprotection conditions.

Reaction Schemes 2 and 3 provide one method for the preparation of a MB solid support with a cleavable linker used in the synthesis of MB-Fl-ODN-Q conjugates as illustrated in FIG. 6. More particularly, these schemes illustrate the synthesis of a solid support with a cleavable linker (Reaction Scheme 2) which is coupled to a MB reagent containing a blocked dihydroxy linking group. More particular, these schemes illustrate the preparation of the desired MB solid support 14 required for automated oligonucleotide synthesis on a synthesizer.

In the first portion (Reaction Scheme 2) pentafluorophenyl activated solid support 7 was synthesized starting from monobenzyl succinate. Intermediate 3 was synthesized from monobenzyl succinate (*J. Org. Chem.*, 66:4115-4121 (2001)) by reaction with tert-butyl 4-chlorobutyrate (prepared from 4-chlorobutyryl chloride and tert-butanol). The benzyl group was removed by catalytic hydrogenation and the free carboxy group was then reacted with pentafluorophenyl trifluoroacetate (PFP-TFA) to afford PFP ester 4. Using this PFP ester, the amino-modified solid support was converted to tert-butyl-protected support 5. Finally, the terminal carboxyl group was deprotected to afford solid support 6 and converted to PFP ester to give PFP-activated support 7.

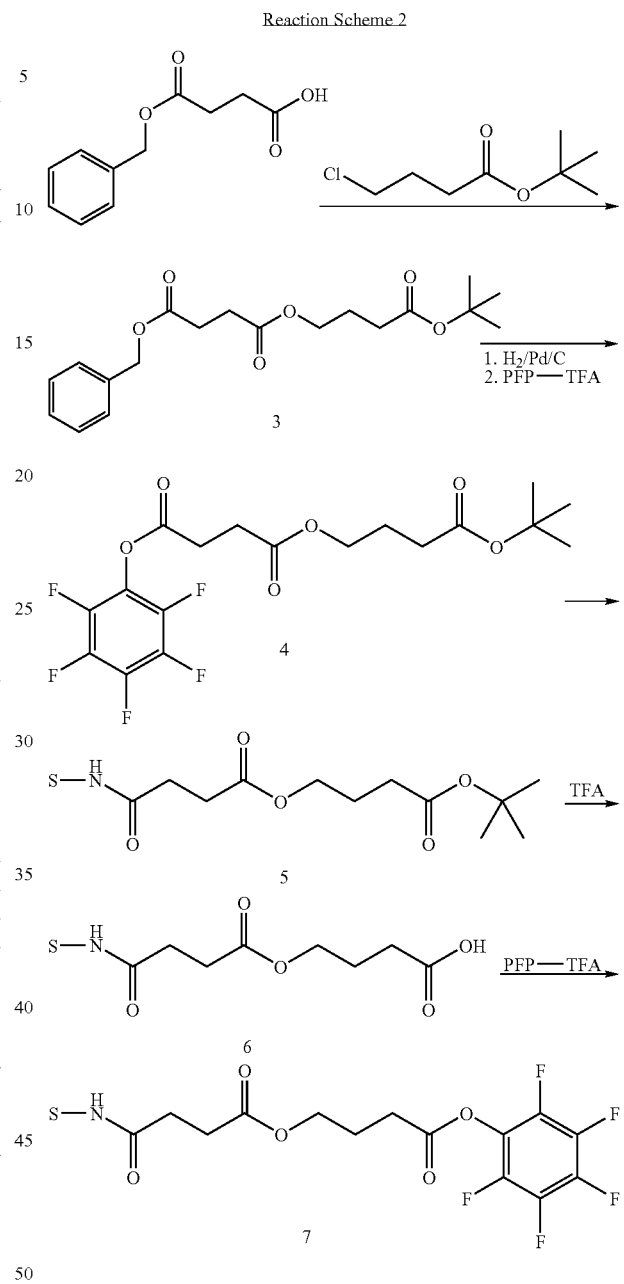

Reaction Scheme 2

In the second part (Reaction Scheme 3) MB solid support 14 required for automated oligonucleotide synthesis was synthesized starting from t-Boc protected DPI monomer derivative. The Fmoc protected DPI monomer derivative 9 was prepared by removal of the Boc protecting group with trifluoroacetic acid from the DPI derivative 8, followed by the reaction with 9-fluoronylmethoxycarbonyl chloride (Fmoc-Cl). This material was then reacted successively with PFP-TFA and the DMTr-protected 2-(5-aminopentyl)propane-1,3-diol to yield the Fmoc-DPI PFP-ester 10 and diol-linked DPI derivative 11. The Fmoc group of 11 was removed and coupled with a second Fmoc-DPI PFP-ester to yield the Fmoc-DPI$_2$ intermediate. One additional deprotection and coupling afforded Fmoc protected MGB ligand (dihydrocyclopyrroloindole triamide DPI$_3$ 12; MGB is a Trademark of Epoch Biosciences). Removal of the Fmoc group of 12 yielded the amine-containing DPI$_3$ ligand 13. Reaction of solid support 7 and DPI$_3$-intermediate 13 produced the DPI$_3$ solid support 14 with a cleavable linker. Solid support 14 was used to synthesize MGB-Fl-ODN-Q conjugates with various Fl and Q combinations. One preferred combination was synthesized with fluorescein as a fluorophore and the ECLISPE™ Dark Quencher (available from Glen Research, Sterling, Va.).

In this approach a MB ligand is attached to the solid support (S) via a cleavable linker. The MB also terminates in a second linker at the distal end of the MB moiety, in which a hydroxy group is DMTr (Dimethoxytrityl) protected. In the first step, using this deblocked support, a trifunctional fluorophore phosphoramidite containing DMTr protected hydroxy group is attached. In the second step, normal oligonucleotide synthesis is performed, using commercially

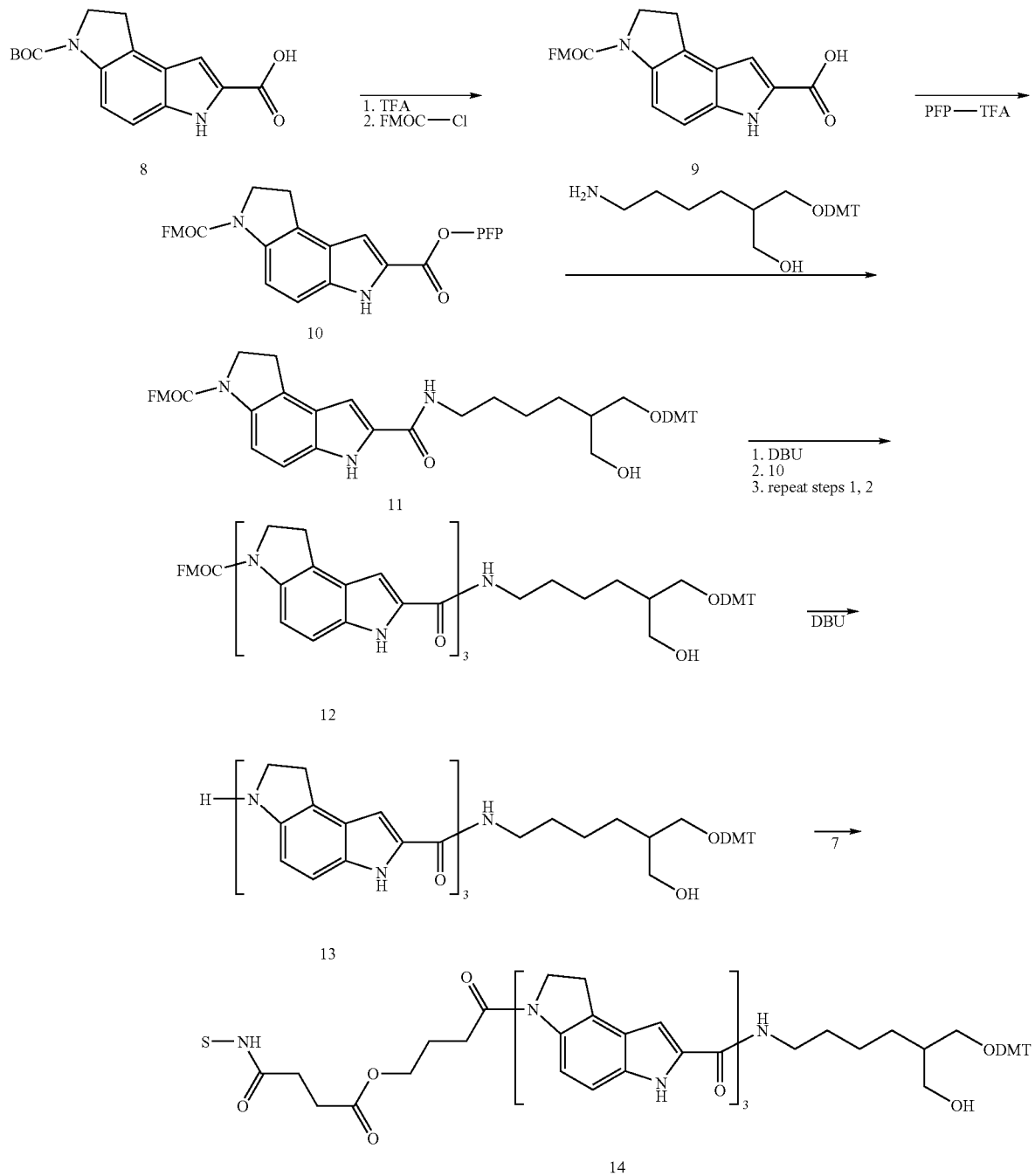

Figure 7:
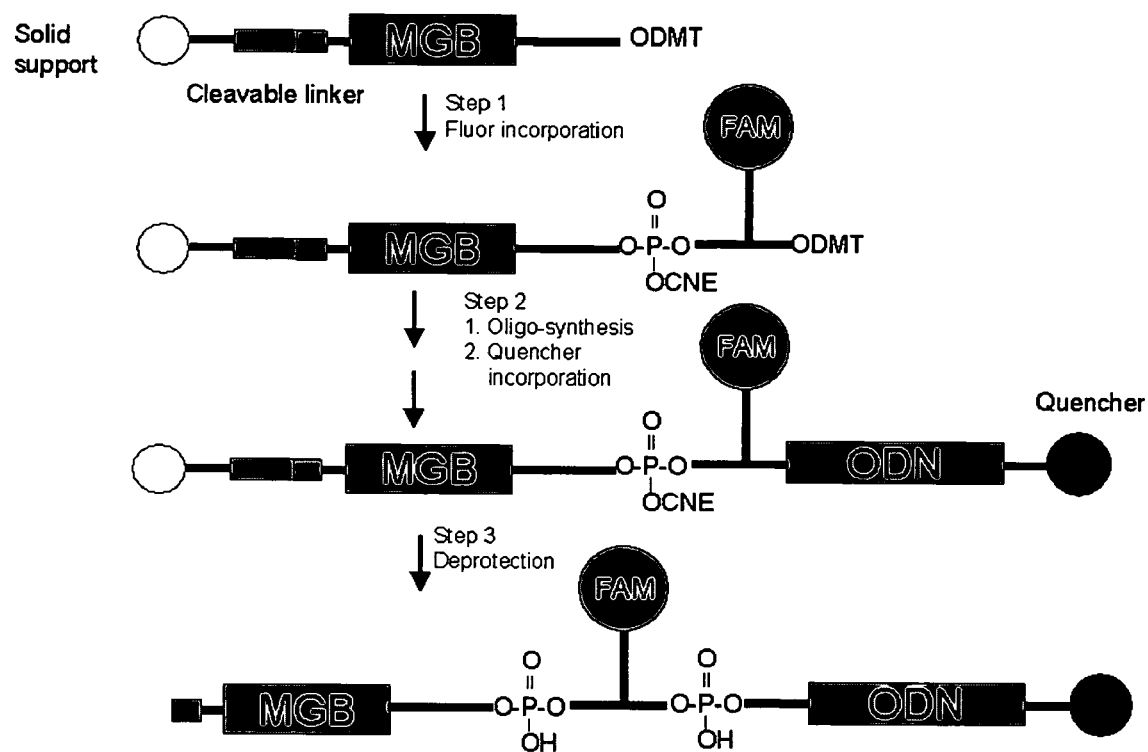
FIG. 7 shows a schematic approach for linear assembly of conjugates of the invention on a solid support.

FIG. 7 schematically shows a particularly preferred way to assemble the MB-Fl-ODN-Q conjugates on a synthesizer.

available phosphoramidite bases, with final incorporation of the quencher moiety using known quencher phosphoramidite reagents. Finally, in the third step, fully assembled probes are de-protected and cleaved from the solid support using standard or adjusted deprotection conditions.

Reaction Schemes 4 and 5 provide a preferred method for the preparation of a MB solid support with a cleavable linker used in the synthesis of MB-Fl-ODN-Q conjugates as illustrated in FIG. 7. More particularly, these schemes illustrate the synthesis of a solid support with a cleavable linker (Reaction Scheme 4) which is coupled to a MB reagent containing a blocked hydroxy linking group 20 useful for automated oligonucleotide synthesis on a synthesizer.

In the first portion (Reaction Scheme 4) DMT blocked solid support 20 was synthesized starting from the methyl ester of the DPI moiety 8. Intermediate 15 was synthesized by the introduction DMT-hydroxyhexanoic acid linker at the N-terminus of DPI moiety by the reaction of the methyl ester of 8 with 6-O-dimethoxytrityl-hexanoyl 4-nitrophenyl ester.

Saponification of the methyl ester 15 and reaction with PFP-TFA afforded DMTr-hydroxyhexanoyl-DPI PFP ester 16 which was then reacted with $DPI_2$ nitrophenylethyl ester 17 (see U.S. Patent Publication 20020034754) to give the DMTr-hydroxyhexanoyl-$DPI_3$ NPE ester 18. Removal of the NPE group with 1,8-diazabicyclo[5.4.0]undec-7-ene (DBU), and activation of the free carboxy group with PFP-TFA generated DMTr-hydroxyhexanoyl-$DPI_3$ PFP ester 19 suitable for coupling with an appropriate amino-modified solid support to provide DMT-hydroxyhexanolyl-$DPI_3$ solid support 20. In this particular example of an amino-modified solid support, MMT-aminopentyl diglycolate solid support 22 was utilized after deprotection of the MMT group. One of skill in the art will appreciate that essentially any solid support used in the art to synthesize oligonucleotides can be used, including for example, control pore glass, polystyrene, nylon and the like.

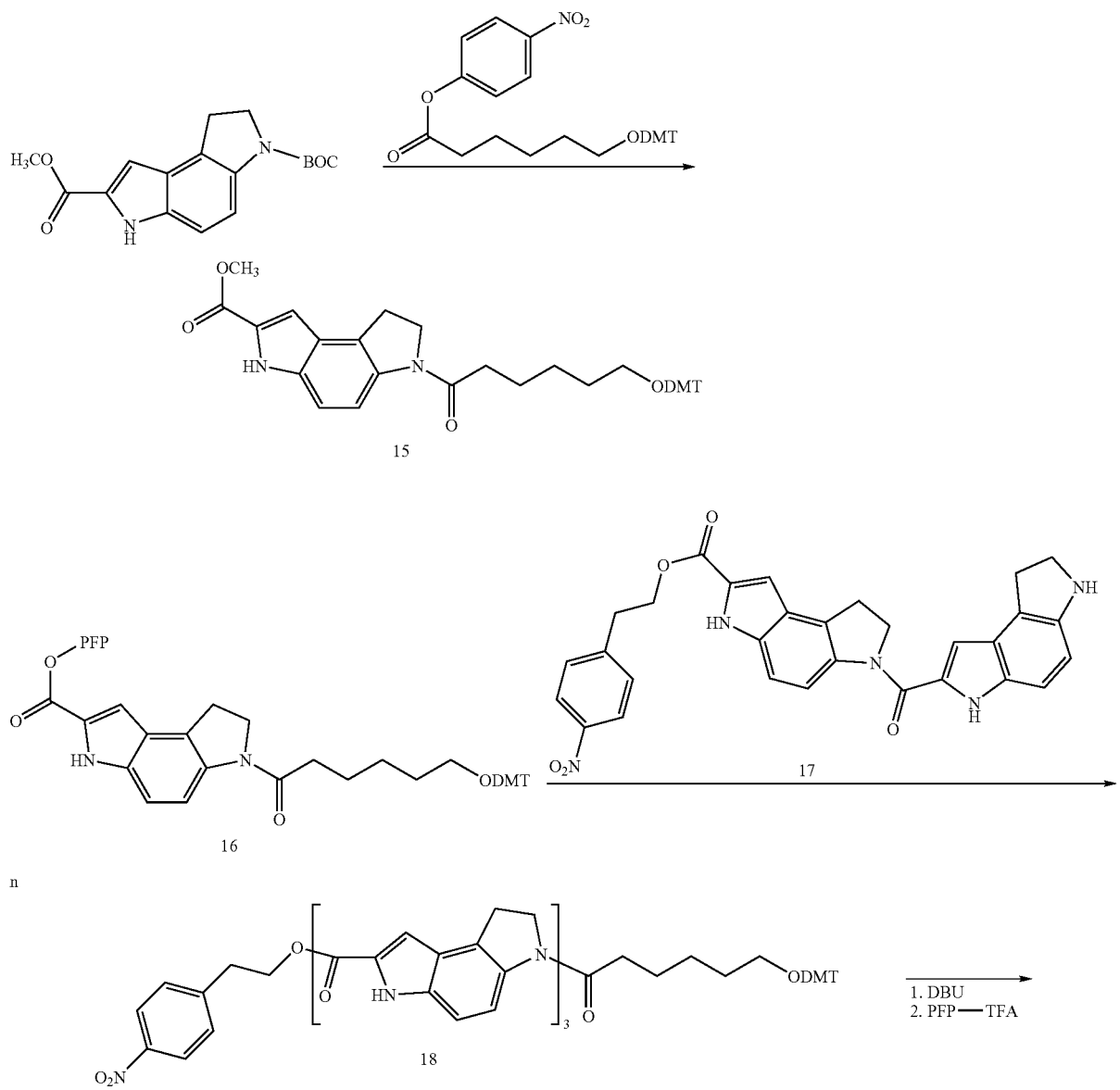

Reaction Scheme 4

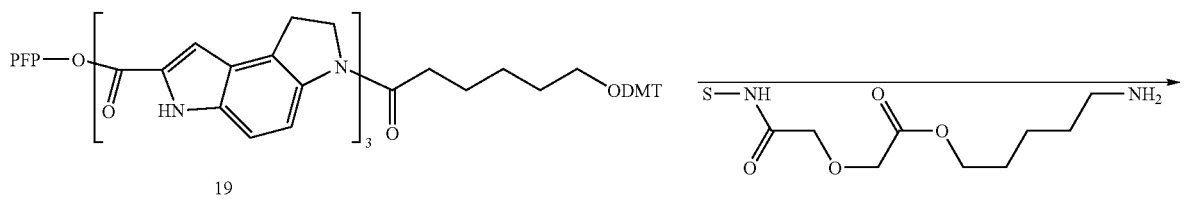

19

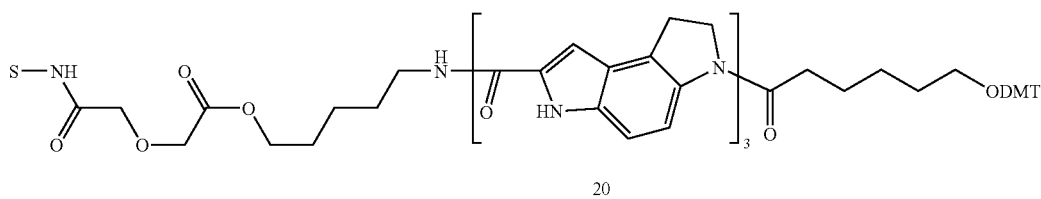

20

In the second part (Reaction Scheme 5) MMT-aminopentyl diglycolate support 22 (used to prepare 20 in Reaction Scheme 4) was prepared starting from 5-aminopentanol. 5-Aminopentanol was protected by reaction with monomethoxytrityl chloride (MMT-Cl) to give MMT-aminopentanol which in turn reacted with diglycolic anhydride to afford MMT-aminopentyl diglycolate 21. This intermediate was coupled with amine-containing solid support (such as aminomethyl polystyrene or long chain aminoalkyl CPG (controlled pore glass)) in the presence of coupling reagents suitable for amide bond formation to afford the required MMT-aminopentyl diglycolate support 22. The MMT group was removed by treatment with a solution of trichloroacetic acid in dichloromethane prior to reacting with the MB PFP ester 19; in Reaction Scheme 4.

Reaction Scheme 5

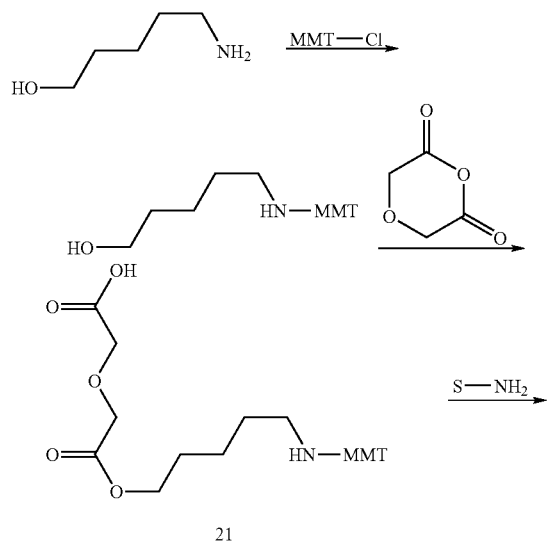

21

-continued

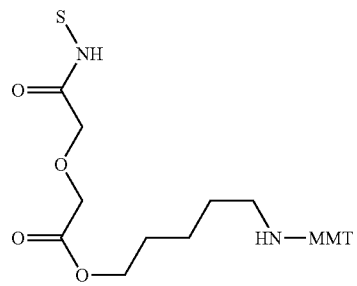

22

Reaction Scheme 6 provides an illustrative method for the synthesis of fluorogenic phosphoramidite 31. 5-Hydroxyisophthalic acid dimethyl ester and hexaethylene glycol were conjugated in the presence of diethyl azodicarboxylate (DEAD) and triphenylphosphine to hydroxy intermediate 23. Reaction of 23 with tosyl chloride gave the tosyl ester 24 which was reacted with sodium azide to yield the azide derivative 25. Reduction with LiAlH$_4$, simultaneously reduced the esters to hydroxymethyl groups and the azide to a primary amine yielding aminodiol 26. The amino group of 26 was blocked by reaction with 9-fluorenylmethyloxycarbonyl chloride (FmocCl) to yield 27, followed by blocking of one of the hydroxyl groups by reaction with DMTCl to yield 28. After deblocking of the Fmoc group, the free aminogroup in 29 is reacted with PFP dipivaloylfluorescein-6-carboxylate (Nucleoside&Nucleotides (1997) 16(1 &2), 107-114) to give 30. At the last step hydroxy precursor 30 was converted to phosphoramidite 31.

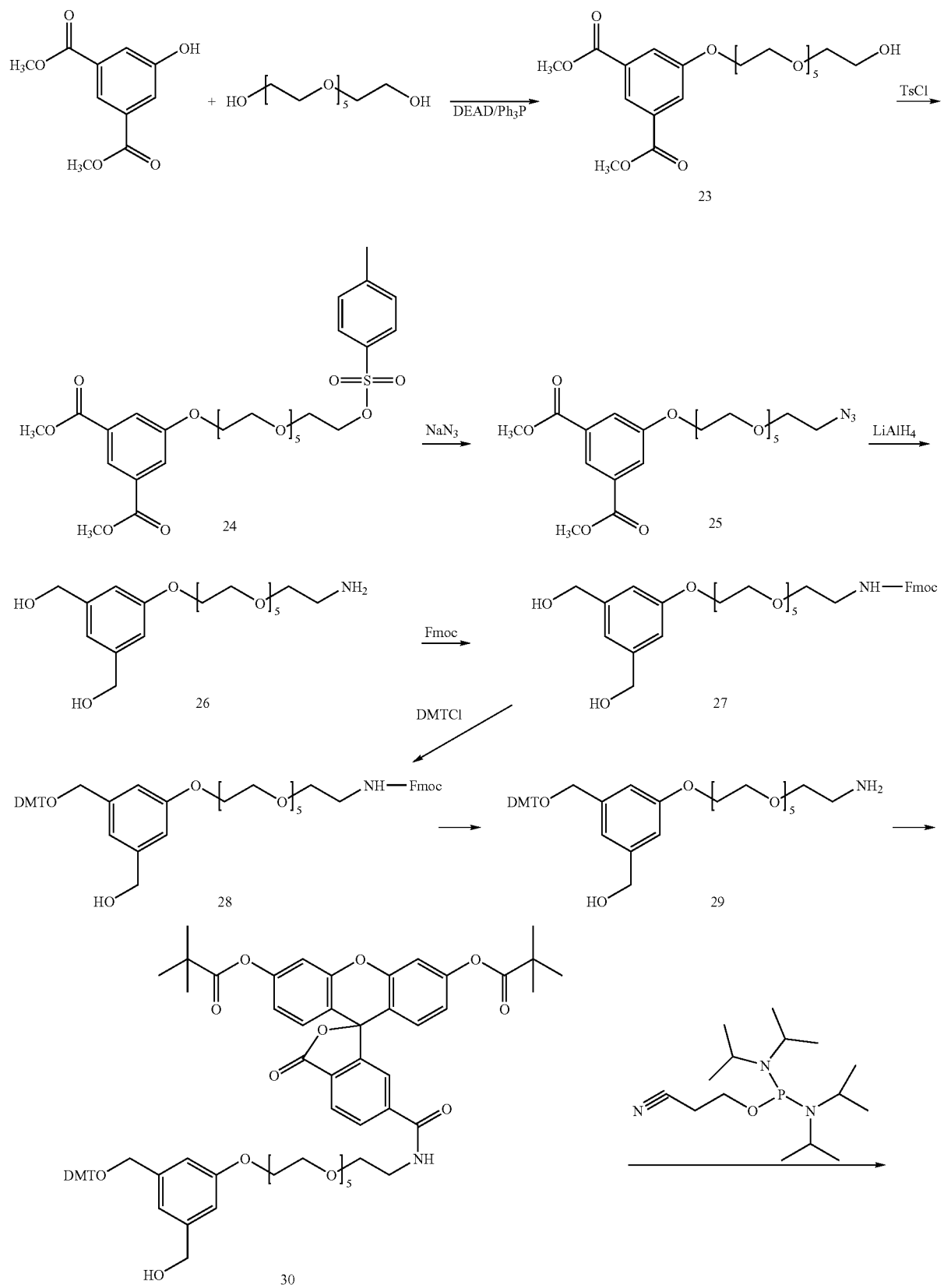
Reaction Scheme 6

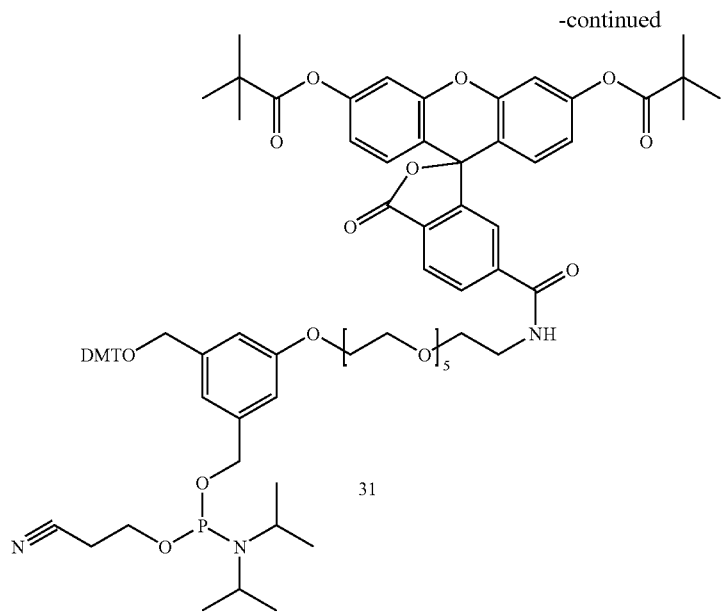

Reaction Scheme 7 illustrates the synthesis of preferred fluorogenic phosphoramidite 41. At the first step methyl 4-hydroxybenzoate is reacted with hexaethylene glycol in the presence of diethylazodicarboxylate and triphenylphosphine to provide hydroxy intermediate 32. Reaction with tosyl chloride yielded tosylate 33. The tosylate was converted into azide 34 by reaction with sodium azide. Catalytic reduction (H₂/10% Pd on carbon) produced amine 35. The compound 35 was treated with sodium hydroxide to saponify the ester group. The following treatment with Fmoc chloride gave acid 36. Acid 36 was converted into PFP ester 37 by reaction with PFP-TFA. The ester was then reacted with DMT-hydroxyprolinol (38) to afford Fmoc intermediate 39. The amino group of 39 was liberated by treatment with DBU and then reacted with pentafluorophenyl dipivaloylfluorescein-6-carboxylate to afford hydroxy derivative 40. Conversion of 40 to the phosphoramidite 41 follows standard methods for the introduction of a phosphoramidite moiety.

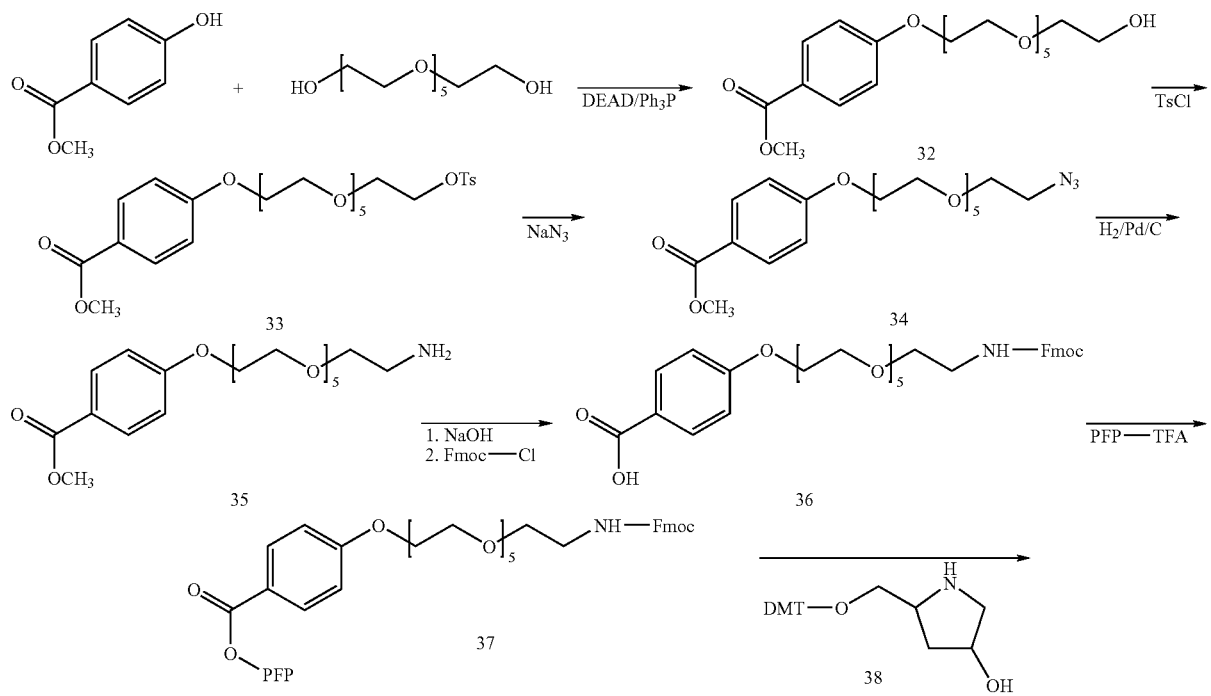

Reaction Scheme 7

-continued
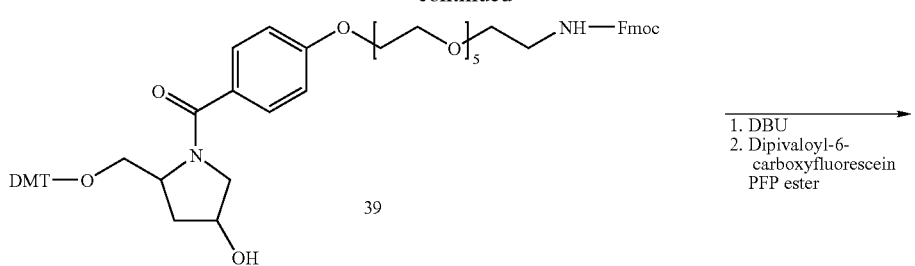
39
1. DBU
2. Dipivaloyl-6-carboxyfluorescein PFP ester
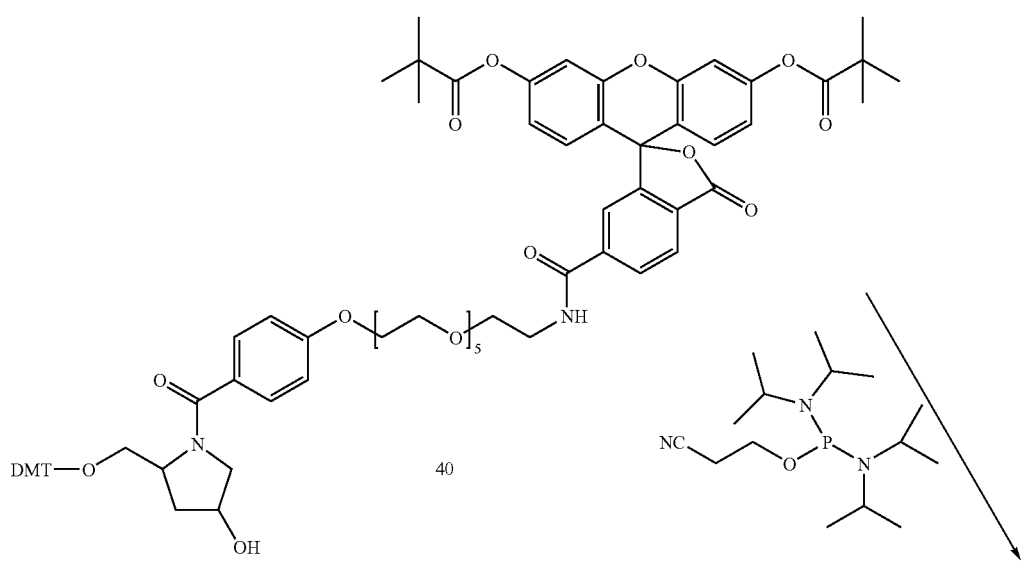
40
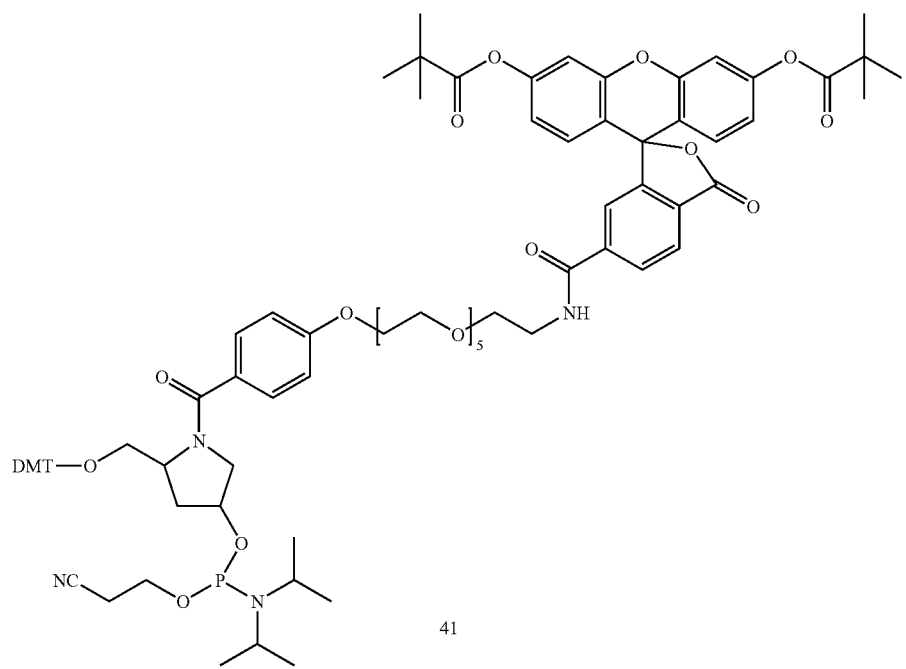
41

Reaction Scheme 8 illustrates the step-wise assembly a particularly preferred MB-Fl-ODN-Q conjugate 43 using the solid support 20, fluorescein phophoramidite 41 and a ECLIPSE™ Quencher phophoramidite 42 (available from Glen Research, Stirling, Va.).

Still other aspects of the present invention are the derivatized solid supports, quenchers, fluorophores and minor groove binders used in assembling the probes described above. In particular, those components having attached linking groups (either protected or unprotected) and pro-

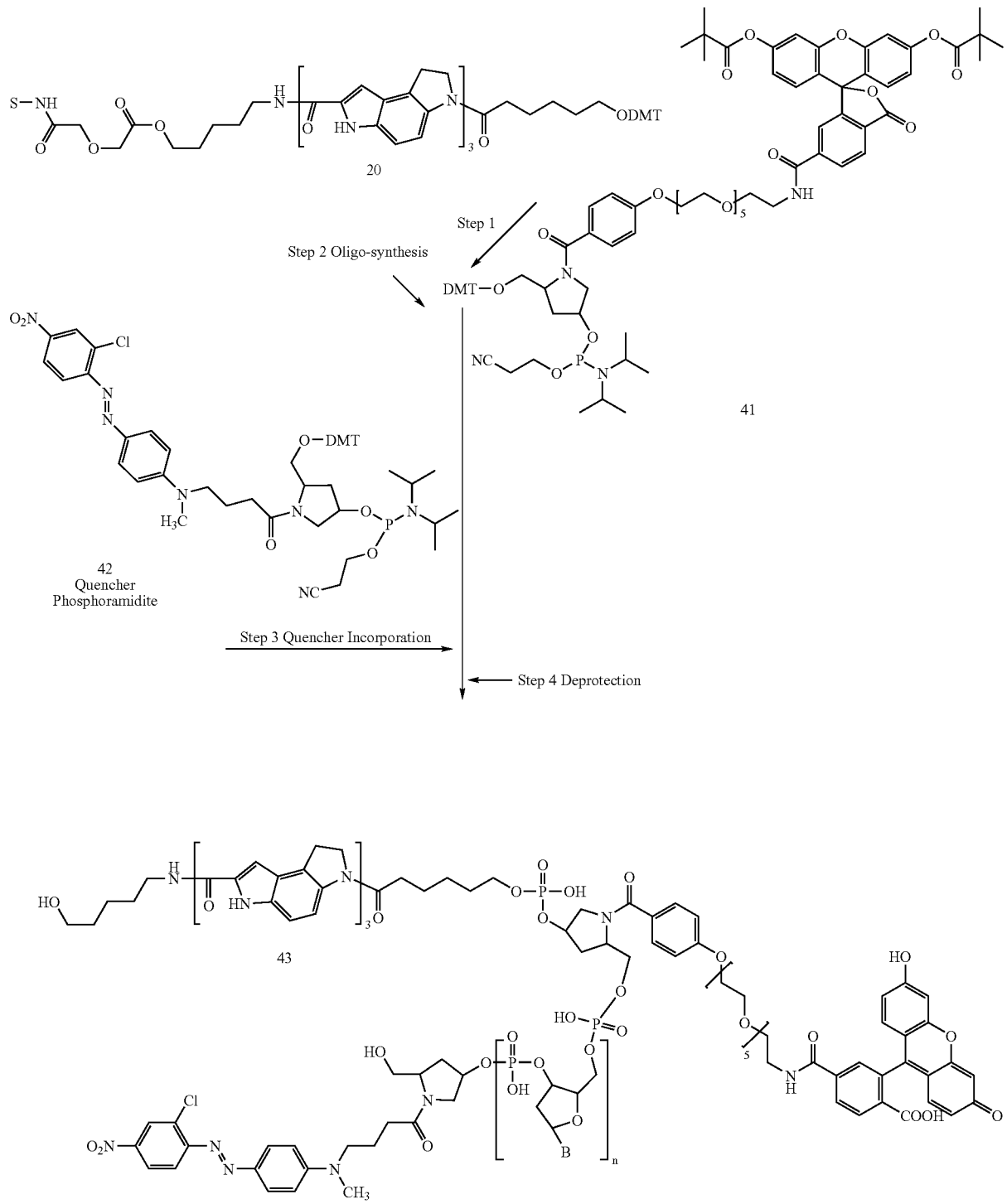

vided typically as phosphoramidite derivatives for use in solution phase or solid phase assembly are particularly preferred (e.g., U.S. Pat. Nos. 6,790,945, 6,084,102, WO 03/023357 and WO 01/64958).

Methods of Use

In one related aspect, the present invention provides methods for continuous monitoring of polynucleotide amplification, comprising:

(a) combining a sample containing a target sequence, with one or more oligonucleotide primers complementary to regions of the target sequence, a polymerizing enzyme, nucleotide substrates, and an oligonucleotide conjugate having a formula:

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence of the fluorophore, more preferably less than 5%, still more preferably less than 2% and in the most preferred embodiments is less than 1%; and iii) when said oligonucleotide conjugate hybridizes to said target sequence, the fluorescence of Fl is at least 50% of its unquenched fluorescence, more preferably at least 60%, still more preferably at least 80% and in the most preferred embodiments is at least 90%; to provide a mixture;

(b) incubating said mixture under conditions favorable for amplification of said polynucleotide; and (c) continuously monitoring said amplification by monitoring the fluorescence produced upon conjugate hybridization to amplified target. In some preferred embodiments, the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs. In other preferred embodiments, the Fl portion is a fluorophore having an emission wavelengths of from about 400 nm to about 800 nm, said fluorophore being selected from the group consisting of coumarins, resorufins, xanthenes, benzoxanthenes, cyanines and BODIPY™ analogs. In still other preferred embodiments, the Q portion is a member selected from the group consisting of mono azo and bis azo dyes. In yet other preferred embodiments, the ODN portion of said conjugate is from 8-25 nucleotides in length. In still other preferred embodiments, the ODN portion of said conjugate is from 8-15 nucleotides in length and K is a linker having a length of from 10-50 main chain atoms selected from the group consisting of C, O, N, S, P and Si.

Another related aspect of the present invention provides methods for monitoring gene expression comprising:

(a) providing an array of oligonucleotide probes of different sequences, (b) incubating a population of polynucleotides with the array under hybridization conditions, and (c) determining to which of the oligonucleotide probes in the array the population hybridizes;

wherein one or more of the oligonucleotide probes is an oligonucleotide conjugate having the formula:

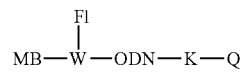

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence of the fluorophore, more preferably less than 5%, still more preferably less than 2% and in the most preferred embodiments is less than 1%; and iii) when said oligonucleotide conjugate hybridizes to said target sequence, the fluorescence of Fl is at least 50% of its unquenched fluorescence, more preferably at least 60%, still more preferably at least 80% and in the most preferred embodiments is at least 90%. In some preferred embodiments, the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and BODIPY™ analogs, and said Q portion is a member selected from the group consisting of mono azo and bis azo dyes. In other preferred embodiments, the conjugates are attached to a solid support.

In another related aspect, the present invention provides methods for discriminating between polynucleotides which differ by a single nucleotide, the method comprising:

(a) separately incubating each of at least two polynucleotides with an oligonucleotide conjugate having the formula:

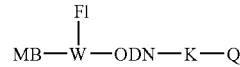

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence of the fluorophore, more preferably less than 5%, still more preferably less than 2% and in the most preferred embodiments is less than 1%; and iii) when said oligonucleotide conjugate hybridizes to said target sequence, the fluorescence of Fl is at least 50% of its unquenched fluorescence, more preferably at least 60%, still more preferably at least 80% and in the most preferred embodiments is at least 90%, said conjugate having a defined sequence under hybridization conditions, wherein one of the polynucleotides has a target sequence that is perfectly complementary to said oligonucleotide conjugate and at least one other of the polynucleotides has a target sequence having a single-nucleotide mismatch with the oligonucleotide conjugate; and (b) determining the hybridization strength between each of the polynucleotides and the oligonucleotide conjugate. As above, certain preferred embodiments are those in which the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and BODIPY™ analogs, and said Q portion is a member selected from the group consisting of mono azo and bis azo dyes.

In still another related aspect, the present invention provides methods for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising:

(a) contacting the mixture of polynucleotides with an oligonucleotide conjugate having the formula:

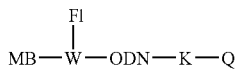

wherein MB is a minor groove binder, Q is a quencher, ODN is an oligonucleotide or modified oligonucleotide, K is a bond or a linking group, Fl is a fluorophore and W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence of the fluorophore, more preferably less than 5%, still more preferably less than 2% and in the most preferred embodiments is less than 1%; and iii) when said oligonucleotide conjugate hybridizes to said target sequence, the fluorescence of Fl is at least 50% of its unquenched fluorescence, more preferably at least 60%, still more preferably at least 80% and in the most preferred embodiments is at least 90%; and wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence or absence of said target sequence. Preferred embodiments include those described above, particularly wherein the MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and BODIPY™ analogs, and said Q portion is a member selected from the group consisting of mono azo and bis azo dyes.

In still another related aspect, the present invention provides methods for distinguishing between wild-type, mutant and heterozygous target polynucleotides, said method comprising:

(a) contacting a sample containing a target polynucleotide with two probes wherein a first probe is specific for said wild-type target polynucleotide and a second probe is specific for said mutant target polynucleotide, each of said probes having a formula:

wherein MB is a minor groove binder, Q is a quencher, ODN is an oligonucleotide or modified oligonucleotide, K is a bond or a linking group, Fl is a fluorophore and W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence of the fluorophore, more preferably less than 5%, still more preferably less than 2% and in the most preferred embodiments is less than 1%; and iii) when said oligonucleotide conjugate hybridizes to said target sequence, the fluorescence of Fl is at least 50% of its unquenched fluorescence, more preferably at least 60%, still more preferably at least 80% and in the most preferred embodiments is at least 90%; and wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence or absence of each of said wild-type, mutant and heterozygous target polynucleotides. In this aspect, the melting temperatures ($T_m$) for each hybrid produced between said first and second probes and their respective targets are preferably within about 5° C. of each other. In other selected embodiments, the ODN portion of each of said probes is an oligonucleotide or modified oligonucleotide having from 8 to 18 bases or modified bases. Still more preferably, the ODN portion of each of said probes is an oligonucleotide or modified oligonucleotide having from 10 to 15 bases or modified bases. In other preferred embodiments, the fluorophore portions of each of said probes are selected from the group consisting of 5-FAM™, 6-FAM™, TET™, JOE™, HEX™, VIC™, NED™, TAMRA™, ROX™ and YY™. In still other preferred embodiments, the ODN portion of each of said probes contains at least one modified base. In still other embodiments, the sample is further contacted with a set of primers under amplification conditions and each of said primers contains from one to ten modified bases selected from those described herein.

In addition to the embodiments described above, preferred components (e.g., MB, Fl, W, ODN, K and Q) for use in the recited probes and methods are those components that have been described for the probes and conjugates of the invention. Accordingly, preferred probes and components are provided in, for example, formula II, IIIa, IIIb, IVa, IVb and IVc.

EXAMPLES

Materials and Methods

Templates

One hundred and two unrelated Centre Etude Polymorphism Humaine (CEPH) DNA samples were obtained from the Coriell Institute of Medical Research (http://locus.umd-nj.edu/). A list of the templates used, is available at http://snp500cancer.nci.nih.gov.

Oligonucleotides

PCR primers were synthesized using standard phosphoramidite chemistry. The MB-FI-5'-ODN-Q probes were prepared by automated DNA synthesis on a minor groove binder modified polystyrene support (compound 20, Scheme 4) using 5'-β-cyanoethyl phosphoramidites (Glen Research, VA) designed for synthesis of oligonucleotide segments in 5'→3' direction. Oligonucleotide synthesis was performed on an ABI 3900 synthesizer according to the protocol supplied by the manufacturer using a 0.02M iodine solution. Modified base phosphoramidites were synthesized based on methods previously disclosed (WO 03022859 and WO 0164958). The MGB ECLIPSE™ Probes were synthesized as described previously (Afonina et al, Biotechniques, 32, 940-949 (2002)). 6-Carboxyfluorescein (FAM), Yakima Yellow™ reporting dyes were introduced at the last step of the MB ECLIPSE™ probe synthesis using the corresponding phosphoramidites (Glen Research, Sterling, Va.). Phosphoramidite 41 was used for the incorporation of fluorescein group as shown in Reaction Scheme 8 into the probes of the invention. Epoch ECLIPSE™ Quencher CPG and 6-carboxyfluorescein (Glen Research, Stirling, Va.) were used for the synthesis of Molecular Beacons. Standard 5'-DMT phosphoramidites were used for the synthesis of the Molecular Beacons. All oligonucleotides were purified by reverse phase HPLC.

The ARNT-01 target sequence showing a [G/C] polymorphism, designed probe and primers are shown in Table 2

TABLE 2

Sequence of Target, Primer and Fluorogenic Probes

Portion of ARNT-01 Target (SEQ ID NO:15); Probe (SEQ ID NOS:16-19) and Primer Sequences are shown in Bold Underlined. FAM is fluorescein, YY is Yakima Yellow, Q is ECLIPSE ™ Quencher and MB is $DPI_3$ GTGTGCTGCCAAACCATTCAGACTGTGGCTGGTTCAAAACAGGAGTCACG
GAGTCAGA[G/C]ACATA*C*ACCACCCTGCCTGTCTCACATGAGACAATAA
ACAGAAAGCCATCTGCTGCCTCCAAGATCAAATGTTTCAGTTCCTGCGCA
AGAAAAAGAAATAGAA TABLE 2-continued Sequence of Target, Primer and Fluorogenic Probes Portion of ARNT-01 Target (SEQ ID NO:15); Probe (SEQ ID NOS:16-19) and Primer Sequences are shown in Bold Underlined. FAM is fluorescein, YY is Yakima Yellow, Q is ECLIPSE ™ Quencher and MB is $DPI_3$

| ECLIPSE ™ Probes | New Probes |
|---|---|
| MB-Q-GTATGTCTCTGACTCC-FAM | MB-FAM-GTATGTCTCTGACTCC-Q |
| MB-Q-GTATGTCTCTGACTCC-YY | MB-YY-GTATGTCTCTGACTCC-Q |

Real time PCR was conducted either in an ABI Prism® 7700 or an ABI Prism® 7900 instrument (Applied Biosystems, Foster City, Calif.). Fifty cycles of three step PCR (95° C. for 30 s, 56° C. for 30 s and 76° C. for 30 s) after 2 min at 50° C. and 2 min at 95° C. were performed. The reactions contained 0.25 µM MB-Fl-ODN-Q or MB ECLIPSE™ probe, 100 nM primer complementary to the same strand as the probe, 1 µM opposite strand primer, 125 µM dATP, 125 µM dCTP, 125 µM TTP, 250 µM dUTP, 0.25 U JumpStart DNA polymerase (Sigma), 0.125U of AmpErase Uracil N-glycosylase (Applied Biosystems) in 1X PCR buffer (20 mM Tris-HCl pH 8.7, 40 mM NaCl, 5 mM $MgCl_2$) in a 10 µL reaction. The increase in fluorescent signal was recorded during the annealing step of the reaction.

This example demonstrates the improved signal to background ratio for probes of the invention as compared to MB ECLIPSE™ probes. In order to do that fluorescence signal of free probes and probes after hybridization with synthetic complements were measured. The sequences of the probes and synthetic complements are shown in FIG. 3. The experiments were carried out on Varian Cary ECLIPSE™ fluorescence spectrophotometer with excitation either at 496 nm for FAM or at 530 nm for Yakima Yellow (YY) and an emission wavelength of ether 518 nm for FAM or 550 nm for YY. Excitation and emission slits of 5 nm were used. Background fluorescence was recorded in a solution containing 0.1 µM probe (either MB ECLIPSE™ or new probe of the invention), 40 mM NaCl, 5 mM $MgCl_2$, 10 mM Tris-HCl pH 8.7. For duplex formation 0.5 µM (final concentration) complement was added. Prior to the fluorescence measurement the reaction was pre-heated to 60° C. and then cooled to 20° C.

Figure 4:
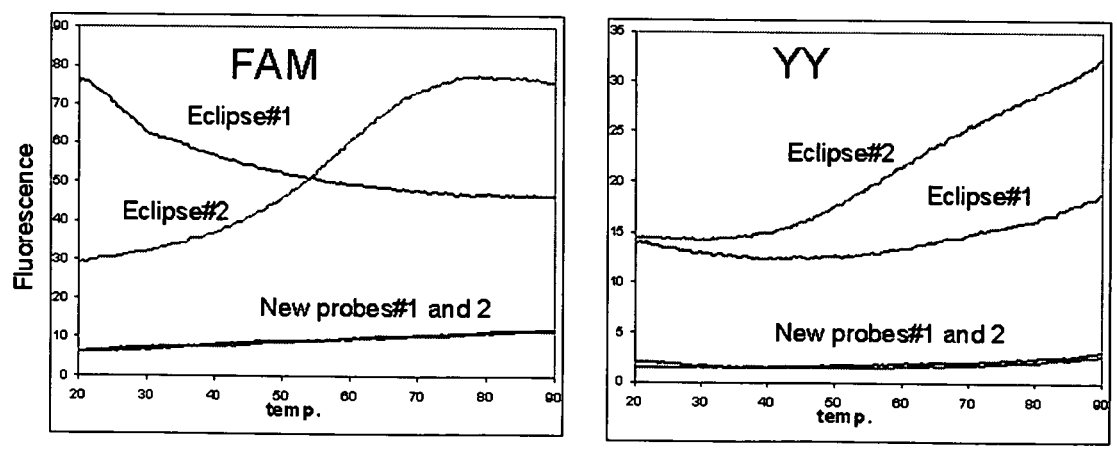
FIG. 4 compares the background signal stability with increase in temperature of two probes of the invention and two MGB ECLIPSE™ probes each of the two probes labeled with fluorescein (FAM) or Yakima Yellow (YY). Probe sequences: ECLIPSE™ #1 5'-CAGAGACATACA*CCA (SEQ ID NO:12), ECLIPSE™#2 5'-G*TATGTCTCTGACTCC (SEQ ID NO:9), New Probe #1 5'-G*TCAGAG*ACATACA*CC (SEQ ID NO:4), New probe #2 5'-G*TATGTCTCTGACTCC (SEQ ID NO:9). A* is 4-(4, 6-Diamino-1H-pyrazolo[3,4-d]pyrimidin-3-yl)-but-3-yn-1-ol and G* is 6-amino-1H-pyrazolo[3,4-d]pyrimidin-4(5H)-one.

This example illustrates improved stability of background fluorescence (fluorescence of unhybridized probe) of the probes of the invention in comparison to MGB ECLIPSE™ probes as a function of temperature (see FIG. 4). The experiments were carried out on Varian Gary ECLIPSE™ fluorescence spectrophotometer equipped with a temperature controlled cell with excitation either at 496 nm for FAM or at 530 nm for Yakima Yellow (YY) and an emission wavelength of ether 518 nm for FAM or 550 nm for YY. Excitation and emission slits of 5 nm were used. Solutions contained 0.2 µM probe (either MB ECLIPSE™ or new probe of the invention), 40 mM NaCl, 5 mM $MgCl_2$, 10 mM Tris-HCl pH 8.7.

Probe sequences (SEQ ID NOS:20-23):

Eclipse#1 MB-Q-5'-CAGAGACATACA*CCA-FAM (or YY)

Eclipse#2 MB-Q-5'-G*TATGTCTCTGACTCC-FAM (or YY)

New Probe#1   MB-FAM(or YY)-5'-G*TCAGAG*ACATACA*CC-Q
New probe#2   MB-FAM(or YY)-5'-G*TATGTCTCTGACTGC-Q
G* is PPG, A* is hydroxybutynyl-diaminopyrazolopyrimidine modified base.

Figure 5:
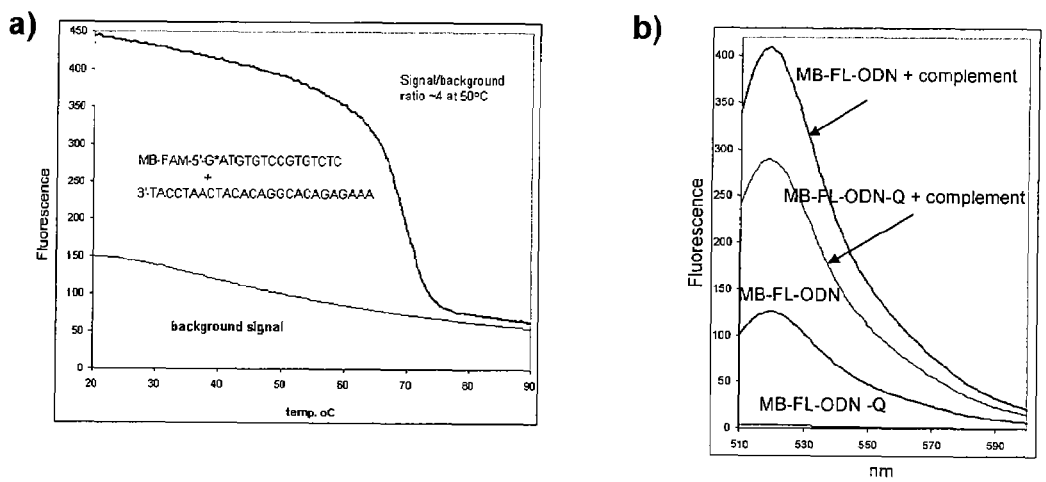
FIG. 5a shows the change of fluorescent background with temperature of a MB-Fl-ODN (SEQ ID NO: 13) in solution and bound to its complementary target (SEQ ID NO: 14).
FIG. 5b shows the fluorescence spectra of MB-Fl-ODN and MB-Fl-ODN-Q in solution and bound to their complementary sequence.

This example demonstrates a) the ability of conjugated minor groove binder to quench fluorescence and b) concerted fluorescence quenching mechanism involving both the minor groove binder and ECLIPSE™ Quencher (see FIG. 5). The experimental conditions were as described in Example 1 and 2.

Probe sequences (SEQ ID NOS:24 and 13):
MB-FAM-5'-G*ATGTGTCCGTGTCTC-Quencher or no quencher
Complement sequence (SEQ ID NO:14):
3'-TACCTAACTACACAGGCACAGAGAAA This example illustrates the increased sensitivity of the new probe of the invention by comparing its melting performance to a MGB ECLIPSE™ probe at constant probe concentration of $2\times10^{-7}$ M, while the complement concentration was varied between $1\times10^{-7}$ and $2.5\times10^{-10}$ M.

The probes and complement sequence are shown below:
New probe and complement sequences (SEQ ID NOS:24 and 14):

```
MB-FAM-gATGTGTCCGTGTCTC-Q      New Probe
3'TACCTAACTACACAGGCACAGAGAAA   Complement 1
```

MGB ECLIPSE™ probe and complement sequences (SEQ ID NOS:25 and 14):

```
MB-Q-gATGTGTCCGTGTCTC-FAM      MGB ECLIPSE ™
3'TACCTAACTACACAGGCACAGAGAAA   Complement 1
```

Figure 8:
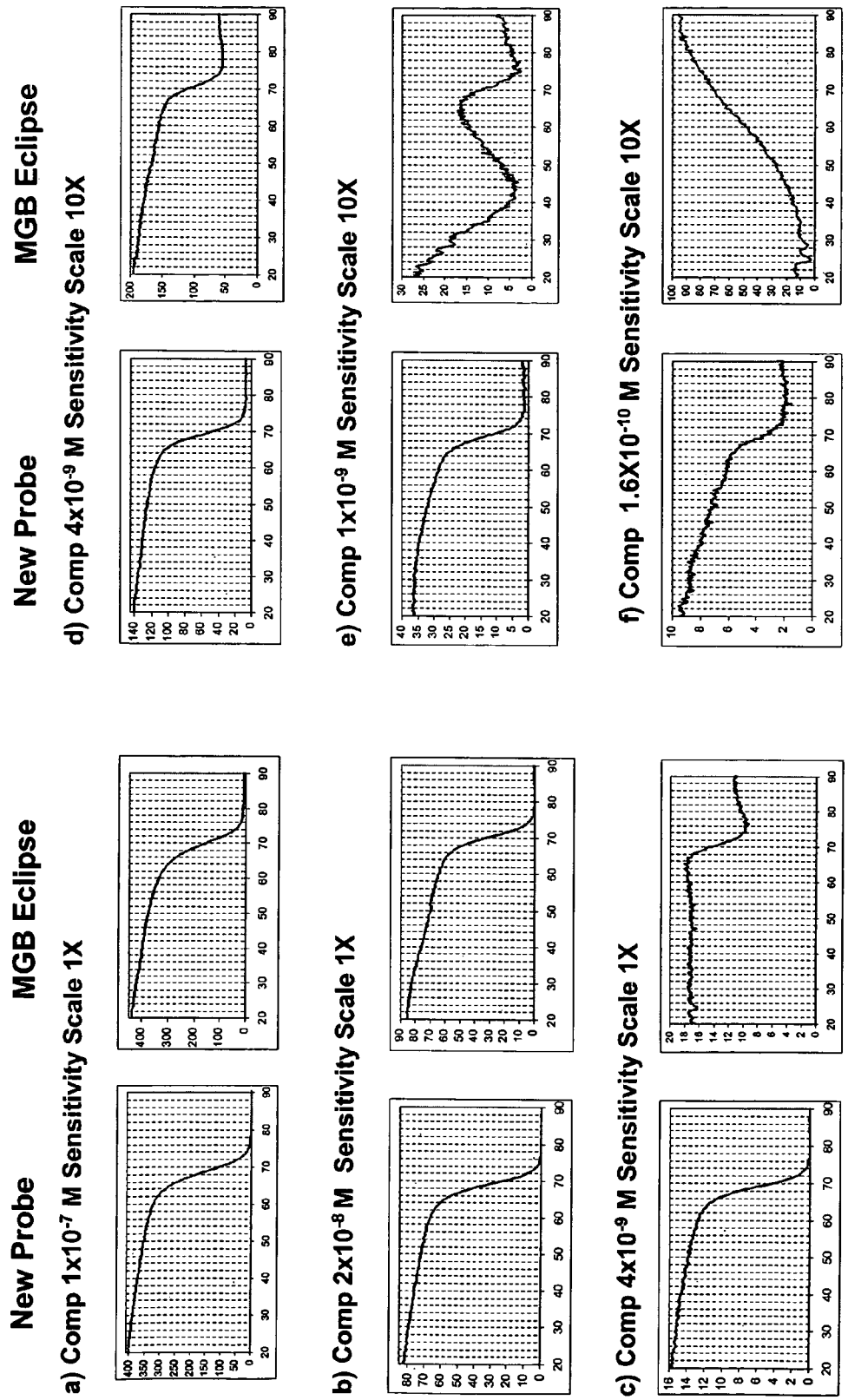
FIG. 8 shows a melting curve comparison of the performance of the new probe with MGB ECLIPSE™ Probe. A. Represents the comparison of the new probe in the left column with the MGB ECLIPSE™ probe in the right column at three different complement concentrations (a) $1\times10^{-7}$M, b) $2\times10^{-8}$M and c) $4\times10^{-9}$M) as indicated on the each graph and a constant probe concentration of $2\times10^{-7}$ M). B. Represents the comparison of the new probe in the left column with the MGB ECLIPSE™ probe in the right column at three different complement concentrations (a) $4\times10^{-9}$M, b) $1\times10^{-9}$M and c) $1.6\times10^{-10}$M) at a constant probe concentration of $2\times10^{-7}$ M. Note that the sensitivity gain was increase 10 fold.

The fluorogenic melting analysis was performed in 1x PCR buffer in a Varian Cary fluorescence spectrophotometer using excitation wavelength of 496 nm and an emission wavelength of 518 nm, with excitation slit of 5 nm and emission slit of 5 nm. Different probe/complement duplexes were formed at constant probe concentration of $2\times10^{-7}$ M, while the complement concentration varied between $1\times10^{-7}$ and $2.5\times10^{-10}$ M. The melt curve comparison for the performance of the new probe of the invention and MB ECLIPSE™ probe is shown in FIG. 8. This figure shows a substantial increase in sensitivity based on the melting curve comparison of these two probe types' performance.

Example 5

Figure 9:
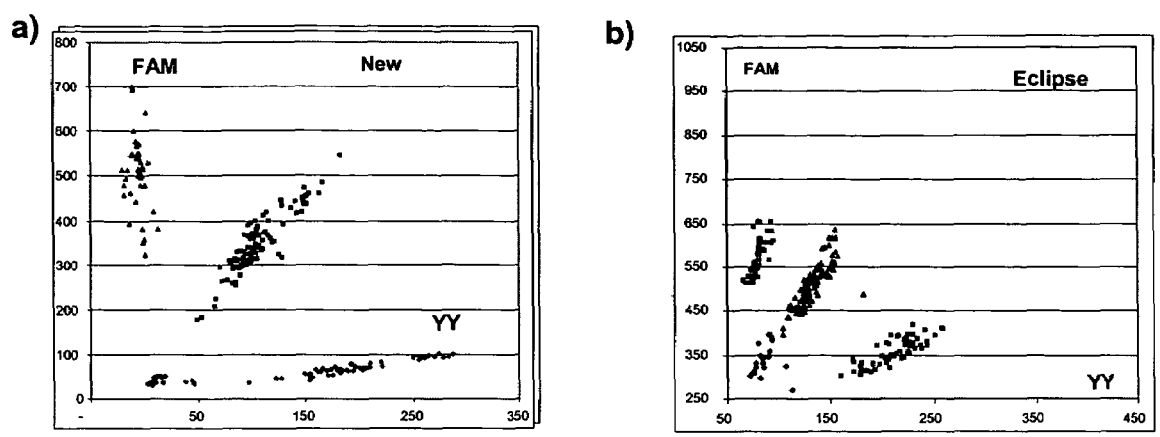
FIG. 9 shows genotyping scatter plots of real-time endpoint PCR analysis of 102 ARNT-01 DNA samples.

This example illustrates the ability of the probe assay of the invention to genotype. One hundred and two unrelated Centre Etude Polymorphism Humaine (CEPH) DNA samples were genotyped for the presence of the ARNT-01 allele (G/C) by comparison with the MB Eclipse and probe of invention assays. The corresponding probes specific for each mismatch are shown in Table 2. Each sample was analyzed with the probes specific for wild-type and mutant target in a PCR assay described above. The PCR-end-point scatter plot genotyping analysis of the DNA samples is shown in FIG. 9. The scatter plot of the assay of the invention (FIG. 9a) correctly genotype all the DNA samples with clear separation between no template controls, wild-type, heterozygote and mutant DNA samples. In contrast, the MB Eclipse assay (FIG. 9b), the no-template control and heterozygote DNA samples are not clearly separated.

Example 6

Hybridization Kinetic Comparison of Probes of the Invention and Molecular Beacons This example shows that the probes of the invention hybridize significantly faster than molecular beacons to their respective targets. The hybridization kinetics of new probes and Molecular beacons were investigated with a rapid kinetics spectrophotometer accessory (Applied Photophysics, Surrey, UK) over a temperature range (30-55° C.). The probe and target concentrations were $1\times10^{-7}$ and $2\times10^{-7}$ M, respectively. The sequences of the probes and target are (SEQ ID NOS:26-28):

MB-FAM-gTCAGAgACATACaCC-Q (Probe of the invention),

FAM-CGGCGAGTCAGAGACATACACCAGCCG-Q (Molecular Beacon probe) and

GCAGGGTGGTGTATGTCTCTGACTCCGTG (Target Complement). The stem sequences are underlined and "a" and "g" are Super A and Super G, respectively.

| Temp °C. | Probe of invention (P) Reaction Rate Constant L * Mol$^{-1}$ * sec$^{-1}$ | Molecular Beacon (M) Reaction Rate Constant L * Mol$^{-1}$ * sec$^{-1}$ | Reaction Rate Ratio P/M |
|---|---|---|---|
| 30 | $0.41 \times 10^5$ | $0.10 \times 10^5$ | 4.05 |
| 40 | $1.61 \times 10^5$ | $0.27 \times 10^5$ | 6.00 |
| 45 | $2.84 \times 10^5$ | $0.54 \times 10^5$ | 5.27 |
| 50 | $4.35 \times 10^5$ | $1.00 \times 10^5$ | 4.347 |
| 55 | $6.51 \times 10^5$ | $2.45 \times 10^5$ | 2.66 |

Example 7

This example illustrates the synthesis of PFP activated solid support 7.

tert-Butyl 4-chlorobutyrate

A mixture of 4-chlorobutyryl chloride (93 g, 0.66 mol), N,N-dimethylaniline (80 g, 0.66 mol) and tert-butanol (0.66 mol) in ethyl ether (100 mL) was refluxed for 5 h. The reaction was cooled, diluted with ether and washed with water, 10% citric acid, saturated NaCl and dried over Na$_2$SO$_4$. Crude product obtained after evaporation of the solvent was distilled under vacuum (10 mmHg). Pure product (79 g, 67%) boiling at 57-58° C. was collected. $^1$H NMR (DMSO-d$_6$) δ 3.64 (t, J=7 Hz, 2H), 2.35 (t, J=7 Hz, 2H), 1.93 (q, 2H), 1.41 (s, 9H).

3-[(tert-Butyl)oxycarbonyl]propyl phenylmethyl butane-1,4-dioate 3

A solution of tert-butyl 4-chlorobutyrate (8.9 g, 50 mmol) and cesium monobenzylsuccinate (prepared from monobenzyl succinate and CsOH) (50 mmol) in 100 mL of DMF was heated at 80° C. for 2 days. DMF was evaporated and chromatographed on silica (hexane-ethyl acetate) to afford 2.5 g (14%) of the title compound 3 as a colorless liquid. $^1$H NMR (DMSO-d6) δ 7.35 (s, 5H), 5.09 (s, 2H), 3.99 (t, J=7 Hz, 2H), 2.58 (m, 4H), 2.25 (t, J=7 Hz, 2H), 1.93 (q, 2H), 1.41 (s, 9H).

3-[(tert-Butyl)oxycarbonyl]propyl 2,3,4,5,6-pentafluorophenyl butane-1,4-dioate 4

Compound 3 (2.0 g, 5.7 mmol) was hydrogenated for 20 h at 40 psi in THF (100 mL) in the presence of 0.2 g of 10% Pd/C. The catalyst was removed by filtration through Celite and filtrate concentrated. The acid was dissolved in 20 mL of anhydrous $CH_2Cl_2$. Diisopropylethylamine ((0.88 g, 6.8 mmol) was added followed by pentafluorophenyl trifluoroacetate (1.9 g, 6.8 mmol). After being kept at room temperature for 1 h solvent was evaporated and residue chromatographed on silica (ethyl acetate-hexane) to afford 2.2 g (91%) of 4 as viscous liquid. $^1$H NMR (DMSO-$d_6$) δ 4.05 (t, J=6 Hz, 2H), 3.04 (t, J=6 Hz, 2H), 2.72 (t, J=6 Hz, 2H), 2.26 (t, J=7 Hz, 2H), 1.78 (q, 2H), 1.38 (s, 9H).

Preparation of PFP Activated Solid Support 7

Long chain alkylamine (LCAA) CPG (5.0 g, 500A, 124 mmol/g) was added to a solution of 4 (0.53 g, 1.24 mmol) and diisopropylethylamine (1 mL) in 25 mL of DMF. The CPG was swirled for 30 h. Pyridine (10 mL) and acetic anhydride (5 mL) were added and the CPG was swirled for another 1 h. The CPG was washed with DMF and ether. Drying under vacuum afforded 5.

CPG 5 (5.0 g) was suspended in 25 mL of TFA. After being swirled for 1 h it was washed with $CH_2Cl_2$. Drying yielded CPG 6.

Support 6 (5.0 g) was suspended in 25 mL of anhydrous $CH_2Cl_2$ and treated with diisipropylethylamine (2 mL) and PFP-TFA (1 mL). The support was swirled for 1 h. Excess reagents and by-products were removed by filtration and washing with $CH_2Cl_2$. Drying afforded PFP activated CPG 7.

Example 8

3-[(Fluoren-9-ylmethyl)oxycarbonyl]pyrrolo[3,2-e]indoline-7-carboxylic acid 9

3-(tert-Butyloxycarbonyl)pyrrolo[3,2-e]indoline-7-carboxylic acid 8 (Boger et. al, *J. Org. Chem.* 52:1521 (1987)) (0.76 g, 2.4 mmol) was deprotected by a treatment with 5 mL of TFA for 1 h. TFA vas evaporated and the resultant trifluoroacetate dissolved in a mixture of 11% $Na_2CO_3$ (10 mL) and 5 mL of THF. 9-Fluorenylmethyl chloroformate (0.75 g, 2.9 mmol) was added and the reaction mixture was stirred for 3 h. The reaction was diluted with water (200 mL) and extracted with ethyl ether (2×50 mL). The aqueous phase was acidified by adding 1N HCl to pH 1-2. Precipitated product was collected by centrifugation, washed with water and dried under vacuum to afford 0.86 g (83%) of 9 as a yellow-gray solid.

2,3,4,5,6-Pentafluorophenyl 3-[(fluoren-9-ylmethyl)oxycarbonyl]pyrrolo[4,5-e]indoline-7-carboxylate 10

Pentafluorophenyl trifluoroacetate (0.3 mL, 1.75 mmol) was added to a solution of acid 9 (0.3 g, 0.7 mmol) and triethylamine (0.3 mL, 2.1 mmol) in 4 mL of anhydrous DMF. After 1 h DMF was evaporated and the residue chromatographed on silica eluting with 2% acetone in methylene chloride. Concentration of the pure product fraction and drying afforded 0.29 g (70%) of PFP ester 10 as a yellow solid.

Synthesis of Compound 11

A solution of 10 (1.2 g, 2.0 mmol) and mono-O-DMT-4-aminobutyryl-1,3-propanediol (see, U.S. Pat. No. 5,942,610) (1.2 g (2.66 mmol) in 20 mL of pyridine was kept at room temperature for 24 h. The reaction was concentrated re-dissolved in ethyl acetate, washed with saturated NaCl and dried over $Na_2SO_4$. Crude product was chromatographed on silica eluting with ethyl acetate. Evaporation of the solvet afforded 1.6 g (93%) of desired compound 11.

Example 9

This example illustrates the preparation of solid support 20.

Methyl 3-{6-[bis(4-methoxyphenyl)phenylmethoxy]hexanoyl}pyrrolo[4,5-e]indoline-7-carboxylate 15

A solution of methyl pyrrolo[4,5-e]indoline-7-carboxylate (2.7 g, 12.5 mmol) prepared according to Boger et al (*J. Org. Chem.* 52:1521 (1987)), 4-nitrophenyl 4-[bis(4-methoxyphenyl)phenylmethoxy]hexanoate (6.9 g, 12.5 mmol) and triethylamine (2 mL) in 50 mL of anhydrous DMF was stirred at room temperature for 5 h and then concentrated. The resulting oil was left at room temperature overnight (~15 h). The oil was partitioned between ethyl acetate and 5% sodium bicarbonate. The organic phase was washed twice with diluted sodium bicarbonate, saturated sodium chloride and dried over sodium sulfate. The crude product obtained after removal of the solvent was crystallized from ethyl acetate. The yield of the crystalline product 15 was 5.9 g (75%). $^1$H NMR (DMSO-d6) δ 11.94 (s, 1H), 8.24 (d, J=9 Hz, 1H), 7.4-7.2 (m, 10H), 7.07 (s, 1H), 6.87 (d, J=9 Hz, 4H), 4.16 (t, J=8 Hz, 2H), 3.87 (s, 3H), 3.72 (s, 6H), 3.28 (t, J=8 Hz, 2H), 2.96 (t, J=6 Hz, 2H), 2.42 (t, J=7 Hz, 2H), 1.58 (m, 4H), 1.41 (m, 2H).

2,3,4,5,6-Pentafluorophenyl 3-{6-[bis(4-methoxyphenyl)phenylmethoxy]hexanoyl}pyrrolo[4,5-e]indoline-7-carboxylate 16

A mixture of 15 (3.2 g, 5.06 mmol), lithium hydroxide monohydrate (0.6 g, 14.3 mmol) MeOH (10 mL), THF (20 mL) and water (10 mL) was stirred at 45° C. for 12 h and concentrated. The residue was partitioned between cold 10% citric acid and ethyl acetate. The organic phase was washed with saturated NaCl, dried over $Na_2SO_4$, treated with 5 mL of triethylamine and concentrated to afford 3.7 g of a solid material. The solid was co-evaporated with DMF (2×50 mL) to remove residual water and re-dissolved in 40 mL of anhydrous DMF. Diisopropylethylamine (1.5 mL) was added followed by pentafluorophenyl trifluoroacetate (PFP-TFA) (0.9 mL, 5.2 mmol). After being kept at room temperature overnight the reaction was concentrated and chromatographed on silica eluting with 1:1 hexane-ethyl acetate. Concentration of the pure product fractions and drying in vacuo afforded 2.5 g of 16 (69%) of the title compound as a pale yellow, amorphous solid. $^1$H NMR (DMSO-d6) δ 12.45 (s, 1H), 8.36 (d, J=9 Hz, 1H), 7.51 (s, 1H), 7.4-7.2 (m, 10H), 6.87 (d, J=9 Hz, 4H), 4.20 (t, J=8 Hz, 2H), 3.72 (s, 6H), 3.34 (t, J=8 Hz, 2H), 2.97 (t, J=6 Hz, 2H), 2.44 (t, J=7 Hz, 2H), 1.59 (m, 4H), 1.42 (m, 2H).

2-(4-Nitrophenyl)ethyl 3-({3-[(3-{6-[bis(4-methoxyphenyl)phenylmethoxy]hexanoyl}pyrrolo[4,5-e]indolin-7-yl)carbonyl]pyrrolo[4,5-e]indolin-7-ylycarbonyl)pyrrolo[4,5-e]indoline-7-carboxylate 18

To a solution of 2-(4-nitrophenyl)ethyl 3-(pyrrolo[4,5-e]indolin-7-ylcarbonyl)pyrrolo[4,5-e]indoline-7-carboxylate trifluoroacetate 17 (DPI$_2$ NPE ester, U.S. Patent Publication 20020034754) (0.91 g, 1.4 mmol) and diisopropylethylamine (0.49 mL, 2.8 mmol) in 10 mL of anhydrous DMF was added PFP ester 16 (1.1 g, 1.4 mmol). The reaction was kept at room temperature for 24 h to give a thick suspension of the precipitated product. Methanol (50 mL) was added and the precipitated product was collected by filtration and washed with methanol and ether. Drying under vacuum afforded 1.45 g (91%) of compound 18 as an off-white solid. $^1$H NMR (DMSO-d6) δ 11.99 (s, 1H), 11.78 (s, 1H), 11.70 (s, 1H), 8.4-8.1 (m, 5H), 7.67 (d, J=8.5 Hz, 2H), 7.5-7.2 (m, 12H), 7.09 (s, 2H), 7.01 (s, 1H), 6.88 (d, J=9 Hz, 4H), 4.6 (m, 6H), 4.16 (t, J=7.5 Hz, 2H), 3.73 (s, 6H), 3.43 (m, 4H), 3.31 (t, J=8 Hz, 2H), 3.23 (t, J=6 Hz, 2H), 2.97 (t, J=6 Hz, 2H), 2.41 (t, J=6 Hz, 2H), 1.59 (m, 4H), 1.41 (m, 2H).

Pentafluorophenyl 3-((3-[(3-{6-[bis(4-methoxyphenyl)phenylmethoxy]hexanoyl}pyrrolo[4,5-e]7-yl)carbonyl]pyrrolo[4,5-e]indolin-7-yl}carbonyl)pyrrolo[4,5-e]indoline-7-carboxylate 19

Nitrophenylethyl ester 18 (1.39 g, 1.22 mol) was deprotected by treatment with 6.6 mmol of DBU in 20 mL of anhydrous DMF for 2 h at 50° C. DMF was evaporated and the residue triturated with methanol. Insoluble material was collected by filtration washed with methanol and dried under vacuum overnight. The solid was re-dissolved in 20 mL of DMF and treated with diisopropylethylamine (1.5 mL, 8.6 mmol) and pentafluorophenyl trifluoroacetate (1.0 mL, 5.8 mmol). After being stirred at room temperature for 2 h DMF was evaporated and the residue triturated with methanol. Precipitated product was collected by filtration, washed with methanol and dried under vacuum to afford 1.41 g (100%) of the desired PFP ester 19 as a yellow solid. $^1$H NMR (DMSO-d6) δ 12.54 (s, 1H), 11.80 (s, 1H), 11.70 (s, 1H), 8.43 (d, J=9 Hz, 1H), 8.30 (m, 1H), 8.22 (d, J=9 Hz, 1H), 7.558 (s, 1H), 7.5-7.2 (m, 12H), 7.09 (s, 1H), 6.97 (s, 1H), 6.87 (d, J=9 Hz, 4H), 4.6 (m, 4H), 4.11 (t, J=7 Hz, 2H), 3.73 (s, 6H), 3.43 (m, 4H), 3.28 (t, J=8 Hz, 2H), 2.97 (t, J=6 Hz, 2H), 2.37 (t, J=6 Hz, 2H), 1.57 (m, 4H), 1.40 (m, 2H).

N-MMT-aminopentyl diglycolate CPG 22 was prepared by analogy with aminopropyl analog (U.S. patent application 2002/0034754)

5-[(4-Methoxyphenyl)diphenylamino]pentan-1-ol

A solution of monomethoxytrityl chloride (7.7 g, 24.9 mmol) in CH$_2$Cl$_2$ (50 mL) was added via addition funnel to a stirred, cold (ice/water) solution of 5-amino-1-pentanol (5.2 g, 50 mmol) in another 50 mL of anhydrous CH$_2$Cl$_2$. The mixture was warmed up to room temperature and allowed to react for 1 h. The reaction was diluted with more CH$_2$Cl$_2$ and extracted with water. The organic phase was washed with saturated NaCl and dried over Na$_2$SO$_4$. Crude product obtained after evaporation of the solvent was chromatographed on silica (ethyl acetate-hexane) to afford 6.1 g of 5-[(4-methoxyphenyl)diphenylamino]pentan-1-ol 2-{[(5-{[(4-Methoxyphenyl)diphenylmethyl]amino}pentyl)oxycarbonyl]methoxy}acetic acid, triethylammonium salt 21

3.0 g (8 mmol) of the 5-[(4-methoxyphenyl)diphenylamino]pentan-1-ol was dissolved in 20 mL of methylene chloride with 1.3 mL (9.4 mmol) of triethylamine and 1.1 g (9.5 mmol) of diglycolic anhydride. The mixture was stirred overnight and concentrated. The residue was chromatographed on silica eluting with 93% methylene chloride, 5% methanol and 3% triethylamine. The fractions containing products were combined and solvent was evaporated. Traces of water were removed by co-evaporation with dry DMF. Yield of the product was assumed to be 100%. It was dissolved in 24 mL of DMF to ~0.33 M final concentration.

Synthesis of N-MMT-aminopentyl diglycolate CPG 22.

10 g of LCAA-CPG was combined with 5 mL of a 0.33 M solution of 21 in DMF (1.66 mmol) in a 100 mL round bottom flask. A solution of 2.5 mL of diisopropylethylamine, 0.11 g (0.8 mmol) of HOBT and 0.63 g (1.66 mmol) of HBTU was prepared and added to the CPG. The CPG was swirled for 16 h on an orbital shaker (150 rpm). The CPG was filtered on a sintered glass funnel and washed with DMF (2×100 mL), acetonitrile (2×100 mL) and ether (2×100 mL). After being dried in vacuo, unreacted aminogroups were capped by treating the CPG with 40 mL of pyridine and 5 mL of acetic anhydride. After swirling for 2 h, the CPG was filtered and washed as described above. After drying in vacuo overnight the CPG was analyzed for MMT loading by treating 3-5 mg of CPG in 25 mL of 1:1 (70% perchloric acid:methanol). The absorbance of the released MMT cation was recorded at 472 nm and loading was calculated according to the equation:

$$\text{MMT loading}(\mu\text{mol/g}) = A_{472}\text{ nm} \times \text{volume}(\text{mL}) \times 14.3 / \text{wt of } CPG(\text{mg})$$

MGB Ligand Support 20

4 g of N-MMT-aminopentyl diglycolate CPG 22 was weighed into a medium porosity sintered glass funnel. The CPG was detritylated by treating with 25 mL of 3% TCA/DCM. After stirring briefly with a spatula, the mixture reacted for 5 min before filtering (turned yellow). The process was repeated 4 times until the filtrate was colorless. The CPG was washed with 4×40 mL of methylene chloride. The filtrate was discarded to organic waste, and the CPG was neutralized by treatment with 40 mL of 20% triethylamine in acetonitrile. After briefly stirring with a spatula, the mixture was filtered and washed with 2×40 mL of acetonitrile, and 2×40 mL of ether. Traces of ether were removed in vacuo (oil pump). The de-tritylated CPG was used immediately for the following immobilization reaction.

MGB PFP ester 19 (0.20 g, 180 μmol) of was shaken with 12 mL of dry DMSO. After 15 min, the solution was added to 4 g of detritylated diglycolate CPG (in a 50 mL round bottom flask). Two mL of triethylamine was added and the mixture was stoppered and swirled on an orbital mixer for 14 h. The CPG was filtered and washed with 2×50 mL of DMSO, 2×50 mL of acetonitrile, and 2×50 mL of ether. Traces of ether were removed in vacuo (oil pump). Unreacted amino groups were acetylated by treating the CPG with 10 mL of dry pyridine, 1 mL of 1-methylimidazole and 1 mL of acetic anhydride. After swirling for 1 h, the CPG was filtered and washed with 2×50 mL of DMF, 2×50 mL of acetonitrile, and 2×50 mL of ether. Traces of ether were removed in vacuo (oil pump). The CPG was analyzed for DMT loading by treating 3-5 mg of CPG in 25 mL of 1:1/70% perchloric acid:methanol. The absorbance of the released DMT cation was recorded at 498 nm and loading level was calculated to be 45 μmol/g of CPG using the equation:

$$\text{DMT loading }(\mu\text{mol/g}) = A_{498} \times \text{volume (in mL)} \times 14.3 \div \text{wt of } CPG(\text{mg})$$

Example 10

This example illustrates the preparation of phosphoramidite 31

Methyl 5-{2-[2-(2-{2-[2-(2-hydroxyethoxy)ethoxy]ethoxy}ethoxy)ethoxy]ethoxy}-3-(methoxycarbonyl)benzoate 23

Diethylazodicarboxylate (22.7 g, 130 mmol) was added over 3 min to a stirred solution of dimethyl 5-hydroxyisophthalate (21 g, 100 mmol), hexaethylene glycol (32 g, 113 mmol) and triphenylphosphine (34 g, 130 mmol) in 250 mL of anhydrous THF. After 2 h the reaction was concentrated and the residue suspended in 200 mL of ethyl ether. After being cooled at 0° C. for 30 min the precipitated triphenylphosphine oxide was removed by filtration and filtrate concentrated. The resultant mixture was chromatographed on silica eluting, first, with ethyl acetate to separate $Ph_3PO$ and symmetrical bis-substituted hexaethylene glycol by-product and, second, with 5% MeOH in ethyl acetate to elute desired mono-substituted hexaethylene glycol derivative. Evaporation of the solvent and drying under high vacuum afforded 14.8 g (31%) of the title compound as viscous oil. $^1$H NMR (DMSO-d6) δ 8.08 (s, 1H), 7.70 (s, 2H), 4.58 (t, J=5.5 Hz, 1H), 4.25 (m, 2H), 3.90 (s, 6H), 3.76 (m, 2H), 3.60 (m, 2H), 3.51 (m, 16H), 3.40 (m, 2H).

Methyl 5-{2-[2-(2-{2-[2-(2-azidoethoxy)ethoxy]ethoxy}ethoxy)ethoxy]ethoxy}-3-(methoxycarbonyl)benzoate (25)

p-Toluene sulfonyl chloride (7.1 g, 37.44 mmol) was added in one portion to a stirred, cold (ice/water bath) solution of 23 (14.8 g, 31.2 mmol) in 100 mL of anhydrous pyridine. After being kept at 0° C. overnight the reaction was concentrated to ~30 mL without using heating bath and partitioned between ethyl acetate (200 mL) and 3N $NaHSO_4$ (200 mL). Aqueous phase was washed with extra amount of ethyl acetate (100 mL) and combined organic washings were washed with saturated NaCl and dried over $Na_2SO_4$. Concentration afforded crude 17.8 g of tosylate 24 as viscous oil. This product was used in the next step without additional purification.

Sodium azide (4.0 g, 61.5 mmol) was added to a solution of crude tosylate 24 (17.8 g, 28.3 mmol) in 220 mL of anhydrous DMF. The reaction was stirred at 50° C. for 5 h. Solvent was evaporated and the residual material partitioned between water (100 mL) and ethyl acetate (200 mL). The organic phase was washed with saturated NaCl and dried over $Na_2SO_4$. Crude product obtained after solvent evaporation was chromatographed on silica eluting with ethyl acetate. Product containing fractions were concentrated and dried under vacuum to afford 10.1 g (67%) of desired azide 25 as a colorless, viscous oil. $^1$H NMR (DMSO-d6) δ 8.08 (s, 1H), 7.70 (s, 2H), 4.24 (t, J=4 Hz, 2H), 3.90 (s, 6H), 3.78 (t, J=4 Hz, 2H), 3.59 (t, J=5 Hz, 2H), 3.51 (m, 16H), 3.38 (t, J=5 Hz, 2H).

N-[2-(2-{2-[2-(2-{2-[3,5-Bis(hydroxymethyl)phenoxy]ethoxy}ethoxy)ethoxy]ethoxy}ethoxy)ethyl](fluoren-9-ylmethoxy)carboxamide (27)

Lithium aluminum hydride (10.0 g, 263.5 mmol) was suspended in 250 mL of anhydrous THF under argon in three portions. The suspension was cooled to 0° C. (ice/water bath) and a solution of azide 25 (10.1 g, 20.2 mmol) in 100 mL of dry THF was added slowly (~5 min) with stirring. The reaction was allowed to warm to room temperature and stirring was continued for another 2 h. Excess $LiAlH_4$ was quenched by dropwise (very slow at the beginning) addition of water (20 mL) and the reaction mixture was concentrated to give a semi-solid material. Desired aminodiol was isolated from this material by extraction with 2-propanol and filtration. Solids were washed with additional 2-propanol until no product was detected in washings (4×200 mL). Concentration of the extract afforded crude aminodiol 26 (8.2 g), it was utilized in the next step without additional purification.

To a stirred, cold (ice/water bath) solution of crude amine 26 (8.2 g, 19.6 mmol) in 80 mL of DMF was added N,N-diisopropylethylamine (2.6 g, 20 mmol) followed by 9-fluorenylmethyl chloroformate (5.2 g, 20 mmol). The reaction was stirred at 0° C. for 30 min. DMF was evaporated and the resultant oil was partitioned between ethyl acetate (300 mL) and water (100 mL). The aqueous phase was washed with additional ethyl acetate. Combined organic phases were washed with saturated NaCl, dried over $Na_2SO_4$ and concentrated. The mixture was chromatographed on silica eluting with $CH_2Cl_2$ followed by 2.5% MeOH/$CH_2Cl_2$, 5% MeOH/$CH_2Cl_2$ and, finally, with 10% MeOH/$CH_2Cl_2$. Concentration of the pure product fractions afforded 9.25 g (72%) of compound 27 as colorless, viscous syrup. $^1$H NMR (DMSO-d6) δ 7.89 (d, J=7.4 Hz, 2H), 7.70 (d, J=7.2 Hz, 2H), 7.42 (t, J=7.4 Hz, 2H), 7.33 (t, J=7.1 Hz, 2H), 6.86 (s, 1H), 6.75 (s, 2H), 5.16 (t, J=5.8 Hz, 2H), 4.45 (d, J=5.8 Hz, 4H), 4.30 (m, 2H), 4.22 (m, 1H), 4.06 (t, J=4 Hz, 2H), 3.72 (t, J=4.7 Hz, 2H), 3.5 (m, 16H), 3.41 (t, J=6.3 Hz, 2H), 3.15 (m, 2H).

N-(2-{2-[2-(2-{2-[2-(5-{[Bis(4-methoxyphenyl)phenylmethoxy]methyl}-3-(hydroxymethyl)phenoxy)ethoxy]ethoxy}ethoxy)ethoxy]ethoxy}ethyl) fluoren-9-ylmethoxy)carboxamide (28)

Dimethoxytrityl chloride (6.66 g, 19.6 mmol) was added in one portion to stirred, cold (ice/water bath) solution of diol 27 (12.6 g, 19.7 mmol) in 175 mL of anhydrous pyridine. The reaction was allowed to warm to room temperature. After being kept at room temperature for 15 h the reaction was concentrated and partitioned between ethyl acetate and cold 10% citric acid. The organic phase was washed with saturated NaCl and dried over $Na_2SO_4$. Desired mono-DMT substituted diol 28 was isolated from the mixture by silica gel column purification eluting with a gradient of MeOH (from 0 to 10%) in ethyl acetate. Concentration of the pure product fractions and drying under vacuum afforded 8.0 g (43%) of the title compound 28 as a very viscous syrup. $^1$H NMR (DMSO-d6) δ 7.89 (d, J=7.4 Hz, 2H), 7.69 (d, J=7.2 Hz, 2H), 7.5-7.2 (m, 13H), 6.92 (d, J=8.8 Hz, 4H), 6.89 (s, 1H), 6.81 (s, 1H), 6.74 (s, 1H), 5.19 (t, J=6 Hz, 1H), 4.47 (d, J=6 Hz, 2H), 4.29 (m, 2H), 4.21 (m, 1H), 4.05 (m, 4H), 3.74 (s+m, 8H), 3.5 (m, 16H), 3.41 (t, J=6.3 Hz, 2H), 3.14 (m, 2H).

5-[N-(2-{2-[2-(2-{2-[2-(5-{[Bis(4-methoxyphenyl)phenylmethoxy]methyl}-3-(hydroxymethyl)phenoxy)ethoxy]ethoxy}ethoxy)ethoxy]ethoxy}ethyl)carbamoyl]-15-(2,2-dimethylpropanoyloxy)-1-oxospiro[3-hydroisobenzofuran-3,9'-xanthene]-12-yl 2,2-dimethylpropanoate (30)

DBU (3 mL, 20 mmol) was added to a stirred solution of Fmoc protected monoDMT-aminodiol 28 in 100 mL of anhydrous $CH_2Cl_2$. After being stirred for 30 min the reaction mixture was concentrated and chromatographed on silica eluting with, first, $CH_2Cl_2$ to separate the protecting group and, second, with 10:5:85 (MeOH:$Et_3$N:$CH_2Cl_2$) to elute the desired product. Solvent was evaporated and the residue dried under vacuum to afford amine 29 as a viscous oil.

A solution of the amine 29 (2 mmol) and triethylamine (2 mmol) 30 mL of $CH_2Cl_2$ was added to a stirred, cold (0° C.) solution of pentafluorophenyl dipivaloylfluorescein-6-carboxylate (NUCLEOSIDE & NUCLEOTIDES (1997) 16(1 &2), 107-114) in 10 mL of anhydrous THF. After being stirred at 0° C. for 3 h, solvents were evaporated and residue chromatographed on silica eluting with a gradient of MeOH (0 to 5%) in ethyl acetate. Pure product fractions were concentrated and dried to afford 30 (2.1 g, 85%) as a colorless, amorphous solid. $^1$H NMR (DMSO-d6) δ 8.76 (t, J=5 Hz, 1H), 8.22 (d, J=8 Hz, 1H), 8.16 (d, J=8 Hz, 1H), 7.81 (s, 1H), 7.45 (s, 1H), 7.42 (s, 1H), 7.30 (m, 9H), 6.95 (m, 9H), 6.80 (s, 1H), 6.75 (s, 1H), 5.20 (t, J=6 Hz, 1H), 4.47 (d, J=6 Hz, 2H), 4.05 (m, 4H), 3.74 (s+m, 8H), 3.6-3.3 (m, 20H), 1.31 (s, 18H).

5-{N-[2-(2-{2-[2-(2-{2-[5-{[Bis(4-methoxyphenyl)phenyl-methoxy]methyl}-3-({[bis(methylethyl)amino](2-cyanoethoxy)phosphinooxy}methyl)phenoxy]ethoxy}ethoxy)ethoxy]ethoxy}ethoxy)ethyl]carbamoyl}-15-(2,2-dimethylpropanoyloxy)-1-oxospiro[3-hydroisobenzofuran-3,9'-xanthene]-12-yl 2,2-dimethylpropanoate (31)

To a solution of 30 (2.1 g, 1.68 mmol) in 50 mL of anhydrous $CH_2Cl_2$ was added diisopropylammonium tetrazolide (0.43 g, 2.5 mmol) followed by 2-cyanoethyl tetraisopropylphosphordiamidite (0.76 g, 2.5 mmol). The reaction was stirred overnight, concentrated and chromatographed on silica (pre-washed with $Et_3N$+EtOAc) eluting with ethyl acetate. Concentration of the pure product fractions and drying under high vacuum afforded 1.8 g (75%) of 31 as a colorless, amorphous solid. $^1H$ NMR (DMSO-d6) δ 8.76 (t, J=5 Hz, 1H), 8.22 (d, J=8 Hz, 1H), 8.15 (d, J=8 Hz, 1H), 7.80 (s, 1H), 7.44 (s, 1H), 7.41 (s, 1H), 7.30 (m, 9H), 6.95 (m, 9H), 6.80 (s, 1H), 6.75 (s, 1H), 4.66 (m, 2H), 4.03 (m, 4H), 3.74 (s+m, 8H), 3.6-3.3 (m, 24H), 2.75 (t, J=6 Hz, 2H), 1.29 (s, 18H), 1.14 (t, J=7 Hz, 12); $^{31}P$ NMR δ 148 (s).

Example 11

This example illustrates the preparation of phosphoramidite 41.

Synthesis of Compound 32

Diethylazodicarboxylate (DEAD) (20.5 mL, 0.13 mol) was added drop-wise to a stirred solotuon of methyl 4-hydroxybenzoate (15.2 g, 0.1 mol), hexa(ethyleneglycol) (32 g, 0.11 mol) and triphenylphosphine (34 g, 0.13 mol) in 200 mL of anhydrous THF. After being stirred for 2 h the reaction was concentrated and residue suspended in ether (200 mL) to precipitate triphenylphosphine oxide. The suspension was cooled and the solid filtered off. The filtrate was concentrated and the resultant oil chromatographed on silica eluting with a gradient of methanol (0-5%) in ethyl acetate. Concentration of the pure product fraction and drying under vacuum afforded 11.9 g (29%) of 32 as a colorless syrup. $^1H$ NMR (DMSO-d6) δ 7.89 (d, J=8.8 Hz, 2H), 7.05 (d, J=8.8 Hz, 2H), 4.58 (t, J=5.5 Hz, 1H), 4.17 (t, J=4.5 Hz, 2H), 3.76 (t, J=4.5 Hz, 2H), 3.65-3.35 (m, 20H).

Synthesis of Compound 33

Compound 32 (12.9 g, 31.2 mmol) was dried by co-evaporation with anhydrous pyridine (2×100 mL), dissolved in 100 mL of anhydrous pyridine and cooled to 0-3° C. (ice-water bath). To this solution with stirring was added p-toluenesulfonyl chloride (7.1 g, 37.44 mmol) in one portion. The reaction was stirred at 0° C. for 16 h and concentrated keeping concentration flask cold (0-20° C.). The residue was partitioned between ethyl acetate (200 mL) and 3N $NaHSO_4$ (200 mL). The organic phase was washed with saturated $NaHCO_3$, NaCl and dried over $Na_2SO_4$. Concentration afforded 16.1 g of desired tosylate 33. This material was sufficiently pure to be used in the next reaction without additional purification.

Synthesis of Compound 34

Sodium azide (4.0 g, 61.5 mmol) was added to a solution of 33 (16.1 g, 28.2 mmol) in 220 mL of DMF. The reaction was stirred at 50° C. for 5 h. The solvent was evaporated and residue partitioned between water (100 mL) and ethyl acetate (200 mL). The organic phase was washed with saturated NaCl and dried over $Na_2SO_4$. The material obtained after solvent evaporation was chromatographed on silica eluting with ethyl acetate. Product containing fractions were concentrated to afford 10.5 g (85%) of the azide 34 as a colorless, viscous oil.

Synthesis of Compound 35

A solution of 34 (7.0 g, 15.9 mmol) in 250 mL of methanol was hydrogenated at 45 psi in the presence of 0.5 g of 10% Pd on carbon for 1 h. The catalyst was removed by filtration through Celite. Evaporation of the solvent afforded 6.55 g (99%) of amine 35 as a colorless, viscous oil.

Synthesis of Compound 36

Amine 35 (6.5 g, 15.6 mmol) was dissolved in 32 mL of 1 N NaOH. After being kept at room temperature for 1 h 50 mL of water and 15.6 mmol of $NaHCO_3$ was added. The solution was cooled to 0° C. using ice-water bath. To this solution was added a solution of Fmoc-Cl (4.9 g, 18.7 mmol) in 50 mL of THF. The resultant emulsion was stirred at 0° C. for 2 h, concentrated and acidified with 1N HCl to pH 2. The mixture was extracted with ethyl acetate. Organic was washed with saturated NaCl and dried over $MgSO_4$. Concentration gave viscous syrup which was chromatographed on silica eluting with a gradient of MeOH (0-5%) in dichloromethane. Yield of desired acid 36 was 9.1 g (93%).

Synthesis of Compound 37

To a solution of compound 36 (9.1 g, 14.6 mmol) and pyridine (1.5 mL) in 150 mL of anhydrous dichloromethane was added 2.6 mL (15.1 mmol) of pentafluorophenyl trifluoroacetate (PFP-TFA). The reaction was kept at room temperature for 3 h and concentrated. The residue was chromatographed on silica eluting with ethyl acetate. Concentration of the pure product fractions afforded 8.5 g (73%) of PFP ester 37 as a colorless, viscous oil. $^1H$ NMR (DMSO-d6) δ 8.10 (d, J=8.8 Hz, 2H), 7.87 (d, J=7.4 Hz, 2H), 7.68 (d, J=7.4 Hz, 2H), 7.40 (t, J=7.4 Hz, 2H), 7.31 (t, J=7.4 Hz, 2H), 7.18 (d, J=8.8 Hz, 2H), 4.25 (m, 5H), 3.77 (t, J=4.0 Hz, 2H), 3.60-3.50 (m, 6H), 3.49 (s, 10H), 3.40 (t, J=6.5 Hz, 2H), 3.13 (m, 2H).

Synthesis of Compound 39

A solution of 37 (4.0 g, 5.06 mmol), pyridine (0.5 mL), diisopropylethylamine (0.5 mL) and DMT-hydroxyprolinol (38) (2.5 g, 5.6 mmol) (prepared from N-FMOC-hydroxyproline by $BH_3$ reduction followed by DMT protection of the primary hydroxygroup) in 100 mL of dichloromethane was prepared. The reaction was allowed to proceed for to 50 h until almost no PFP ester 37 was found by TLC analysis (ethyl acetate). The solution was washed with 10% citric acid, saturated NaCl and dried over $Na_2SO_4$. Material obtained after solvent evaporation was chromatographed on silica eluting with a gradient of methanol (0 to 5%) in dichloromethane. Concentration of the pure product fractions afforded 4.7 g (90%) of the desired compound 39 as an amorphous, white solid.

Synthesis of Compound 40

A solution of compound 39 (4.6 g, 4.4 mmol) in a mixture of dichloromethane (25 mL) and thiethylamine (25 mL) was heated at 50° C. for 24 h. The reaction was concentrated and re-dissolved in 60 mL of anhydrous dichloromethane. Diisopropylethylamine was added and the solution was cooled to 0° C. (ice-water bath). To the cold solution was added in one portion pentafluorophenyl dipivaloylfluorescein-6-carboxylate (2.9 g, 4.08 mmol). The reaction was stirred at 0° C. for 1 h and concentrated. Resultant material was chromatographed on silica eluting with a gradient of methanol (0 to 2.5%) in dichloromethane. Product containing fractions were concentrated to give 4.8 g (88%) of 40 as an amorphous, white solid.

Synthesis of Compound 41

To a solution compound 40 (4.7 g, 3.5 mmol) in 80 mL of anhydrous dichloromethane was added 1.52 g of diisopropylammonium tetrazolide followed by 2-cyanoethyl tetraisopropylphosphorodiamidite (2.35 g, 7.8 mmol). After being stirred for 3 h, the reaction was concentrated and partitioned between ethyl acetate and 5% NaHCO$_3$. The organic phase was washed with saturated NaCl and dried over Na$_2$SO$_4$. The material obtained after solvet evaporation was precipitated twice from small amount of ethyl acetate into a large volume of anhydrous hexane. Trituration with hexane, filtration and drying afforded 4.6 g (86%) of desired phosphoramidite 41 as a white, amorphous solid.

What is claimed is:

1. An oligonucleotide-probe comprising an oligonucleotide portion having a 3'-end and a 5'-end, a minor groove binder moiety attached to at least one of said nucleotide units through a linking group which covalently binds the minor groove binder moiety to the oligonucleotide, and a fluorophore and quencher, said probe having the formula;

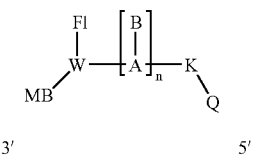

wherein MB is a minor groove binder; Q is a quencher; Fl is a fluorophore; [A-B]n represents an nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, and a peptidic backbone; and each B independently represents a nucleic acid base, a modified base or a base analog; K is a bond or a linking group; and W is a trivalent linking group that provides sufficient spacing between MB, Fl and [A-B]n such that (i) MB binds in a duplex minor groove formed when said oligonucleotide probe hybridizes to its complementary sequence; (ii) in an unhybridized form, the fluorescence of Fl in said oligonucleotide probe is less than 10% of unquenched fluorescence; and (iii) when said oligonucleotide probe hybridizes to said target sequence, the fluorescence of Fl is at least 50% of its unquenched fluorescence.

2. An oligonucleotide probe of claim 1, wherein W provides spacing between MB, Fl and [A-B]$_n$ such that in an unhybridized form, the fluorescence of Fl in said oligonucleotide probe is less than 30% of unquenched fluorescence.

3. An oligonucleotide probe of claim 1, wherein W is a member selected from the group consisting of:

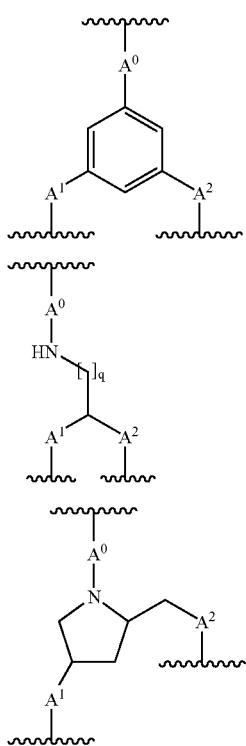

wherein q is an integer of from 0 to 8; and $A^0$, $A^1$ and $A^2$ are each linking groups having from 1 to 50 main chain atoms with portions selected from the group consisting of aryl, alkylene, substituted alkylene, heteroalkylene, substituted heteroalkylene and combinations thereof; and wherein the wavy lines indicate the points of attachment to MB, Q and $[A-B]_n$.

4. An oligonucleotide probe of claim 1, wherein n is an integer of from 6 to 18, and said $[A-B]_n$ portion comprises at least three consecutive guanine nucleotides wherein at least one of the guanine nucleotide bases is replaced by PPG.

5. An oligonucleotide probe of claim 4, wherein said $[A-B]_n$ portion is a DNA, a RNA, chimera, a PNA or a locked nucleic acid.

6. An oligonucleotide probe of claim 1, wherein n is an integer of from 6 to 18, said probe being complementary to a target sequence having at least 30% adenine and thymine bases, wherein said probe contains at least one modified base sufficient to provide an increase of stability of duplex formation of at least 3° C., relative to a probe without said at least one modified base.

7. An oligonucleotide probe of claim 6, wherein said $[A-B]_n$ portion is a DNA, a RNA, chimera, a PNA or a locked nucleic acid.

8. An oligonucleotide probe of claim 6, wherein said probe is complementary to a target sequence having at least 50% adenine and thymine bases, wherein said probe contains sufficient modified bases to provide an increase of stability of duplex formation of at least 5° C., relative to a probe without said modified bases.

9. An oligonucleotide probe of claim 1, wherein W and K have formulae IVb and IVc, respectively.

10. A method for continuous monitoring of polynucleotide amplification, comprising:

(a) combining a sample containing a target sequence, with one or more oligonucleotide primers complementary to regions of the target sequence, a polymerizing enzyme, nucleotide substrates, and an oligonucleotide conjugate having a formula:

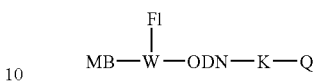

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence; to provide a mixture;

(b) incubating said mixture under conditions favorable for amplification of said polynucleotide; and (c) continuously monitoring said amplification by monitoring the fluorescence produced upon conjugate hybridization to amplified target.

11. A method of claim 10, wherein said MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs.

12. A method of claim 10, wherein said Fl portion is a fluorophore having an emission wavelengths of from about 400 nm to about 800 nm, said fluorophore being selected from the group consisting of coumarins, resorufins, xanthenes, benzoxanthenes, cyanines and dipyrromethene boron difluoride BODIPY™ analogs.

13. A method of claim 10, wherein said Q portion is a member selected from the group consisting of mono azo and bis azo dyes.

14. A method of claim 10, wherein said ODN portion of said conjugate is from 8-25 nucleotides in length.

15. A method of claim 10, wherein said ODN portion of said conjugate is from 8-15 nucleotides in length and K is a linker having a length of from 10-50 main chain atoms selected from the group consisting of C, O, N, S, P and Si.

16. A method of claim 10, wherein W and K have formulae IVb and IVc, respectively:

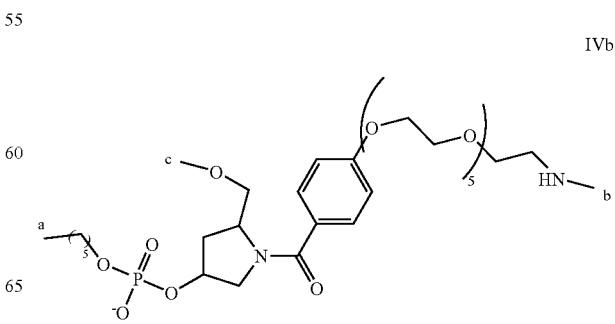

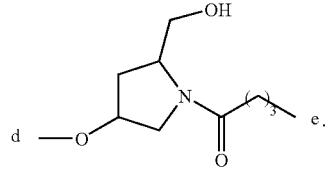

17. A method for monitoring gene expression comprising:
(a) providing an array of oligonucleotide probes of different sequences,
(b) incubating a population of polynucleotides with the array under hybridization conditions, and
(c) determining to which of the oligonucleotide probes in the array the population hybridizes;
wherein one or more of the oligonucleotide probes is an oligonucleotide conjugate having the formula:

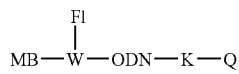

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence.

18. A method of claim 17, wherein said MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and dipyrromethene boron difluoride (BODIPY™) analogs, and said Q portion is a member selected from the group consisting of mono azo and bis azo dyes.

19. A method of claim 18, wherein said conjugates are attached to a solid support.

20. A method of claim 17, wherein W and K have the formulae IVb and IVc, respectively:

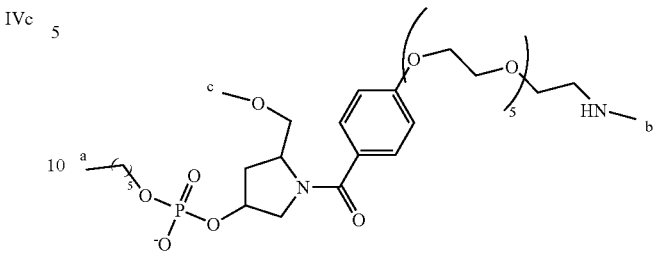

21. A method for discriminating between polynucleotides which differ by a single nucleotide, the method comprising:
(a) separately incubating each of at least two polynucleotides with an oligonucleotide conjugate having the formula:

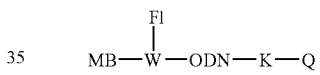

wherein MB is a minor groove binder, Q is a quencher, ODN is an oligonucleotide or modified oligonucleotide having a sequence that is complementary to a portion of said target sequence being amplified, K is a bond or a linking group, Fl is a fluorophore, W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence, said conjugate having a defined sequence under hybridization conditions, wherein one of the polynucleotides has a target sequence that is perfectly complementary to said oligonucleotide conjugate and at least one other of the polynucleotides has a target sequence having a single-nucleotide mismatch with the oligonucleotide conjugate; and
(b) determining the hybridization strength between each of the polynucleotides and the oligonucleotide conjugate.

22. A method of claim 21, wherein said MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and dipyrromethene boron difluoride (BODIPY™) analogs, and said Q portion is a member selected from the group consisting of mono azo and bis azo dyes.

23. A method of claim 21, wherein W and K have the formulae IVb and IVc, respectively:

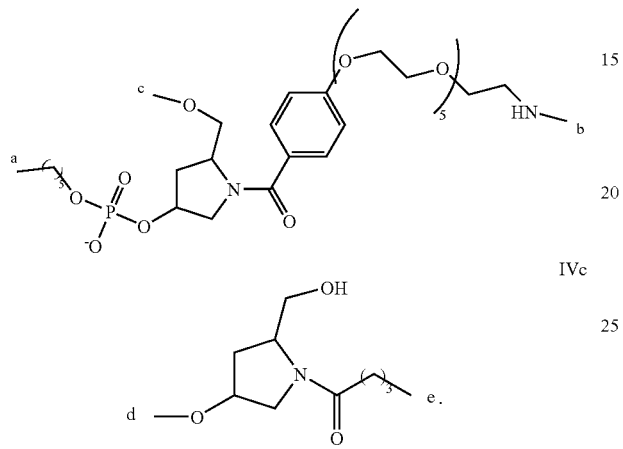

24. A method for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising:

(a) contacting the mixture of polynucleotides with an oligonucleotide conjugate having the formula:

$$\text{MB}-\overset{\text{Fl}}{\underset{|}{\text{W}}}-\text{ODN}-\text{K}-\text{Q}$$

wherein MB is a minor groove binder, Q is a quencher, ODN is an oligonucleotide or modified oligonucleotide, K is a bond or a linking group, Fl is a fluorophore and W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence; and wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence of said target sequence.

25. A method of claim 24, wherein said MB portion is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs, said Fl portion is a fluorophore having an emission wavelength of from about 400 nm to about 800 nm, said fluorophore being selected from the group consisting of coumarins, resorufins, xanthenes, benzoxanthenes, cyanines and dipyrromethene boron difluoride (BODIPY™) analogs, and said Q portion is a member selected from the group consisting of mono azo and bis azo dyes.

26. A method of claim 24, wherein W and K have the formulae IVb and IVc, respectively:

27. A method for distinguishing between wild-type, mutant and heterozygous target polynucleotides, said method comprising:

(a) contacting a sample containing a target polynucleotide with two probes wherein a first probe is specific for said wild-type target polynucleotide and a second probe is specific for said mutant target polynucleotide, each of said probes having a formula:

$$\text{MB}-\overset{\text{Fl}}{\underset{|}{\text{W}}}-\text{ODN}-\text{K}-\text{Q}$$

wherein MB is a minor groove binder, Q is a quencher, ODN is an oligonucleotide or modified oligonucleotide, K is a bond or a linking group, Fl is a fluorophore and W is a trivalent linking group that provides sufficient spacing between the MB, F and ODN components such that: i) MB binds in the minor groove when said oligonucleotide conjugate hybridizes to said target sequence; ii) in an unhybridized form, the fluorescence of Fl in said oligonucleotide conjugate is less than 10% of unquenched fluorescence; and iii) when said oligonucleotide conjugate hybridizes to said target sequence, the fluorescence of Fl is at least 50% of its unquenched fluorescence; and wherein the conjugate forms a stable hybrid only with said target sequence that is perfectly complementary to the ODN portion of said conjugate, and the conjugate does not form a stable hybrid with any of the other polynucleotides; and (b) measuring the fluorescence produced on hybrid formation, whereby hybrid formation indicates the presence or absence of each of said wild-type, mutant and heterozygous target polynucleotides.

28. A method of claim 27, wherein the melting temperatures ($T_m$) for each hybrid produced between said first and second probes and their respective targets are within about 5° C. of each other.

29. A method of claim 27, wherein the ODN portion of each of said probes is an oligonucleotide or modified oligonucleotide having from 8 to 18 bases or modified bases.

30. A method of claim 27, wherein the ODN portion of each of said probes is an oligonucleotide or modified oligonucleotide having from 10 to 15 bases or modified bases.

31. A method of claim 27, wherein the fluorophore portions of each of said probes are selected from the group consisting of 5-carboxyfluorescein (5-FAM™), 6-carboxyfluorescein (6-FAM™), 6-carboxy-2',4,7,7'-tetrachlorofluorescein (TET™), 6-carboxy-4',5'-dichloro-2',7'-dimethoxyfluorescein (JOE™), (6-carboxy2',4,4',5',7,7'hexachlorofluorescein) (HEX™), 6-carboxytetramethyirhodamine (TAMRA™), 5-carboxy-X-rhodamine (ROX™), dihydropyrimidine-2,4-dione, 5-(3-hydroxyprop-1-ynyl)-1, 3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-dpyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine.

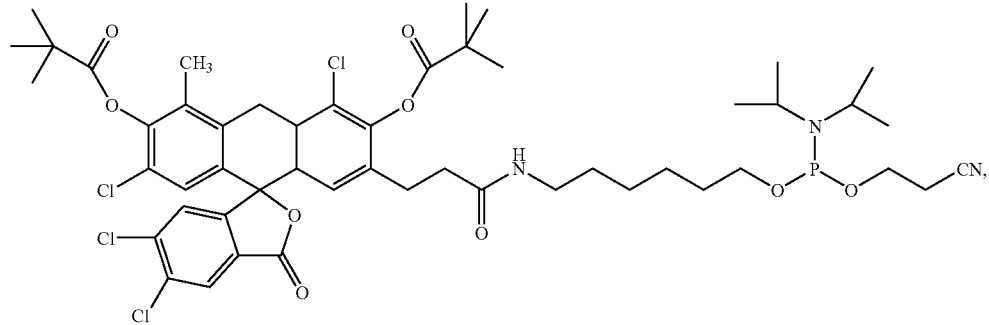

Yakima Yellow™, (YY)

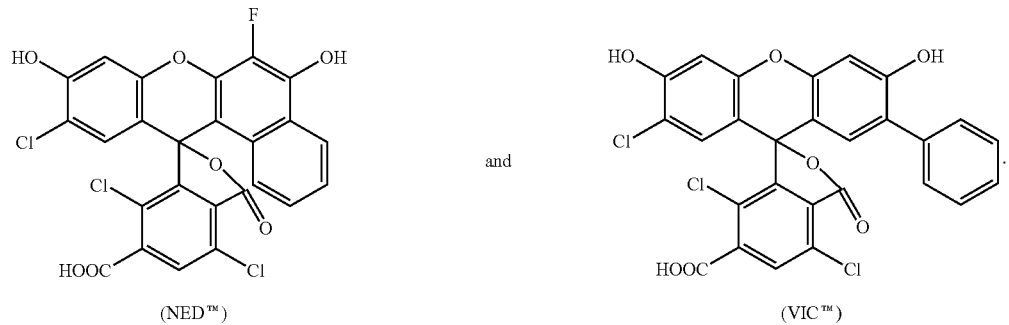

(NED™)           and           (VIC™)

32. A method of claim 27, wherein the ODN portion of each of said probes contains at least one modified base.

33. A method of claim 32, wherein each modified base is independently selected from the group consisting of 6-amino-1H-pyrazolo[3,4-d]pyrimidin-4(5H)-one, 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-yny)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-

34. A method of claim 27, wherein said sample is further contacted with a set of primers under amplification conditions and each of said primers contains from one to ten modified bases selected from the group consisting of 6-amino-1H-pyrazolo[3,4-d]pyrimidin-4(5H)-one, 4-amino-1H-pyrazolo[3,4-d]pyrimidine, 1H-pyrazolo[5,4-d]pyrimidin-4(5H)-6(7H)-dione, 6-amino-3-prop-6-amino-3-prop-1-ynyl-5-hydropyrazolo[3,4-d]pyrimidine-4-one, 6-amino-3-(3-hydroxyprop-1-yny)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl, 1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol [3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine.

* * * * *

UNITED STATES PATENT AND TRADEMARK OFFICE
CERTIFICATE OF CORRECTION

PATENT NO.      : 7,381,818 B2
APPLICATION NO. : 10/976365
DATED           : June 3, 2008
INVENTOR(S)     : Sergey Lokhov and Eugene Lukhtanov It is certified that error appears in the above-identified patent and that said Letters Patent is hereby corrected as shown below:

Claim 1, Column 83, line 55
should read

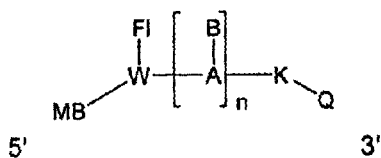

Claim 1, Column 83, line 65
"is a fluorophore; [A-B]n represents an nucleic acid oligomer"
should read
-- is a fluorophore; $[A-B]_n$ represents an nucleic acid oligomer --

Claim 1, Column 84, line 54
"sufficient spacing between MB, Fl and [A-B]n such that (i)"
should read
-- sufficient spacing between MB, Fl and $[A-B]_n$ such that (i) --

Claim 6, Column 85, line 52
"formation of at least 3°C., relative to a probe without said"
should read
-- formation of at least 3°C, relative to a probe without said --

Claim 8, Column 85, line 62
"stability of duplex formation of at least 5°C., relative to a"
should read
-- stability of duplex formation of at least 5°C, relative to a --

Claim 34, Column 92, line 57
"d]pyrimidin-4(5*H*)-6(7*H*)-dione, 6-amino-3-prop-6amino-"
should read
-- d]pyrimidin-4(5*H*)-6(7*H*)-dione, 6-amino-3-prop --

Claim 34, Column 92, line 58
"3-prop-1-ynyl-5-hydropyrazolo[3,4-d]pyrimidine-4-one"
should read
-- -1-ynyl-5-hydropyrazolo[3,4-d]pyrimidine-4-one --

UNITED STATES PATENT AND TRADEMARK OFFICE
CERTIFICATE OF CORRECTION

PATENT NO. : 7,381,818 B2
APPLICATION NO. : 10/976365
DATED : June 3, 2008
INVENTOR(S) : Sergey Lokhov and Eugene Lukhtanov It is certified that error appears in the above-identified patent and that said Letters Patent is hereby corrected as shown below:

Claim 34, Column 93, line 1
"5-prop-1-ynyl, 1,3-dihydropyrimidine-2,4-dione"
should read
-- 5-prop-1-ynyl-1,3-dihydropyrimidine-2,4-dione --

Signed and Sealed this

Sixth Day of January, 2009

JON W. DUDAS
*Director of the United States Patent and Trademark Office*